United States Patent
Wu

(10) Patent No.: US 10,889,586 B2
(45) Date of Patent: Jan. 12, 2021

(54) MULTI-KINASE INHIBITOR COMPOUND, AND CRYSTAL FORM AND USE THEREOF

(71) Applicant: Nanjing TransThera Biosciences Co. Ltd., Nanjing (CN)

(72) Inventor: Frank Wu, Nanjing (CN)

(73) Assignee: Nanjing TransThera Biosciences Co. Ltd., Nanjing (CN)

( * ) Notice: Subject to any disclaimer, the term of this patent is extended or adjusted under 35 U.S.C. 154(b) by 0 days.

(21) Appl. No.: 16/257,342

(22) Filed: Jan. 25, 2019

(65) Prior Publication Data

US 2019/0152972 A1 May 23, 2019

Related U.S. Application Data

(63) Continuation of application No. 16/156,371, filed on Oct. 10, 2018, now Pat. No. 10,208,042, which is a continuation of application No. PCT/CN2017/115698, filed on Dec. 12, 2017.

(30) Foreign Application Priority Data

| Dec. 13, 2016 | (CN) | 2016 1 1174146 |
| Jun. 8, 2017 | (CN) | 2017 1 0426594 |
| Jul. 20, 2017 | (CN) | 2017 1 0593933 |

(51) Int. Cl.
| C07D 471/14 | (2006.01) |
| C07D 491/08 | (2006.01) |
| C07D 487/04 | (2006.01) |
| C07D 519/00 | (2006.01) |
| A61K 45/06 | (2006.01) |
| A61K 31/551 | (2006.01) |
| A61K 31/5517 | (2006.01) |
| A61P 35/00 | (2006.01) |
| A61P 35/02 | (2006.01) |

(52) U.S. Cl.
CPC .......... *C07D 471/14* (2013.01); *A61K 31/551* (2013.01); *A61K 31/5517* (2013.01); *A61K 45/06* (2013.01); *A61P 35/00* (2018.01); *A61P 35/02* (2018.01); *C07D 487/04* (2013.01); *C07D 491/08* (2013.01); *C07D 519/00* (2013.01)

(58) Field of Classification Search
CPC .. C07D 471/14; C07D 487/04; C07D 491/08; C07D 519/00; A61P 35/02; A61P 35/00; A61K 31/551; A61K 31/06; A61K 45/06
USPC ........................................................ 514/220
See application file for complete search history.

(56) References Cited

U.S. PATENT DOCUMENTS

| 6,350,786 B1 * | 2/2002 | Albano .................. A61K 47/56 514/772.4 |
| 6,440,959 B1 | 8/2002 | Ding et al. |
| 10,208,042 B1 | 2/2019 | Wu |
| 2015/0011536 A1 * | 1/2015 | Wu ...................... C07D 471/14 514/220 |

FOREIGN PATENT DOCUMENTS

| CN | 1251312 A | 4/2000 |
| CN | 1348455 A | 5/2002 |
| CN | 102603743 A | 7/2012 |
| EP | 2818171 A1 | 12/2014 |
| JP | 2000-95708 A | 4/2000 |
| JP | 2002-543081 A | 12/2002 |
| JP | 2015-508083 A | 3/2015 |
| WO | WO-2000/64900 A1 | 11/2000 |
| WO | WO-2006/040036 A1 | 4/2006 |

OTHER PUBLICATIONS

Muruganandham et al Molecular Cancer Therapeutics, 2006, 5(8), 1950-1957 (Year: 2006).*
Liu et al., Discovery of a highly potent, orally active mitosis/angiogenesis inhibitor r1530 for the treatment of solid tumors. ACS Med Chem Lett. Jan. 15, 2013;4(2):259-63.
Liu et al., Pyrazolobenzodiazepines: part I. Synthesis and SAR of a potent class of kinase inhibitors. Bioorg Med Chem Lett. Oct. 15, 2010;20(20):5984-7.

(Continued)

*Primary Examiner* — Yevgeny Valenrod
(74) *Attorney, Agent, or Firm* — McCarter & English, LLP; Steven G. Davis; Wei Song

(57) ABSTRACT

The present invention relates to a compound as represented by formula (I) or a pharmaceutically acceptable salt and stereoisomer thereof, wherein $R_1$, $R_2$, X, Y, P, W, and Ar are as defined in the description. The compound of formula (I) of the present invention can be used in the preparation of a drug for treating cancers mediated by abnormality of multi-kinases. Also provided is a crystal form I of a compound 4-(5-(2-chlorophenyl)-3-methyl-2,10-dihydropyrazolo[4,3-b]pyrido[4,3-e][1,4]diazepin-8-yl)morpholine, wherein in an X-ray powder diffraction pattern of crystal form I, there are characteristic peaks at 7.4±0.2°, 17.9±0.2°, 18.9±0.2°, 19.4±0.2°, 21.5±0.2°, and 23.7±0.2°.

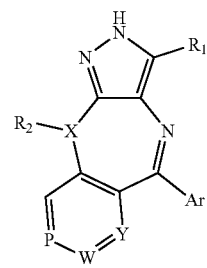

(I)

20 Claims, 2 Drawing Sheets

(56) References Cited

OTHER PUBLICATIONS

International Search Report and Written Opinion for Applicatioin No. PCT/CN2017/115698, dated Mar. 16, 2018. 14 pages.
Australian Office Action for Application No. 2017376353, dated Nov. 1, 2019, 4 pages.

* cited by examiner

MULTI-KINASE INHIBITOR COMPOUND, AND CRYSTAL FORM AND USE THEREOF

This application is a continuation application of, and claims priority of U.S. patent application Ser. No. 16/156,371, filed on Oct. 10, 2018, and entitled "MULTI-KINASE INHIBITOR COMPOUND, AND CRYSTAL FORM AND USE THEREOF", which is a continuation application of International Application No. PCT/CN2017/115698, filed on Dec. 12, 2017, which applications further claim the priority of the Chinese patent application of No. 201611174146.3, titled "A SYNTHESIS METHOD OF MULTI-KINASES INHIBITOR AND USE THEREOF", filed with State Intellectual Property Office of the P.R.C on Dec. 13, 2016; the Chinese patent application of No. 201710426594.6, titled "MULTI-KINASES INHIBITOR AND USE THEREOF", filed with State Intellectual Property Office of the P.R.C on Jun. 8, 2017; and the Chinese patent application of No. 201710593933.X, titled "CRYSTAL FORM OF MULTI-KINASE INHIBITOR, AND PREPARATION METHOD AND USE THEREOF", filed with State Intellectual Property Office of the P.R.C on Jul. 20, 2017. The entire contents of the aforementioned applications are incorporated herein by reference.

TECHNICAL FIELD

The invention belongs to the field of medicine technology, particularly relates to a multi-kinases inhibitor compound, a crystal form and use thereof.

BACKGROUND

Normal cell division is essential for the health of the body and the survival of cellular organs. During this process, the intracellular material is completely recombined, and two identical chromosome copies are separated into two daughter cells by a bipolar spindle. When an error occurs in the mitosis process, chromosomal number in the cell will be abnormal, which may lead to cell death or promote the development of normal cells to tumor cells. The mitosis process mainly depends on three mechanisms: ① protein localization; ② proteolysis; ③ phosphorylation. During the processes, some serine/threonine kinases, also known as mitotic kinases, are involved.

Aurora kinase is one kind of the mitotic kinases and was discovered in 1995. The expression of Aurora kinase was first observed in human tumor tissue in 1998. It has now become a target of concern for anti-cancer research. The Aurora kinase family includes three highly homologous kinases: Aurora A, Aurora B, and Aurora C. Among them, Aurora A and Aurora B are detectable.

Aurora A has now been demonstrated to be an oncogene, whose overexpression blocks the correct assembly of mitotic checkpoint complexes, resulting in genetic instability and tumor formation. Aurora B is an important kinase that regulates normal cell mitosis. Overexpression of Aurora B is widespread in tumors. Tumor cells become more sensitive when Aurora B is inhibited. In view of the key roles of Aurora A and Aurora B in the process of cell mitosis, the research and development of anti-tumor drugs targeting Aurora kinase have attracted more and more attention. In addition, Aurora kinases are ineffective against non-proliferating cells since they are expressed and activated in mitosis. Therefore, Aurora kinase inhibitors belong to targeted anti-tumor drugs and will have greater advantages over other non-specific cytotoxic drugs.

In addition to being associated with overexpression of mitotic kinases, tumor growth and migration also depend on the production of a large number of new blood vessels, in which VEGF/VEGFR (vascular endothelial growth factor/vascular endothelial growth factor receptor) pathway plays a key role in tumor neovascularization. Among them, VEGFR is a type of tyrosine kinase transmembrane glycoprotein consisted of an extracellular region composed of 7 Ig-like domains, one transmembrane domain and a cytoplasmic tyrosine kinase structural region. There are three subtypes of VEGFR, which are VEGFR1, VEGFR2, and VEGFR3. The conformation of VEGFR changes after bonding with VEGF, which leads to dimerization of the receptor, autophosphorylation of the tyrosine site in the intracellular segment and activation of downstream signal transduction pathway. VEGFR2 (KDR) is mainly distributed in vascular endothelial cells and hematopoietic stem cells. VEGFR2 (KDR) is closely related to hematopoietic system dysfunction before malignant proliferative lesions, such as throbocythemia, primary throbocythemia, myelofibrosis (MF), chronic idiopathic myelofibrosis (IMF), polycythemia (PV), pre-cancerous myelodysplastic syndrome, and hematological malignancies. Among those, hematologic malignancies include, but are not limited to, leukemia (non-Hodgkin's lymphoma), Hodgkin's disease (also known as Hodgkin's lymphoma) and myeloma, for example, acute lymphoblastic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), etc.

At present, there are clinical inhibitors against Aurora A and Aurora B respectively, as well as inhibitors against VEGFR. However, no multi-kinases inhibitors that are effective against the above kinases simultaneously are available. WO2013123840A1 discloses a class of azabenzo[f] azulene derivatives having antitumor effects without any therapeutic mechanism thereof.

SUMMARY OF THE INVENTION

The present invention provides a class of compounds (multi-kinases inhibitors) shown in formulas (I) and (II), or pharmaceutically acceptable salts or stereoisomers thereof, capable of inhibiting, regulating and/or modulating the activity of one or more protein kinases such as Aurora kinase and VEGFR kinase; a crystal form I of the compound shown in formula (III); and pharmaceutical formulation and pharmaceutical composition comprising the above compounds and/or the crystal form I, for use in treating diseases mediated by these kinase abnormalities, particularly cancer-related diseases. The invention also provides methods for preparing the above compounds and crystal form, and methods for using the compounds, crystal form, pharmaceutical formulation and/or pharmaceutical composition to treat the above-described diseases in mammals, particularly humans.

For the purpose above, the present invention firstly provides a compound shown in formula (I), or pharmaceutically acceptable salts or stereoisomers thereof:

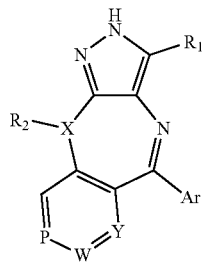

(I)

wherein,

X is selected from CH or N;

$R_1$ is selected from the group consisting of hydrogen, $C_{1-6}$ alkyl, $C_{3-6}$ cycloalkyl, $C_{1-6}$ alkoxy, halogenated $C_{1-6}$ alkyl or halogenated $C_{1-6}$ alkoxy;

$R_2$ is selected from the group consisting of hydrogen, $C_{1-6}$ alkyl or $C_{3-6}$ cycloalkyl;

Y is selected from $CR_3$ or N;

P is selected from $CR_4$ or N;

W is selected from $CR_5$ or N;

$R_3$, $R_4$ and $R_5$ are independently selected from the group consisting of hydrogen, hydroxyl, amino, carboxyl, cyano, nitro, halogen, $C_{1-6}$ alkyl, $C_{1-6}$ alkoxy, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, $-NR_{11}-(CH_2)_n-N(R_7)(R_8)$, $C_{1-6}$ alkylthio-$(CH_2)_n-$, $-(CH_2)_n$-(3-14) membered cycloalkyl, $-(CH_2)_n$-(6-14) membered aryl, $-(CH_2)_n$-(5-14) membered heterocyclyl and $-(CH_2)_n$-(5-14) membered heteroaryl; wherein, n=0-6; the ring-forming S atom in the cycloalkyl, aryl, heterocyclyl or heteroaryl can be optionally oxidized to $S(O)$ or $S(O)_2$, the ring-forming C atom in cycloalkyl, aryl, heterocyclyl or heteroaryl can be optionally oxidized to $C(O)$; and cycloalkyl, aryl, heteroaryl or heterocyclyl can be optionally substituted with one or more independent $C_{1-3}$ alkyl or $C_{3-6}$ cycloalkyl;

$R_7$ and $R_8$ are independently selected from the group consisting of hydrogen, $C_{1-6}$ alkyl, $C_{3-6}$ cycloalkyl, $C_{1-6}$ alkoxy, halogenated $C_{1-6}$ alkyl, or halogenated $C_{1-6}$ alkoxy; and P, W, and Y are not N simultaneously, when Y is $CR_3$, P is $CR_4$, and W is N, $R_4$ cannot be selected from $C_{1-6}$ alkyl, when Y is $CR_3$, P is $CR_4$, and W is $CR_5$, one of $R_4$ and $R_5$ must be H;

Ar is selected from the group consisting of 3-14 membered cycloalkyl, 6-14 membered aryl, 5-14 membered heterocyclyl, or 5-14 membered heteroaryl; the ring-forming S atom in cycloalkyl, aryl, heterocyclyl or heteroaryl can be optionally oxidized to $S(O)$ or $S(O)_2$, and the ring-forming C atom in cycloalkyl, aryl, heterocyclyl or heteroaryl can be optionally oxidized to $C(O)$; and Ar can be optionally substituted with 1 to 3 $R_6$;

$R_6$ is each independently selected from the group consisting of hydrogen, hydroxyl, amino, carboxyl, cyano, nitro, halogen, $C_{1-6}$ alkyl, $C_{3-6}$ cycloalkyl, $C_{1-6}$ alkoxy, $C_{3-6}$ cycloalkyloxy, halogenated $C_{1-6}$ alkoxy, halogenated $C_{1-6}$ alkyl, $C_{3-6}$ cycloalkyl, $C_{2-8}$ alkenyl, $C_{2-8}$ alkynyl, $-NR_{11}-(CH_2)_n-N(R_9)(R_{10})$, amino $C_{1-6}$ alkyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, $C_{1-6}$ alkylthio, $-(CH_2)_n$-(6-14) membered cycloalkyl, $-(CH_2)_n$-(6-14) membered aryl, $-(CH_2)_n$-(5-14) membered heterocyclyl or $-(CH_2)_n$-(5-14) membered heteroaryl; wherein n=0-6, and cycloalkyl, aryl, heteroaryl or heterocyclyl can be optionally substituted with one or more independent $C_{1-3}$ alkyl;

$R_9$ and $R_{10}$ are independently selected from the group consisting of hydrogen, $C_{1-6}$ alkyl, $C_{3-6}$ cycloalkyl, $C_{1-6}$ alkoxy, halogenated $C_{1-6}$ alkyl or halogenated $C_{1-6}$ alkoxy;

$R_{11}$ is selected from the group consisting of hydrogen, $C_{1-6}$ alkyl or $C_{3-6}$ cycloalkyl.

One embodiment of the present invention relates to the aforementioned compound shown in formula (I), pharmaceutically acceptable salts thereof, or stereoisomers thereof, wherein, $R_1$ is selected from $C_{1-3}$ alkyl, preferably methyl or ethyl;

$R_2$ is selected from the group consisting of hydrogen, methyl, and ethyl;

X is selected from N.

One embodiment of the present invention relates to the aforementioned compound shown in formula (I), pharmaceutically acceptable salts thereof, or stereoisomers thereof, wherein, Ar is selected from the group consisting of 6-14 membered aryl or 5-14 membered heteroaryl; any ring-forming S atom in aryl and heteroaryl can be optionally oxidized to $S(O)$ or $S(O)_2$, the ring-forming C in aryl and heteroaryl atom can be optionally oxidized to $C(O)$; and Ar can be optionally substituted with 1 to 3 $R_6$;

$R_6$ is selected from the group consisting of hydrogen, amino, cyano, halogen, $C_{1-4}$ alkyl, trifluoromethyl, methylsulfonyl, $-(CH_2)_n$-(5-14) membered heterocyclyl, $-(CH_2)_n$-(5-14) membered heteroaryl, wherein n=0-6, and the heteroaryl ring and heterocyclyl can be optionally substituted with $C_{1-3}$ alkyl.

One embodiment of the present invention relates to the aforementioned compound shown in formula (I), pharmaceutically acceptable salts thereof, or stereoisomers thereof, wherein, X is N;

$R_1$ is selected from $C_{1-3}$ alkyl, preferably methyl or ethyl;

$R_2$ is selected from the group consisting of hydrogen, methyl and ethyl;

Y is selected from $CR_3$ or N;

P is selected from $CR_4$ or N;

W is selected from $CR_5$ or N;

$R_3$, $R_4$ and $R_5$ are independently selected from the group consisting of hydrogen, hydroxyl, amino, carboxyl, cyano, nitro, halogen, $C_{1-6}$ alkyl, $C_{1-6}$ alkoxy, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, $-NR_{11}-(CH_2)_n-N(R_7)(R_8)$, $C_{1-6}$ alkylthio-$(CH_2)_n-$, $-(CH_2)_n$-(3-14) membered cycloalkyl, $-(CH_2)_n$-(6-14) membered aryl, $-(CH_2)_n$-(5-14) membered heterocyclyl or $-(CH_2)_n$-(5-14) membered heteroaryl; wherein n=0-6; the ring-forming S atom in cycloalkyl, aryl, heterocyclyl or heteroaryl can be optionally oxidized to $S(O)$ or $S(O)_2$, the ring-forming C atom in cycloalkyl, aryl, heterocyclyl or heteroaryl can be optionally oxidized to $C(O)$; and cycloalkyl, aryl, heteroaryl or heterocyclyl can be optionally substituted with one or more independent $C_{1-3}$ alkyl or $C_{3-6}$ cycloalkyl;

$R_7$ and $R_8$ are independently selected from the group consisting of hydrogen, $C_{1-6}$ alkyl, $C_{3-6}$ cycloalkyl, $C_{1-6}$ alkoxy, halogenated $C_{1-6}$ alkyl or halogenated $C_{1-6}$ alkoxy; and P, W, and Y are not N simultaneously, when Y is $CR_3$, P is $CR_4$, and W is N, $R_4$ cannot be selected from $C_{1-6}$ alkyl, when Y is $CR_3$, P is $CR_4$, and W is $CR_5$, one of $R_4$ and $R_5$ must be H;

$R_{11}$ is selected from the group consisting of hydrogen, $C_{1-6}$ alkyl and $C_{3-6}$ cycloalkyl;

Ar is selected from the group consisting of 6-14 membered aryl or 5-10 membered heteroaryl; the ring-forming S atom in aryl and heteroaryl can be optionally oxidized to S(O) or $S(O)_2$, the ring-forming C atom in aryl and heteroaryl can be optionally oxidized to C(O); and wherein Ar can be optionally substituted with 1 to 3 $R_6$;

$R_6$ is each independently selected from the group consisting of hydrogen, amino, cyano, halogen, $C_{1-4}$ alkyl, trifluoromethyl, methylsulfonyl, —$(CH_2)_n$-(5-10) membered heterocyclyl or —$(CH_2)_n$-(5-10) membered heteroaryl; wherein n=0-6; and heteroaryl and heterocyclyl can be optionally substituted with one or more independent $C_{1-3}$ alkyl.

One embodiment of the present invention relates to the aforementioned compound shown in formula (II), pharmaceutically acceptable salts thereof, or stereoisomers thereof:

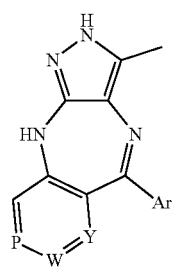

(II)

wherein,

Ar is selected from the group consisting of 5-6 membered aryl or 5-6 membered heteroaryl; the ring-forming S atom in aryl and heteroaryl can be optionally oxidized to S(O) or $S(O)_2$, and the ring-forming C atom in aryl and heteroaryl can be optionally oxidized to C(O); and wherein Ar can be optionally substituted with 1 to 3 $R_6$;

$R_6$ is each independently selected from the group consisting of hydrogen, amino, cyano, halogen, $C_{1-4}$ alkyl, trifluoromethyl or methylsulfonyl, and halogen is preferably chlorine;

Y is selected from $CR_3$ or N;
P is selected from $CR_4$ or N;
W is selected from $CR_5$ or N;

$R_3$, $R_4$ and $R_5$ are independently selected from the group consisting of hydrogen, hydroxyl, amino, carboxyl, cyano, nitro, halogen, $C_{1-4}$ alkyl, $C_{1-4}$ alkoxy, $C_{3-6}$ cycloalkyloxy, oxa $C_{5-8}$ cycloalkyloxy, halogenated $C_{1-4}$ alkoxy, $C_{2-6}$ alkenyl, $C_{2-6}$ alkynyl, $C_{3-6}$ cycloalkylamino, $C_{1-4}$ alkylsulfonyl, $C_{3-8}$ cycloalkylsulfonyl, $C_{1-4}$ alkylcarbonyl, $C_{3-6}$ cycloalkylcarbonyl, —$NR_{11}$—$(CH_2)_n$—$N(R_7)(R_8)$, —$(CH_2)_n$-(3-14) membered cycloalkyl, —$(CH_2)_n$-(5-11) membered heterocyclyl or —$(CH_2)_n$-(5-10) membered heteroaryl; wherein, n=0-6; the ring-forming S atom in cycloalkyl, heterocyclyl or heteroaryl can be optionally oxidized to S(O) or $S(O)_2$, the ring-forming C atom in cycloalkyl, heterocyclyl or heteroaryl can be optionally oxidized to C(O); and cycloalkyl, heteroaryl or heterocyclyl can be optionally substituted with one or more independent $C_{1-3}$ alkyl or $C_{3-6}$ cycloalkyl;

$R_7$ and $R_8$ are independently selected from hydrogen, methyl, ethyl, isopropyl or cyclopropyl; and P, W, and Y are not N simultaneously, and at least one of P, W, and Y is N;

when Y is $CR_3$, P is $CR_4$, and W is N, $R_4$ cannot be selected from $C_{1-4}$ alkyl;

$R_{11}$ is selected from the group consisting of hydrogen, $C_{1-6}$ alkyl and $C_{3-6}$ cycloalkyl. preferably, Y is $CR_3$;
P is $CR_4$;
W is N;
$R_4$ cannot be selected from $C_{1-4}$ alkyl.

One embodiment of the present invention relates to the aforementioned compound shown in formula (I) or (II), pharmaceutically acceptable salts thereof, or stereoisomers thereof, wherein, Ar can be selected from the group consisting of:

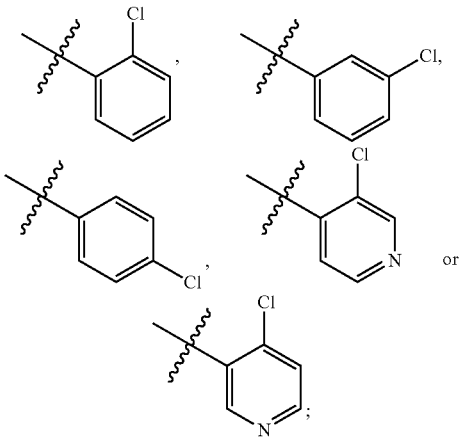

Y is selected from $CR_3$ or N;
P is selected from $CR_4$ or N;
W is selected from $CR_5$ or N;

$R_3$, $R_4$ and $R_5$ are independently selected from the group consisting of: hydrogen, methyl, ethyl, isopropyl,

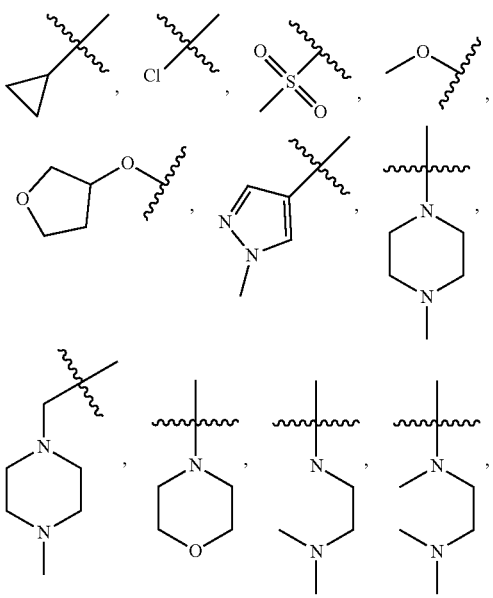

-continued

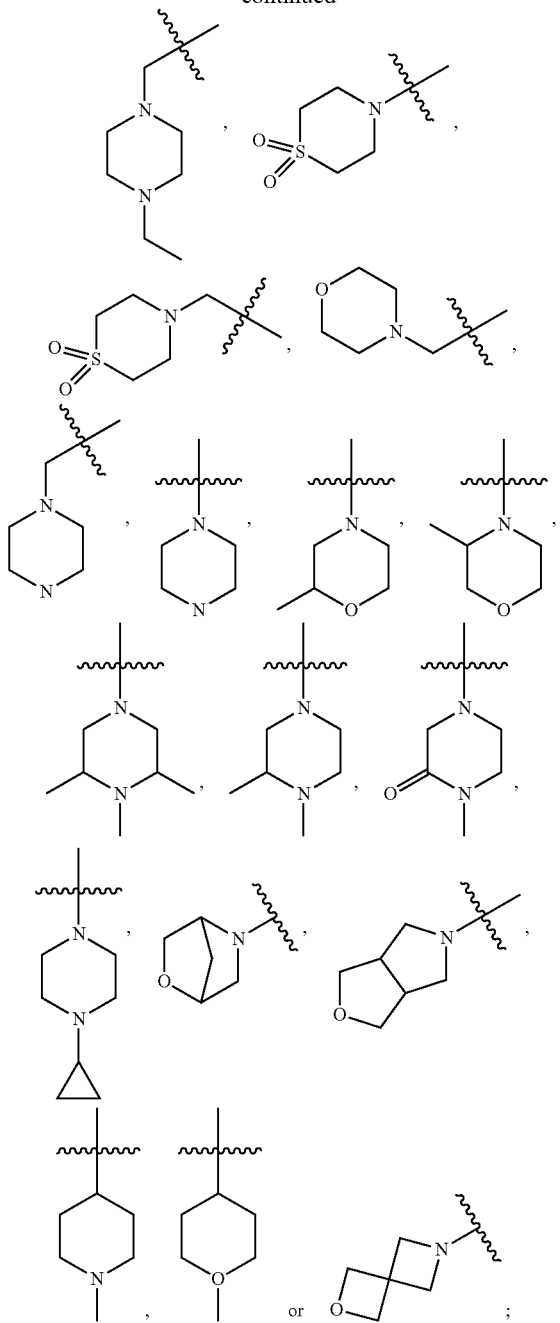

and

P, W, and Y are not N simultaneously, and at least one of P, W, and Y is N;

when Y is $CR_3$, P is $CR_4$, and W is N, $R_4$ cannot be methyl, ethyl or isopropyl;

preferably,

Y is $CR_3$;

P is $CR_4$;

W is N.

One embodiment of the present invention relates to the aforementioned compound shown in formula (I) or (II), pharmaceutically acceptable salts thereof, or stereoisomers thereof, wherein, Ar is selected from phenyl or 5-6 membered heteroaryl, Ar can be optionally substituted with 1 to 3 $R_6$, and $R_6$ is each independently selected from the group consisting of hydrogen, amino, cyano, halogen, $C_{1-4}$ alkyl, trifluoromethyl or methylsulfonyl;

Y is selected from $CR_3$;

P is selected from $CR_4$;

W is selected from N;

$R_3$ is selected from hydrogen or $C_{1-4}$ alkyl;

$R_4$ is selected from the group consisting of hydrogen, hydroxyl, amino, carboxyl, cyano, nitro, halogen, $C_{1-4}$ alkoxy, $C_{3-6}$ cycloalkyloxy, oxa $C_{5-8}$ cycloalkyloxy, halogenated $C_{1-4}$ alkoxy, $C_{3-6}$ cycloalkylamino, $C_{1-4}$ alkylsulfonyl, $C_{3-6}$ cycloalkylsulfonyl, $C_{1-4}$ alkylcarbonyl, $C_{3-6}$ cycloalkylcarbonyl, —$NR_{11}$—$(CH_2)_n$—$N(R_7)(R_8)$, —$(CH_2)_n$—$C_{3-10}$ cycloalkyl, —$(CH_2)_n$-(5-11) membered heterocyclyl, or —$(CH_2)_n$-(5-10) membered heteroaryl; wherein, n=0-6; the ring-forming S atom in cycloalkyl, heterocyclyl or heteroaryl can be optionally oxidized to $S(O)$ or $S(O)_2$, the ring-forming C atom in cycloalkyl, heterocyclyl or heteroaryl can be optionally oxidized to $C(O)$; and cycloalkyl, heteroaryl or heterocyclyl can be optionally substituted with one or more independent $C_{1-3}$ alkyl or $C_{3-6}$ cycloalkyl.

One embodiment of the present invention relates to the aforementioned compound of the formula (I) or (II), pharmaceutically acceptable salts thereof, or stereoisomers thereof, wherein, Ar is selected from phenyl or pyridyl, Ar can be optionally substituted with 1-3 $R_6$, $R_6$ each independently selected from the group consisting of hydrogen, amino, cyano, halogen, $C_{1-4}$ alkyl, trifluoromethyl or methylsulfonyl;

Y is $CR_3$;

P is $CR_4$;

W is N;

$R_3$ is selected from hydrogen or $C_{1-4}$ alkyl;

$R_4$ is selected from the group consisting of hydrogen, hydroxyl, amino, carboxyl, cyano, nitro, halogen, $C_{1-4}$ alkoxy, $C_{3-6}$ cycloalkyloxy, halogenated $C_{1-4}$ alkoxy, $C_{3-6}$ cycloalkylamino, $C_{1-4}$ alkylsulfonyl, $C_{1-4}$ alkylcarbonyl, $C_{3-6}$ cycloalkylcarbonyl, —$NR_{11}$—$(CH_2)_n$—$N(R_7)(R_8)$, —$(CH_2)_n$—$C_{3-6}$ cycloalkyl, —$(CH_2)_n$-(5-6) membered monoheterocyclyl, —$(CH_2)_n$-(7-11) membered fused heterocyclyl, —$(CH_2)_n$-(5-6) monoheteroaryl, or —$(CH_2)_n$-(8-10) membered fused heteroaryl, wherein, n=0-6, the ring-forming S atom in cycloalkyl, heterocyclyl or heteroaryl can be optionally oxidized to $S(O)$ or $S(O)_2$, and the ring-forming C atom in cycloalkyl, heterocyclyl or heteroaryl can be optionally oxidized to $C(O)$; the cycloalkyl, heteroaryl, heterocyclyl can be optionally substituted with one or more independent $C_{1-3}$ alkyl or $C_{3-6}$ cycloalkyl;

wherein, (1) $R_4$ is preferably selected from the group consisting of halogen, $C_{1-4}$ alkoxy, halogenated $C_{1-4}$ alkoxy, $C_{1-4}$ alkylsulfonyl, $C_{3-6}$ cycloalkylcarbonyl, —$NR_{11}$—$(CH_2)_n$—$N(R_7)(R_8)$, —$(CH_2)_n$—$C_{3-6}$ cycloalkyl, —$(CH_2)_n$-(5-6) membered monoheterocyclyl, and —$(CH_2)_n$-(7-11) membered fused heterocyclyl; wherein, n=0-6; the ring-forming S atom in cycloalkyl or heterocyclyl can be optionally oxidized to $S(O)$ or $S(O)_2$, and the ring-forming C atom in cycloalkyl or heterocyclyl can be optionally oxidized to $C(O)$; and cycloalkyl or heterocyclyl can be optionally substituted with one or more independent $C_{1-3}$ alkyl or $C_{3-6}$ cycloalkyl;

the 5-6 membered monoheterocyclyl is preferably 5-6 membered saturated monoheterocyclyl, and the 7-11 membered fused heterocyclyl is preferably 7-11 membered saturated fused heterocyclyl, more preferably 7-11 members saturated ortho-fused heterocyclyl, 7-11 membered saturated spiro-heterocyclyl, or 7-11 membered saturated bridged heterocyclyl;

(2) $R_4$ is further preferably selected from the group consisting of: halogen, $C_{1-4}$ alkoxy, —$NR_1$—$(CH_2)_n$—$N(R_7)(R_8)$, $C_{1-4}$ alkylsulfonyl,

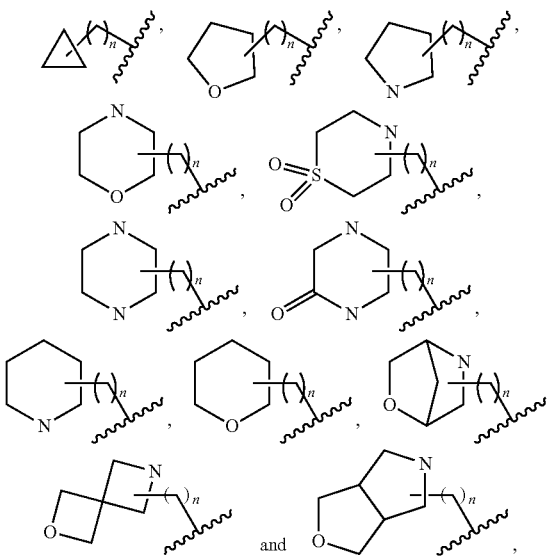

and n=0-3; wherein the cycloalkyl or heterocyclyl can be optionally substituted with one or more independent $C_{1-3}$ alkyl groups or $C_{3-6}$ cycloalkyl groups;

(3) $R_4$ is more preferably selected from the group consisting of: halogen, $C_{1-4}$ alkoxy, —$NR_{11}$—$(CH_2)_n$—$N(R_7)(R_8)$, $C_{1-4}$ alkylsulfonyl,

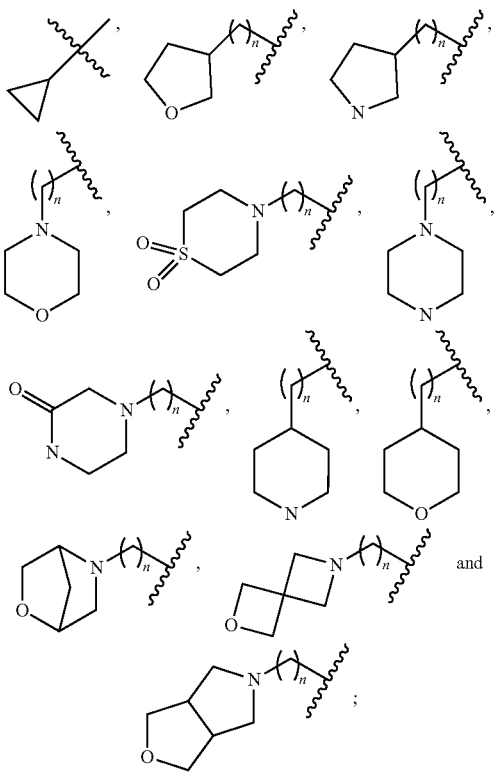

and

;

n=0-3; wherein cycloalkyl or heterocyclyl can be optionally substituted with one or more independent $C_{1-3}$ alkyl groups or $C_{3-6}$ cycloalkyl groups;

In one embodiment of the present invention, the aforementioned compound shown as formula (I) or (II), pharmaceutically acceptable salts thereof or stereoisomers thereof are shown in Table 1:

TABLE 1

| Number | Structure |
|---|---|
| 1 | 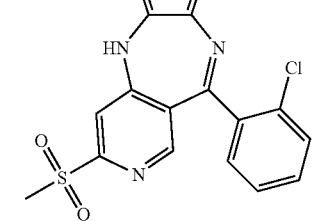 |
| 2 | 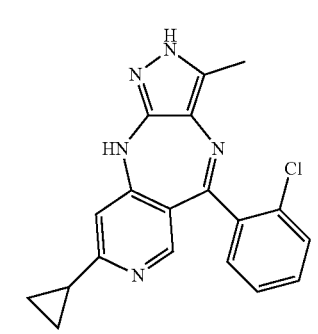 [SMILES: Cc1[nH]nc2c1N=C(c1ccccc1Cl)c1cnc(C3CC3)cc1N2] |
| 3 | 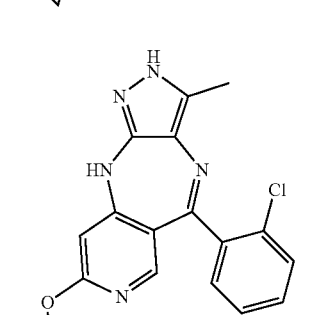 |
| 4 | 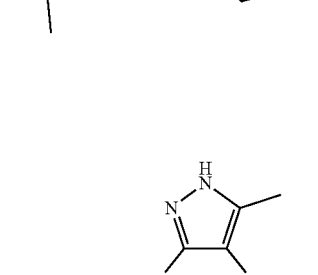 |

TABLE 1-continued

| Number | Structure |
|---|---|
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |

TABLE 1-continued

| Number | Structure |
|---|---|
| 14 | (structure) |
| 15 | (structure) |
| 16 | (structure) |
| 17 | (structure) |
| 18 | (structure) |
| 19 | (structure) |
| 20 | (structure) |
| 21 | (structure) |

TABLE 1-continued

| Number | Structure |
|---|---|
| 22 | 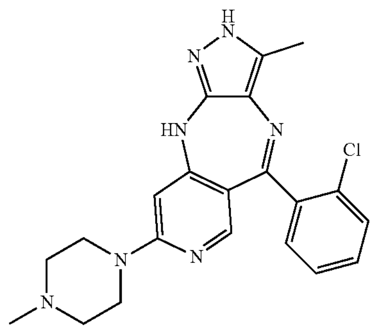 [SMILES: Cc1[nH]nc2c1N=C(c1ccccc1Cl)c1cnc(N3CCN(C)CC3)cc1N2] |
| 23 | 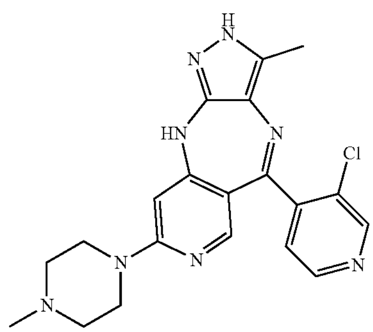 [SMILES: Cc1[nH]nc2c1N=C(c1ccncc1Cl)c1cnc(N3CCN(C)CC3)cc1N2] |
| 24 | 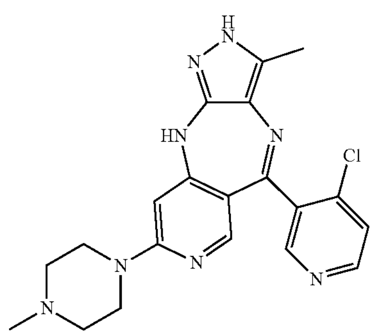 [SMILES: Cc1[nH]nc2c1N=C(c1cnccc1Cl)c1cnc(N3CCN(C)CC3)cc1N2] |
| 25 | 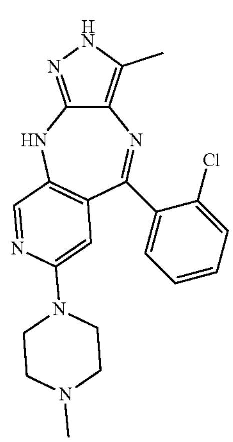 [SMILES: Cc1[nH]nc2c1N=C(c1ccccc1Cl)c1cc(N3CCN(C)CC3)ncc1N2] |
| 26 | 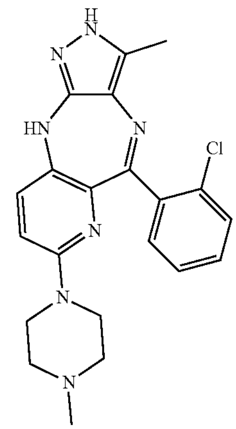 [SMILES: Cc1[nH]nc2c1N=C(c1ccccc1Cl)c1nc(N3CCN(C)CC3)ccc1N2] |
| 27 | 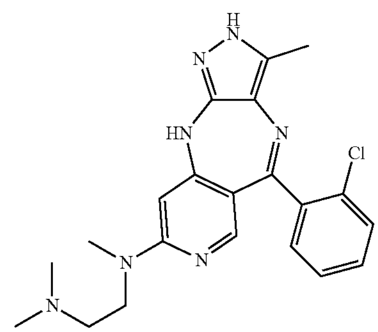 [SMILES: Cc1[nH]nc2c1N=C(c1ccccc1Cl)c1cnc(N(C)CCN(C)C)cc1N2] |
| 28 | 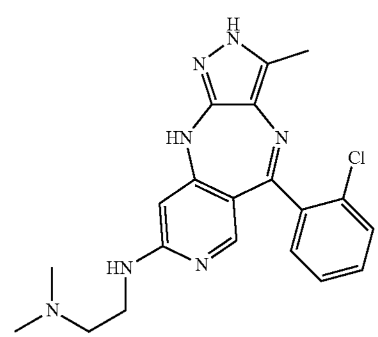 [SMILES: Cc1[nH]nc2c1N=C(c1ccccc1Cl)c1cnc(NCCN(C)C)cc1N2] |
| 29 | 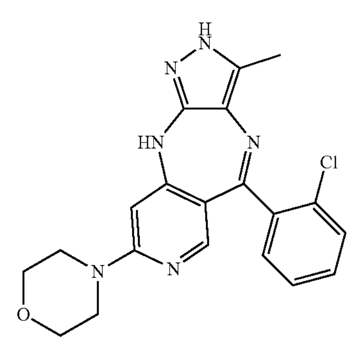 [SMILES: Cc1[nH]nc2c1N=C(c1ccccc1Cl)c1cnc(N3CCOCC3)cc1N2] |

TABLE 1-continued

| Number | Structure |
|---|---|
| 30 | |
| 31 | |
| 32 | |
| 33 | |
| 34 | 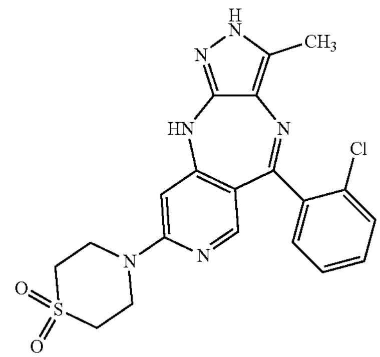 [SMILES: Cc1[nH]nc2c1N=C(c1ccccc1Cl)c1cnc(N3CCS(=O)(=O)CC3)cc1N2] |
| 35 | 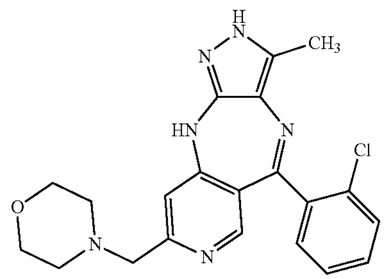 [SMILES: Cc1[nH]nc2c1N=C(c1ccccc1Cl)c1cnc(CN3CCOCC3)cc1N2] |
| 36 | 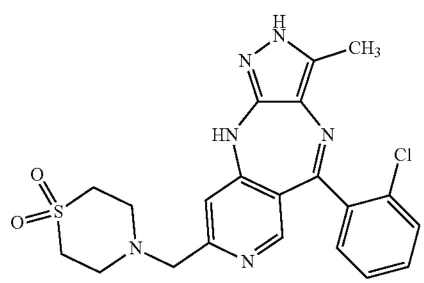 [SMILES: Cc1[nH]nc2c1N=C(c1ccccc1Cl)c1cnc(CN3CCS(=O)(=O)CC3)cc1N2] |
| 37 | 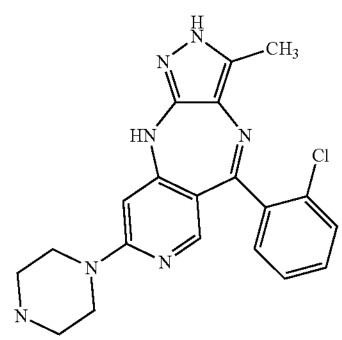 |
| 38 | 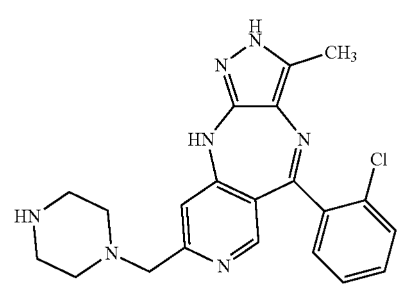 [SMILES: Cc1[nH]nc2c1N=C(c1ccccc1Cl)c1cnc(CN3CCNCC3)cc1N2] |

TABLE 1-continued

| Number | Structure |
|---|---|
| 39 | (structure) |
| 40 | (structure) |
| 41 | (structure) |
| 42 | (structure) |
| 43 | (structure) |
| 44 | (structure) |
| 45 | (structure) |
| 46 | (structure) |

TABLE 1-continued

| Number | Structure |
|---|---|
| 47 | 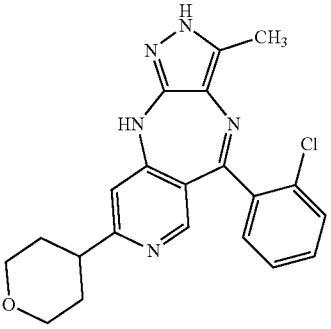 [SMILES: Cc1[nH]nc2c1N=C(c1ccccc1Cl)c1cnc(C3CCOCC3)cc1N2] |
| 48 | 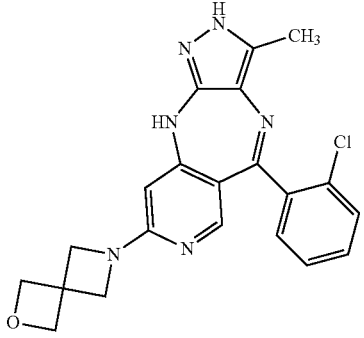 [SMILES: Cc1[nH]nc2c1N=C(c1ccccc1Cl)c1cnc(N3CC4(COC4)C3)cc1N2] |
| 49 | 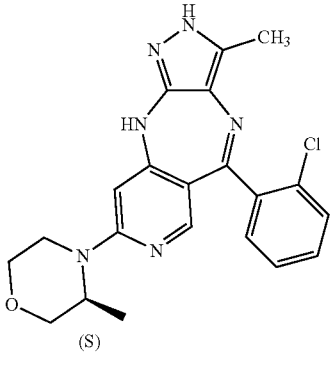 |
| 50 | 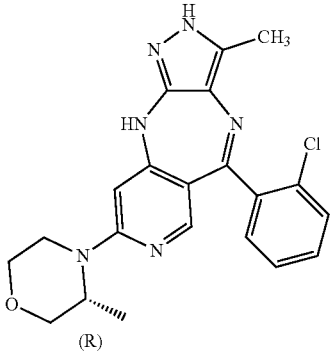 |

TABLE 1-continued

| Number | Structure |
|---|---|
| 51 | 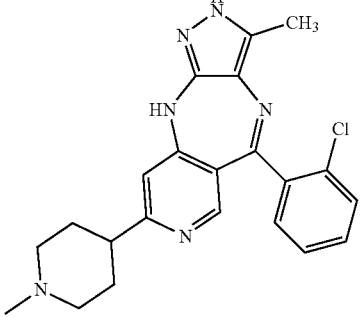 |

Since the crystal form of the compound differs greatly from other forms in terms of stability and solubility, the study of the crystal form is very important in the development of the drug. The present inventors studied a compound of formula (III) as follows and obtained a crystal form of the compound. Based on this, the present invention also provides a crystal form I of the compound of formula (III).

The crystal form I of the compound shown in formula (III), 4-(5-(2-chlorophenyl)-3-methyl-2,10-dihydropyrazolo[4,3-b]pyrido[4,3-e][1,4]diazepin-8-yl) morpholine, has characteristic peaks at 7.4±0.2°, 17.9±0.2°, 18.9±0.2°, 19.4±0.2°, 21.5±0.2° and 23.7±0.2° in the X-ray powder diffraction pattern. In a specific embodiment of the X-ray powder diffraction of the present invention, Cu-Kα radiation can be used, and the characteristic peaks are represented by 2θ angles;

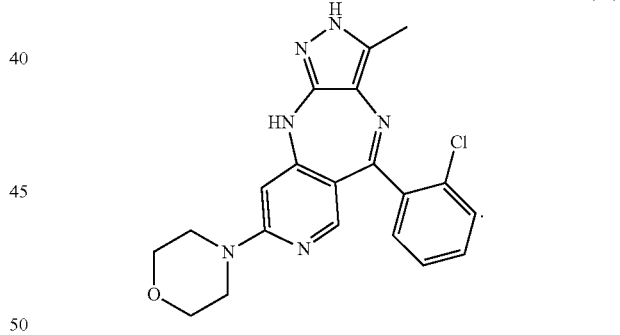

(III)

In one embodiment of the invention, in addition to the characteristic peaks described above, the crystal form I of the compound shown in formula (III) also has characteristic peaks at 14.0±0.2°, 15.0±0.2°, 20.7±0.2° and 25.4±0.2°.

In one embodiment of the invention, in addition to the characteristic peaks described above, the crystal form I of the compound shown in formula (III) also has characteristic peaks at 11.7±0.2°, 22.8±0.2°, and 27.8±0.2° represented by 2θ angle in the X-ray powder diffraction pattern.

The invention also provides a method for preparing the crystal form I of the compound of formula (III), which may comprise:

dissolving the compound shown in formula (III) in a single or mixed solvent with heating, and cooling to precipitate the crystal form I;

or
suspending the compound shown in formula (III) in a single or mixed solvent, stirring and filtering to obtain the crystal form I;
or
dissolving the compound of formula (III) in a single or mixed solvent, and concentrating under vacuum to obtain the crystal form I.

In one embodiment of the present invention, the single or mixed solvent used in the above method for preparing the crystal form I may be one or more selected from the group consisting of methanol, ethanol, tetrahydrofuran, 2-methyltetrahydrofuran, dichloromethane, dichloroethane, ethyl acetate, acetonitrile, dimethyl sulfoxide, dimethyl sulfoxide/water, methanol/tetrahydrofuran, methanol/2-methyltetrahydrofuran, methanol/dichloromethane, ethanol/2-methyltetrahydrofuran, and dichloromethane/water; preferably methanol, ethanol, tetrahydrofuran, 2-methyltetrahydrofuran, dimethyl sulfoxide, dimethyl sulfoxide/water, methanol/tetrahydrofuran, methanol/2-methyltetrahydrofuran, ethanol/2-methyltetrahydrofuran, and/or dichloromethane/water.

The "dimethyl sulfoxide/water" of the present invention means a mixture of dimethyl sulfoxide and water; "methanol/tetrahydrofuran" means a mixture of methanol and tetrahydrofuran; "methanol/2-methyltetrahydrofuran" means a mixture of methanol and 2-methyltetrahydrofuran, "methanol/dichloromethane" means a mixture of methanol and dichloromethane, "ethanol/2-methyltetrahydrofuran" means a mixture of ethanol and 2-methyltetrahydrofuran, and "dichloromethane/water" means a mixture of dichloromethane and water.

In one embodiment of the present invention, the aforementioned single or mixed solvent is used in an amount required to ensure the dissolution of all feeds, for example, the volume of the single or mixed solvent required for 1 g the compound shown in formula (III) is 90 mL to 200 mL.

The volume ratio of the mixed solvent to be used may be in the range of 0.1-20:1, preferably in the range of 1-10:1, and more preferably in the range of 1-5:1. For example, ethanol/2-methyltetrahydrofuran is 5:1, dichloromethane/water is 2:1, methanol/dichloromethane is 5:1, and the like.

The invention also provides a method for preparing the crystal form I of the compound shown in formula (III), which may comprise:
washing the compound shown in formula (III) with an appropriate amount of a single or mixed solvent, stirring, filtering (preferably filtering under a reduced pressure) and drying to obtain the crystal form I.

The single or mixed solvent is one or more selected from methanol, ethanol, tetrahydrofuran, 2-methyltetrahydrofuran, dichloromethane, dichloroethane, ethyl acetate, acetonitrile, dimethyl sulfoxide, dimethyl sulfoxide/water, methanol/tetrahydrofuran, methanol/2-methyltetrahydrofuran, methanol/dichloromethane, ethanol/2-methyltetrahydrofuran, dichloromethane/water; preferably methanol, ethanol, tetrahydrofuran, 2-methyltetrahydrofuran, dimethyl sulfoxide, dimethyl sulfoxide/water, methanol/tetrahydrofuran, methanol/2-methyltetrahydrofuran, ethanol/2-methyltetrahydrofuran, and/or dichloromethane/water.

The invention also provides a method for preparing the compound shown in formula (III), which comprises:
(1) reacting a compound shown in formula (III-A) with a compound shown in formula (III-B) to give a compound of formula (III-C);
(2) reacting the compound shown in formula (III-C) with a compound shown in formula (III-D) to give a compound of formula (III-E);
(3) deprotecting the compound shown in formula (III-E) to give a compound shown in formula (III-F) or (III-F') as a transition state;
(4) obtaining the compound shown in formula (III) from the compound shown in formula (III-F) or (III-F');

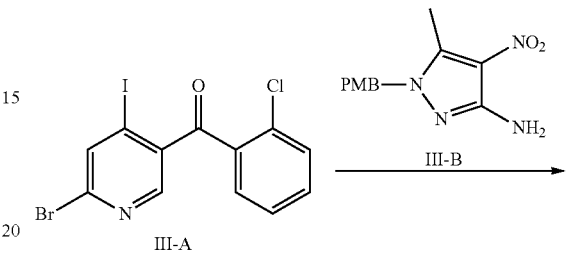

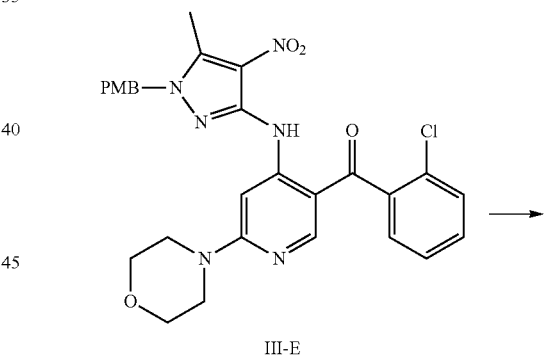

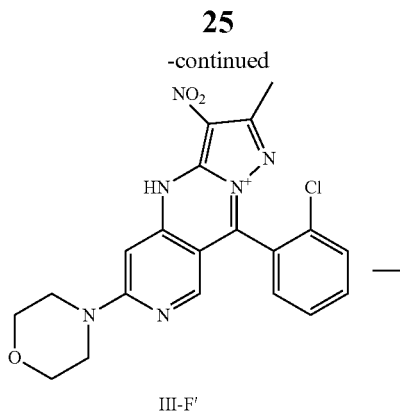

III-F'

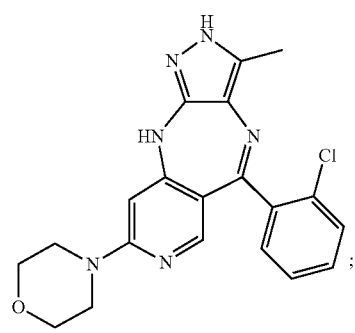

III wherein, the abbreviation "PMB" means p-methoxybenzyl.

The present invention also provides an intermediate for preparing the aforementioned compound of formula (III), which has the following structural formula:

(III-C)

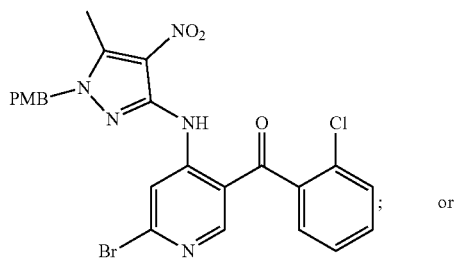

; or (III-E)

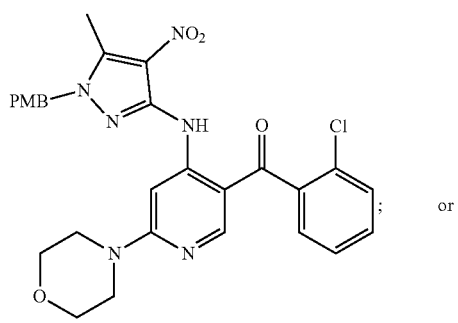

; or (III-F)

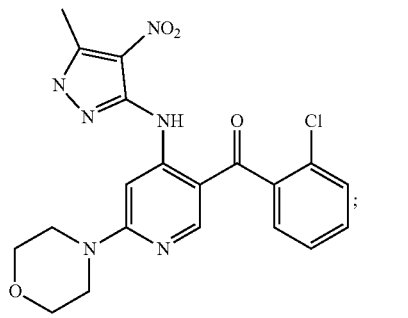

; or (III-F')

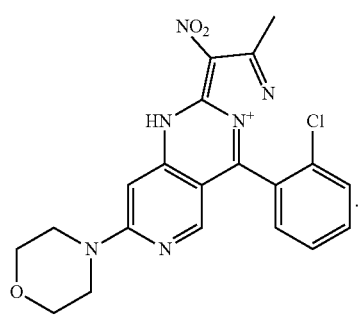

.

The invention also provides a pharmaceutical formulation comprising the aforementioned compounds of formula (I) or (II), pharmaceutically acceptable salts or stereoisomers thereof, and/or comprising the aforementioned crystal form I of the compound of formula (III).

In one embodiment of the invention, the pharmaceutical formulation may comprise one or more pharmaceutically acceptable carriers, and may be administered orally, parenterally, rectally or via pulmonary administration to a patient or subject in need thereof. For oral administration, the pharmaceutical composition can be formulated into a conventional solid formulation such as a tablet, a capsule, a pill, and a granule, etc.; or an oral liquid formulation such as an oral solution, an oral suspension, and a syrup, etc. A suitable filler, a binder, a disintegrating agent, a lubricant, or the like may be incorporated when preparing the oral formulation. For parenteral administration, the pharmaceutical composition can be formulated as an injection, including an injection liquid, a sterile powder for injection, and a concentrated solution for injection. When an injection is formulated, the formulation can be produced by a conventional method in the art of medicine. It is possible to formulate the injection with appropriate additional agents according to the drug properties, or without additional agents. For rectal administration, the pharmaceutical composition can be formulated as a suppository or the like. For pulmonary administration, the pharmaceutical composition can be formulated as an inhalant or a spray, etc.

In a specific embodiment of the present invention, the pharmaceutical formulation may further comprise one or more second therapeutic active agents, which are antimetabolites, growth factor inhibitors, mitosis inhibitors, antineoplastic hormones, alkylating agents, metals, topoisomerase inhibitors, hormone drugs, immunomodulators, tumor suppressor genes, cancer vaccines, immune checkpoints, or tumor immunotherapy-related antibodies or small molecular drugs.

The present invention also provides a pharmaceutical composition comprising the aforementioned compound of formula (I) or (II) or pharmaceutically acceptable salts or stereoisomers thereof, and/or a pharmaceutical composition comprising the aforementioned crystal form I of the compound of formula (III) and one or more second therapeutic active agents.

In one specific embodiment of the present invention, the composition may be used in a combined administration, in a "therapeutically effective amount", of the aforementioned compound of formula (I) or (II) or pharmaceutically acceptable salts or stereoisomers thereof, and/or the aforementioned crystal form I of the compound of formula (III), along with one or more second therapeutic active agents, such as sequential administration, simultaneous administration, alternatively, the therapeutically active ingredients are formulated into a compound formulation for administration.

The second therapeutic active agent is antimetabolite, growth factor inhibitor, mitosis inhibitors, antineoplastic hormones, alkylation agents, metals, topoisomerase inhibitors, hormone drugs, immunomodulators, tumor suppressor genes, cancer vaccines, immune checkpoints, or tumor immunotherapy-related antibodies or small molecular drugs.

The invention also provides use of the aforementioned compounds of formula (I) or (II) or pharmacologically acceptable salts or stereoisomers thereof, the aforementioned crystal form I of the compounds of formula (III), or the aforementioned pharmaceutical formulation in the manufacture of a medicament for treating multi-kinases mediated cancer, such as lung cancer, squamous cell carcinoma, bladder cancer, gastric cancer, ovarian cancer, peritoneal cancer, breast cancer, breast ductal carcinoma, head and neck cancer, endometrial carcinoma, uterine body cancer, rectal cancer, liver cancer, renal carcinoma, renal pelvic tumor, esophageal carcinoma, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin lymphoma, chorioadenoma of large intestine, melanoma, cytoma and sarcoma.

The invention also provides a method for treating diseases. The method comprises the administration in a therapeutically effective amount to patients in need of the aforementioned compound of the formula (I) or (II), or pharmacologically acceptable salts or stereoisomers thereof, the aforementioned crystal form I of the compound of formula (III), or the aforementioned pharmaceutical formulations. The diseases include multi-kinases mediated cancers, such as lung cancer, squamous cell carcinoma, bladder cancer, gastric cancer, ovarian cancer, peritoneal cancer, breast cancer, breast ductal carcinoma, head and neck cancer, endometrial carcinoma, uterine body cancer, rectal cancer, liver cancer, renal carcinoma, renal pelvic tumor, esophageal carcinoma, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin lymphoma, chorioadenoma of large intestine, melanoma, cytoma and sarcoma.

The "therapeutically effective amount" used herein refers to the amount of the aforementioned compound, crystal form I and/or pharmaceutical formulation that is capable of at least alleviating the symptoms of the condition in a patient when administered to the patient. The actual amount comprising a "therapeutically effective amount" will vary depending on a variety of circumstances including, but not limited to, the particular condition to be treated, the severity of the condition, the physique and health of the patient, and the route of administration. Skilled medical practitioners can readily determine the appropriate amount using the methods known in the art of medical treatment.

DETAILED DESCRIPTION OF THE INVENTION

The "halogen" as used in the present invention means fluorine, chlorine, bromine, iodine and the like, preferably fluorine and chlorine.

As used herein, "oxo" means that any C atom in the substituent can be oxidized to "—C(O)—"; if a hetero atom is contained, the hetero atom can form an oxide, e.g.,

can be oxidized into

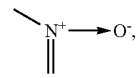

S can be optionally oxidized into S(O) or S(O)$_2$.

As used herein, "halogenated" means that any hydrogen atom in the substituent may be substituted with one or more halogens which are identical or different. "Halogen" is defined as above.

The "$C_{1-6}$ alkyl" as used in the present invention means a liner or branched alkyl group derived by removing one hydrogen atom from a hydrocarbon moiety having 1 to 6 carbon atoms, such as methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl and 1-methyl-2-methylpropyl, etc. The "$C_{1-4}$ alkyl" means the above examples having 1 to 4 carbon atoms.

The "$C_{2-8}$ alkenyl" as used in the present invention means a linear or branched alkenyl group derived by removing one hydrogen atom from an olefin moiety having 2 to 8 carbon atoms containing a carbon-carbon double bond, such as vinyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, and 1,4-hexadienyl, etc.

The "$C_{2-8}$ alkynyl group" of the present invention means a linear or branched alkyne group derived by removing one hydrogen atom from an alkyne moiety having 2 to 8 carbon atoms containing a carbon-carbon triple bond, such as ethynyl, propynyl, 2-butynyl, 2-pentynyl, 3-pentynyl, 4-methyl-2-pentynyl, 2-hexynyl, 3-hexynyl, etc. The "$C_{1-6}$ alkylcarbonylamino", "$C_{1-6}$ alkylaminocarbonyl", "$C_{1-6}$ alkylsulfonyl", "$C_{1-6}$ alkylcarbonyl", "$C_{1-6}$ alkylthio" of the present invention means $C_{1-6}$ alkyl-C(O)—NH—, $C_{1-6}$ alkyl-NH—C(O)—, $C_{1-6}$ alkyl-S(O)$_2$—, $C_{1-6}$ alkyl-C(O)—, $C_{1-6}$ alkyl-S—, respectively; the "$C_{1-6}$ alkyl" is as defined above, preferably "$C_{1-4}$ alkyl".

The "$C_{1-6}$ alkoxy" of the present invention means a group in which a "$C_{1-6}$ alkyl" as defined above is bonded to an oxygen atom, which is in turn bonded to a parent moiety, that is, "$C_{1-6}$ alkyl-O—" group, such as methoxy, ethoxy, propoxy, isopropoxy, n-butoxy, tert-butoxy, n-pentyloxy, neopentyloxy and n-hexyloxy, etc. The "$C_{1-4}$ alkoxy" refers to the above-mentioned examples having 1 to 4 carbon atoms, that is, "$C_{1-4}$ alkyl-O—" groups.

The "cycloalkyl", "aryl", "heterocyclyl" and "heteroaryl" of the present invention include a monocyclic system and a fused ring system (bicyclic system or polycyclic system).

Monocyclic system refers to a group in the form of only one ring, and fused ring system refers to a polycyclic ring structure formed by two or more cyclic structures connected in the form of ortho-fused, spiro or bridged rings. The ortho-fused ring refers to a fused ring structure formed by two or more cyclic structures sharing two adjacent ring atoms with each other (i.e., sharing one bond). The bridged ring refers to a fused ring structure formed by two or more cyclic structures sharing two non-adjacent ring atoms with each other. The spiro ring refers to a fused ring structure formed by two or more cyclic structures sharing one ring atom with each other. The cycloalkyl, aryl, heterocyclyl or heteroaryl defined by the number of atoms in the present invention include the monocyclic and the fused ring structures that can be formed, unless otherwise specified.

The "cycloalkyl" of the present invention means a monocyclic cycloalkyl, a bicyclic cycloalkyl system or a polycyclic cycloalkyl system. These groups may be saturated or unsaturated, but are not aromatic. The monocyclic cycloalkyl may be $C_{3-8}$ cycloalkyl, $C_{3-6}$ cycloalkyl, $C_{5-8}$ cycloalkyl, and the like. The examples of monocyclic cycloalkyl include, but are not limited to, cyclopropyl, cyclobutyl, cyclopentyl, cyclohexyl, cycloheptyl, cyclooctyl, cyclobutenyl, cyclopentenyl, cyclohexenyl, 1,4-cyclohexadienyl, cycloheptenyl, 1,4-cycloheptadienyl, cyclooctenyl, 1,5-cyclooctadienyl and the like. The ortho-fused cycloalkyl may be 6-12 membered ortho-fused cycloalkyl, 7-10 membered ortho-fused cycloalkyl, and the typical examples thereof include, but are not limited to, bicyclic[3.1.1]heptane, bicyclic[2.2.1]heptane, bicyclic[2.2.2]octane, bicyclic[3.2.2]nonane, bicyclic[3.3.1]nonane and bicyclic[4.2.1] nonane. The spirocyclic cycloalkyl may be 6-12 membered spirocyclic groups, 7-11 membered spirocyclic groups or the like, and the examples thereof include, but are not limited to,

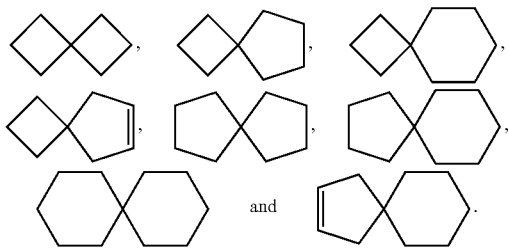

The bridged cycloalkyl may be 6-12 membered bridged ring groups and 7-11 membered bridged ring groups, and the examples thereof include, but are not limited to:

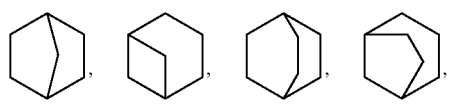

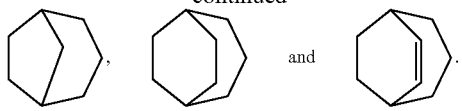

The "3-14 membered cycloalkyl", "3-10 membered cycloalkyl", and "3-6 membered cycloalkyl" of the present invention include monocyclic and fused ring structures that can be formed, unless otherwise specified.

The "heterocyclyl" of the present invention means a non-aromatic cyclic group in which at least one ring carbon atom is substituted with a hetero atom selected from O, S and N, preferably substituted with 1-3 hetero atoms, and wherein a carbon atom, a nitrogen atom and a sulfur atom can be oxidized.

"Heterocyclyl" means monocyclic heterocyclyl, bicyclic heterocyclyl or polycyclic heterocyclyl system, including saturated, partially saturated heterocyclyl, but excluding aromatic rings. The monoheterocyclyl may be 3-8 membered heterocyclyl, 3-8 membered saturated heterocyclyl, 3-6 membered heterocyclyl, 4-7 membered heterocyclyl, 5-7 membered heterocyclyl, 5-6 membered heterocyclyl, 5-6 membered oxygen-containing heterocyclyl, 5-6 membered nitrogen-containing heterocyclyl, 5-6 membered saturated heterocyclyl or the like. Examples of monoheterocyclyl include, but are not limited to, aziridinyl, oxiranyl, thiiranyl, azetidinyl, oxetanyl, thietanyl, tetrahydrofuranyl, tetrahydropyrrolyl, tetrahydrothiophenyl, imidazolidinyl, pyrazolidinyl, 1,2-oxazolidinyl, 1,3-oxazolidinyl, 1,2-thiazolidinyl, 1,3-thiazolidinyl, tetrahydro-2H-pyranyl, tetrahydro-2H-thiopyranyl, piperidinyl, piperazinyl, morpholinyl, 1,4-dioxanyl, 1,4-thioxanyl; the examples of partially saturated heterocyclyl include, but are not limited to, 4,5-dihydroisooxazolyl, 4,5-dihydrooxazolyl, 2,5-dihydrooxazolyl, 2,3-dihydrooxazolyl, 3,4-dihydro-2H-pyrrolyl, 2,3-dihydro-1H-pyrrolyl, 2,5-dihydro-1H-imidazolyl, 4,5-dihydro-1H-imidazolyl, 4,5-dihydro-1H-pyrazolyl, 4,5-dihydrogen-3H-pyrazolyl, 4,5-dihydrothiazolyl, 2,5-dihydrothiazolyl, 2H-pyranyl, 4H-pyranyl, 2H-thiopyranyl, 4H-thiopyranyl, 2,3,4,5-tetrahydropyridyl, 1,2-isooxazinyl, 1,4-isooxazinyl, or 6H-1,3-oxazinyl and the like. The fused heterocyclic ring includes ortho-fused heterocyclyl, spiroheterocyclyl, bridged heterocyclyl, and may be saturated, partially saturated or unsaturated, but not aromatic. The fused heterocyclyl is 5- or 6-membered monocyclic heterocyclic ring fused to benzene ring, i.e. 5- or 6-membered monocyclic cycloalkyl, 5- or 6-membered monocyclic cycloalkenyl, 5- or 6-membered monocyclic heterocyclyl, or 5- or 6-membered monocyclic heteroaryl. The ortho-fused heterocyclyl can be 6-12 membered ortho-fused heterocyclyl, 7-11 membered ortho-fused heterocyclyl, 6-10 membered ortho-fused heterocyclyl, 6-12 membered saturated ortho-fused heterocyclyl, and 7-11 membered saturated ortho-fused heterocyclyl, and the examples thereof include, but are not limited to, 3-azabicyclo[3.10.]hexyl, 3,6-diazabicyclo[3.2.0]heptyl, 3,8-diazabicyclo[4.2.0]octyl, 3,7-diazabicyclo[4.2.0]octyl, octahydropyrrolo[3,4-c]pyrrolyl, octahydropyrrolo[3,4-b]pyrrolyl, octahydropyrrolo[3,4-b][1,4]oxazinyl, octahydro-1H-pyrrolo[3,4-c]pyridinyl, 2,3-dihydrobenzofuran-2-yl, 2,3-dihydrobenzofuranyl-3-yl, indolin-1-yl, indolin-2-yl, indolin-3-yl, 2,3-dihydrobenzothiophen-2-yl, octahydro-1H-indolyl, octahydrobenzofuranyl.

The spiroheterocyclyl may be 6-12 membered spiroheterocyclyl, 7-11 membered spiroheterocyclyl, 7-11 membered saturated spiroheterocyclyl 6-12 membered saturated spirocyclyl, and the examples thereof include not limited to:

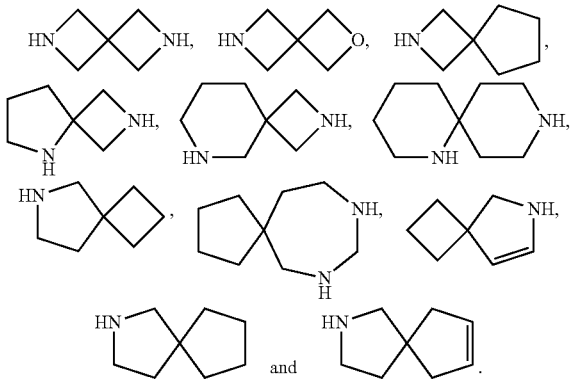

The bridged heterocyclyl may be 6-12 membered bridged heterocyclyl, 7-11 membered bridged heterocyclyl, 6-12 membered saturated bridged heterocyclyl, and 7-11 membered saturated bridged heterocyclyl, and the examples thereof include but limited to:

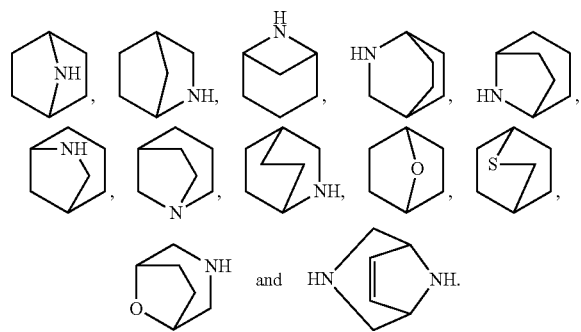

The 5-14 membered heterocyclyl, 5-11 membered heterocyclyl, 5-10 membered heterocyclyl, 6-10 membered heterocyclyl, 7-11 membered heterocyclyl, 7-11 member saturated heterocyclyl of the present invention include monocyclic and fused ring structures that can be formed, unless otherwise specified.

The aryl of the present invention refers to an aromatic cyclic group, including a monocyclic system, a bicyclic system or a polycyclic system, and may be 6-14 membered aryl, including "6-8 membered monocyclic aryl", for example, phenyl, cyclooctenyl, etc.; and "8-14 membered fused ring aryl", such as pentalenyl, naphthyl, phenanthryl, and the like.

The term "heteroaryl" as used herein refers to an aromatic cyclic group in which at least one ring carbon atom is substituted with a heteroatom selected from O, S and N, preferably 1 to 3 heteroatoms, including the condition that a carbon atom or a sulfur atom is oxidized, for example, the carbon atom is substituted by C(O), S(O), S(O)$_2$. Heteroaryl includes monocyclic heteroaryl and fused heteroaryl, which may be 5-14 membered heteroaryl, 5-10 membered heteroaryl, 5-7 membered heteroaryl, 5-6 membered heteroaryl, 8-10 membered heteroaryl. The representative examples of monocyclic heteroaryl include, but are not limited to, furanyl, imidazolyl, isoxazolyl, thiazolyl, isothiazolyl, oxadiazolyl, oxazolyl, isoxazolyl, pyridyl, pyridazinyl, pyrimidinyl, pyrazinyl, pyrazolyl, pyrrolyl, tetrazolyl, thiadiazolyl, thiazolyl, thienyl, triazolyl and triazinyl. Fused heteroaryl refers to bicyclic or polycyclic ring system fused to phenyl, cycloalkyl, cycloalkenyl, heterocyclyl or heteroaryl. The fused heteroaryl may be 8-12 membered heteroaryl, 8-10 membered heteroaryl, 9-10 membered heteroaryl. The representative examples of fused heteroaryl include, but are not limited to, benzimidazolyl, benzofuranyl, benzothienyl, benzothienyl, benzooxadiazolyl, benzothiazolyl, cinnolinyl, 5,6-dihydroquinolin-2-yl, 5,6-dihydroisoquinolin-1-yl, indazolyl, indolyl, isoquinolyl, naphthyridinyl, purinyl, quinolyl, 5,6,7,8-tetrahydroquinol-2-yl, 5,6,7,8-tetrahydroquinolyl, 5,6,7,8-tetrahydroquinol-4-yl, 5,6,7,8-tetrahydroisoquinol-1-yl, 4,5,6,7-tetrahydro[c][1,2,5]oxadiazole and 6,7-dihydro[c][1,2,5]oxadiazole-4(5H) keto. In certain embodiments, the fused heteroaryl is 5- or 6-membered monocyclic heteroaryl ring fused to phenyl ring, i.e. 5- or 6-membered monocyclic cycloalkyl, 5- or 6-membered monocyclic cycloalkenyl, 5- or 6-membered monocyclic heterocyclyl, or a 5- or 6-membered monocyclic heteroaryl.

The 5-14 membered heteroaryl, 5-10 membered heteroaryl, 6-10 membered heteroaryl, 5-6 membered heteroaryl, and 8-10 membered heteroaryl of the present invention include the monocyclic and fused ring structures that can be formed, unless otherwise specified.

The "pharmaceutically acceptable salts" as used herein means pharmaceutically acceptable addition salts and solvates of acids and bases. Such pharmaceutically acceptable salts include salts of the following acids: such as hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, alkanoic acid (such as acetic acid, HOOC—(CH$_2$)$_n$—COOH (where n is 0 to 4)), and the like. Such pharmaceutically acceptable salts also include salts of the bases such as sodium, potassium, calcium, ammonium and the like. A variety of non-toxic pharmaceutically acceptable addition salts are known to those skilled in the art.

The "stereoisomer" of the compounds of formula (I) or (II) of the present invention means an enantiomer in the case that the compound of formula (I) or (II) has an asymmetric carbon atom; a cis-trans isomer in the case that the compound has a carbon-carbon double bond or a cyclic structure; tautomers in the case that a ketone or oxime is present in the compound. The enantiomers, diastereomers, racemic isomers, cis-trans isomers, tautomers, geometric isomers, epimers and mixtures thereof of the compounds of formula (I) or (II) are all included within the scope of the invention.

The beneficial effects of the invention:

(1) The compounds of formula (I) or (II) and the crystal form I of the compound of formula (III) of the present invention are dual inhibitors against mitosis and angiogenesis.

(2) The drugs are more effective via coordination of multi-kinases, and shows better pharmacological activities such as enzymology, cytology and pharmacodynamics, etc.

(3) The compound of the present invention has better pharmacokinetic properties, physicochemical properties and/or toxicological properties, as well as druggability.

BRIEF DESCRIPTION OF THE DRAWINGS

In order to illustrate the embodiments of the present invention and the technical solutions of the prior art more clearly, the drawings used in the embodiments and the prior art are briefly introduced below. Obviously, the drawings in the following description are only some embodiments of the present invention, and those skilled in the art can obtain other drawings according to the drawings without any creative work.

EMBODIMENTS

Figure 1:
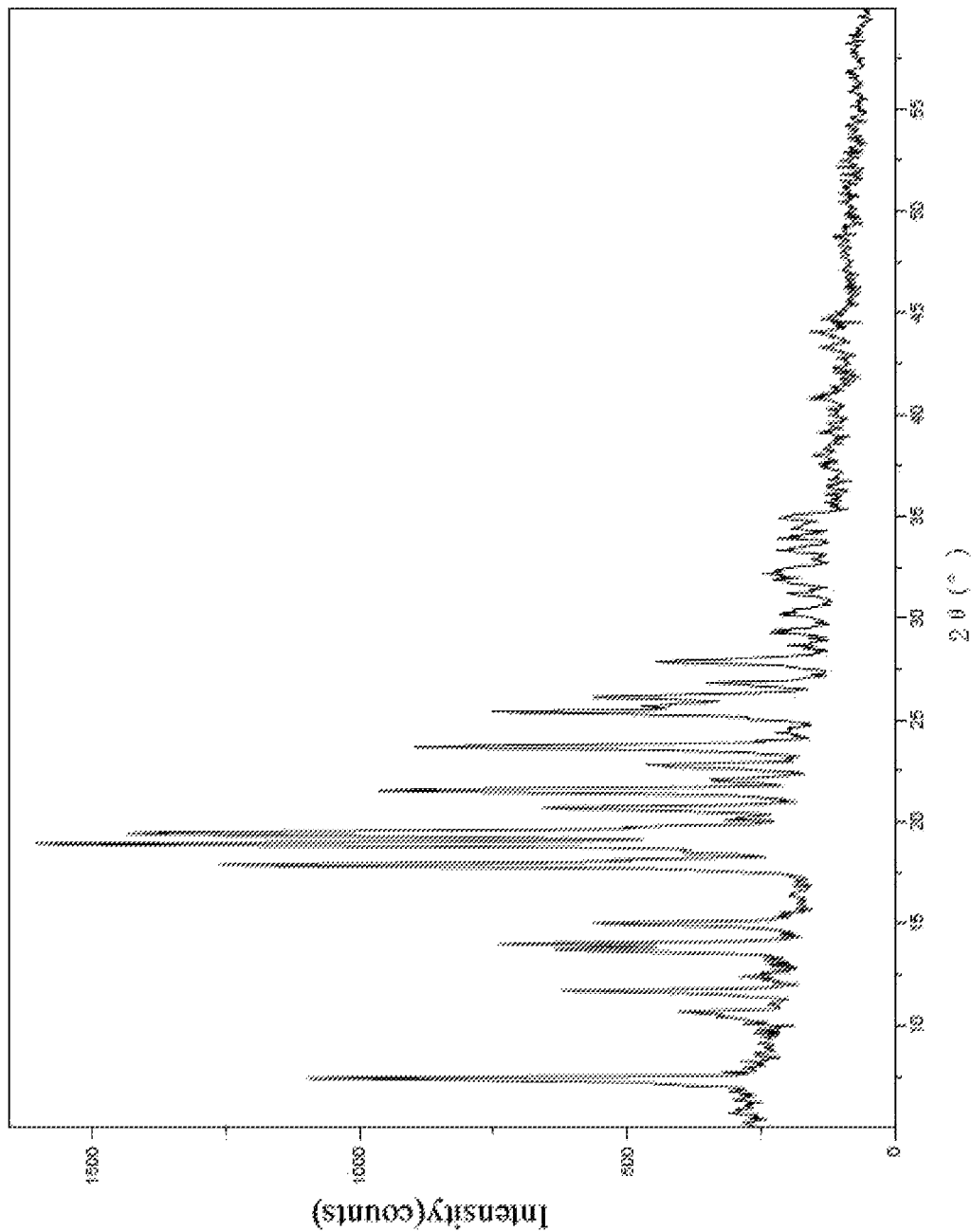
FIG. 1 is an X-ray powder diffraction (XRPD) pattern of the crystal form I of the compound of formula (III).

The present invention will be further described in detail below with reference to the accompanying drawings, so as to illustrate the purposes, technical solutions and advantages of the present invention more clearly. It is apparent that the described embodiments are only a part of the embodiments of the invention, rather than all of them. All other embodiments obtained by those skilled in the art based on the embodiments of the present invention without creative efforts are within the scope of the present invention.

Preparation Example 1: Synthesis of an Intermediate 1-(4-methoxybenzyl)-5-methyl-4-nitro-1H-pyrazol-3-amine

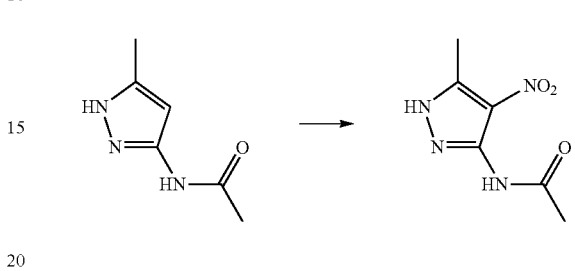

Step 1: Synthesis of
N-(5-methyl-H-pyrazol-3-yl)acetamide

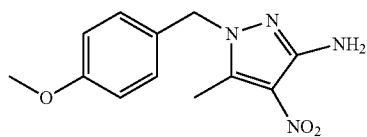 [SMILES: COc1ccc(Cn2nc(N)c([N+](=O)[O-])c2C)cc1]

5-methyl-1H-pyrazol-3-amine (300 g, 3.09 mol, 1.0 eq) was weighted into a 5 L round bottom flask, dissolved by adding water (2800 mL) with mechanical stirring at room temperature. Sodium bicarbonate (780 g, 9.28 mol, 3 eq) was added in portions, following by stirring for another 30 min after the addition. Then, acetic anhydride (592 ml, 6.2 mol, 2 eq) was added dropwise and slowly to the reaction system over about 1 h at controlled drop rate. At this point, a large amount of foamy white solid was produced. The temperature was raised to 100° C. and the reaction system was stirred for 2 h. The solid was gradually dissolved, and the system became clarification. Then heating was stopped, and the system was cooled to room temperature. After stirring overnight, a large amount of white crystalline solid precipitated. Another batch of 5-methyl-1H-pyrazol-3-amine (300 g) was fed in a parallel reaction. After the reactions were completed, the two batches were combined and filtered, and the solid was washed with water (500 mL×2) and dried to give a white solid (554 g, yield 62%).

$^1$H NMR (400 MHz, DMSO-d$_6$) δ (ppm): 10.32 (s, 1H), 6.21 (s, 1H), 2.18 (s, 3H), 1.97 (s, 3H).

Step 2: Synthesis of
N-(5-methyl-4-nitro-1H-pyrazol-3-yl)acetamide

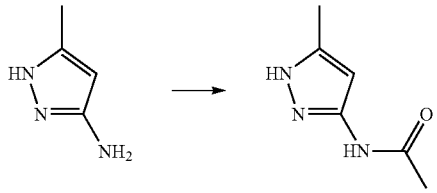

Concentrated sulfuric acid (2 L, about 36.8 mol, 9.2 eq) was charged into a 5 L round bottom flask, and added N-(5-methyl-1H-pyrazol-3-yl)acetamide (554 g, 3.98 mol, 1 eq) in portions over 1 h with mechanical stirring in the presence of an ice water bath. Stirring was continued until the solid was completely dissolved. Then fuming nitric acid (250 mL, about 5.7 mol, 1.4 eq) was added to the system over 2 h at a controlled temperature of less than 15° C. The reaction endpoint was monitored by LC-MS after the reaction was continued for another 15 min. A large amount of white solid was precipitated immediately upon the reaction system was slowly poured into 5 L of crushed ice water with mechanical stirring. The mixture was allowed to stand overnight and filtered. The solid obtained was washed with water (1000 mL×2), to obtain a white solid (587 g, yield 80%) after infrared drying.

$^1$H NMR (400 MHz, DMSO-d$_6$) δ (ppm): 10.22 (s, 1H), 2.44 (s, 1H), 2.13 (s, 3H).

Step 3: Synthesis of
5-methyl-4-nitro-1H-pyrazole-3-amine

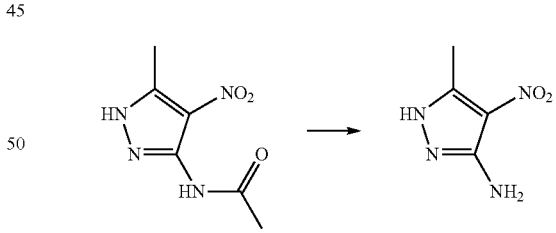

Water (1.1 L) and concentrated hydrochloric acid (1 L, about 12 mol, 4 eq) were charged to a 5 L four-neck round bottom flask, and gradually heated to 80° C. N-(5-methyl-4-nitro-1H-pyrazol-3-yl) acetamide (587 g, 3 mol, 1 eq) was added in portions over about 1 h with mechanical stirring. The mixture was continued to reflux at 100° C. for about 1 h until the system was clarified. The mixture was filtered after cooling to remove the insoluble matter. The filtrate was concentrated under reduced pressure to get crude product, which was pulped with methyl tert-butyl ether and filtered. The cake obtained was dried to give an orange solid (610 g crude product).

Step 4: Synthesis of 1-(4-methoxybenzyl)-5-methyl-4-nitro-1H-pyrazol-3-amine

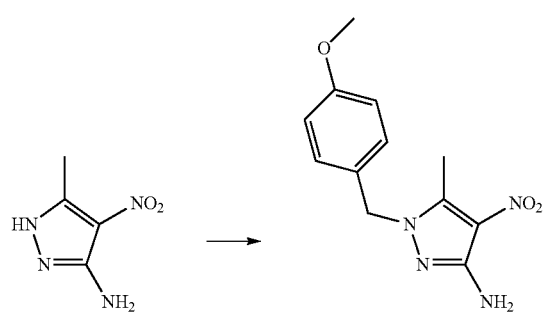

5-methyl-4-nitro-1H-pyrazol-3-amine hydrochloride (200 g, 1.12 mol, 1 eq) was charged into a 3 L round bottom flask, dissolved by adding DMF (1.8 L) with mechanical stirring at room temperature, added potassium carbonate (335 g, 2.42 mol, 2.1 eq) slowly in portions over about 40 minutes, and then added 4-methoxybenzyl chloride (177 g, 1.13 mol, 1 eq) dropwise over 30 min. The reaction system was stirred at room temperature overnight. It is detected by TLC and LC-MS that a small amount of starting material was remained. Another two batches of 5-methyl-4-nitro-1H-pyrazole-3-amine hydrochloride (200 g, 1.12 mol) were fed in parallel reactions. After the reactions were completed, the mixtures were filtered. The filtrates were combined, concentrated under reduced pressure to a half of the solvent remained, poured into ice water (about 2.5 L) with stirring to precipitate brownish yellow solid, and allowed to stand overnight. The filter cake was washed with DCM (1000 mL×3), concentrated under reduced pressure, poured into ice water (about 1000 mL) to precipitate a brownish yellow solid, and allowed to stand overnight. The solid precipitated above was combined, washed with water (500 mL×2). After drying under vacuum, the solid was pulped with ethyl acetate, filtered and dried to give a yellow solid (268 g, yield 30%).

$^1$H NMR (400 MHz, DMSO-$d_6$) δ (ppm): 7.18 (d, J=8.6 Hz, 2H), 6.90 (d, J=8.6 Hz, 2H), 6.18 (s, 2H), 5.09 (s, 2H), 3.73 (s, 3H), 2.56 (s, 3H).

Preparation Example 2: Synthesis of an Intermediate (6-bromo-4-iodo-pyridin-3-yl)(2-chlorophenyl)methanone

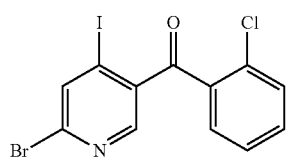 [SMILES: O=C(c1ccccc1Cl)c1cnc(Br)cc1I]

Step 1: Synthesis of (6-bromopyridin-3-yl)(2-chlorophenyl)methanol

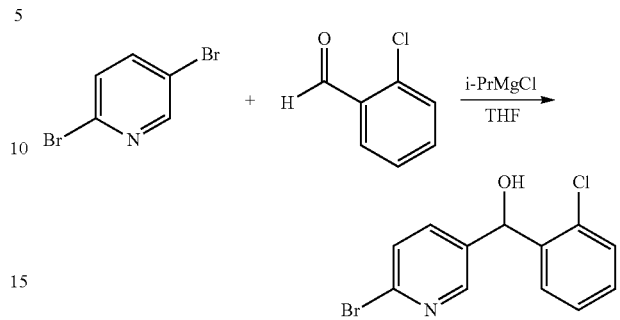

Anhydrous tetrahydrofuran (500 mL) and 2,5-dibromopyridine (100.0 g, 0.42 mol, 1.0 eq) were added into a 2 L four-necked flask, and the mixture was cooled to 2° C. with stirring in the presence of an ice water bath. Isopropyl magnesium chloride (210.5 mL, 2.0 M, 0.42 mol, 1.0 eq) was then added dropwise over about 0.5 h at a controlled temperature of no more than 10° C. The reaction system was stirred at room temperature (20° C.) for 1 h, then cooled to 10° C. with an ice water bath. A solution of 2-chlorobenzaldehyde (62.3 g, 0.443 mol, 1.05 eq) in tetrahydrofuran (200 mL) was added dropwise over about 0.5 h. After stirring at 10° C. for 2 h, the reaction endpoint was monitored by TLC. Saturated aqueous solution of ammonium chloride (300 mL) was added into the reaction system. After stirring for 10 min, the organic phase was separated from the mixture and concentrated to yellow oil. The aqueous phase was extracted with EtOAc (1.0 L×2). The resultant then was combined with the yellow oil obtained above, washed with water (500 mL) followed by saturated brine (500 mL), dried over anhydrous $Na_2SO_4$, and concentrated to give a brown oil (140 g crude product).

Step 2: Synthesis of (6-bromopyridin-3-yl)(2-chlorophenyl)methanone

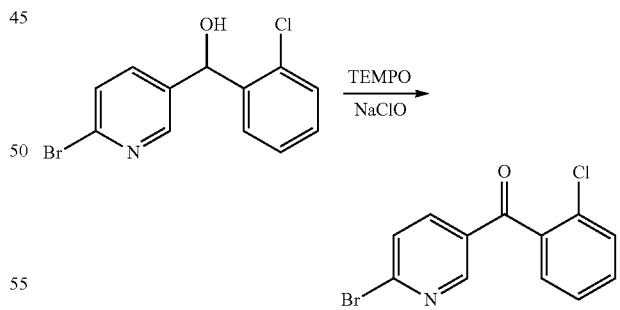

(6-bromopyridine-3-yl)(2-chlorophenyl)methanol (140 g crude product) was added into DCM (1.3 L), then added TEMPO (1.51 g, 9.4 mmol) and NaBr (1.92 g, 18.8 mmol). The reaction system was cooled to 3° C. in the presence of an ice-water bath, and added dropwise an aqueous solution of NaClO (1.34 mol/L, 600 L, 0.71 mol) neutralized with $NaHCO_3$ (45.0 g) at a temperature of no more than 20° C. After the completion of the addition, the reaction was stirred for 10 min, and then the reaction endpoint was monitored by TLC. The aqueous phase separated from the reaction mixture was extracted with DCM (1.0 L). The organic phases was combined, washed with water (1.0 L) followed by saturated brine (1.0 L), and dried over anhydrous Na$_2$SO$_4$. Yellow oil was obtained after concentration, pulped with 150 mL methyl tert-butyl ether/500 mL petroleum ether to obtain a yellow solid (50.3 g, yield: 39.7% for two steps).

Step 3: Synthesis of (6-bromo-4-iodo-pyridin-3-yl) (2-chlorophenyl)methanone

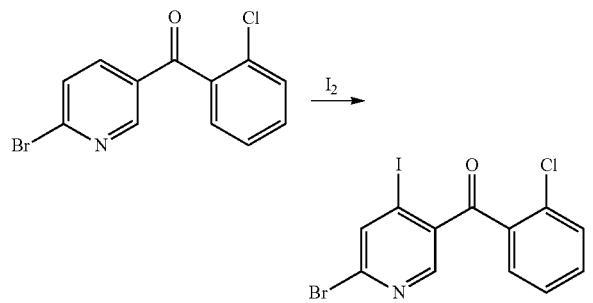

Under nitrogen atmosphere, tetramethylpiperidine lithium/magnesium chloride solution (281 mL, 1.5 mol/L, 0.43 mol, 2.5 eq) was added into a 2 L four-necked flask, and cooled to −65° C. in the presence of a dry ice/ethanol bath. A solution of (6-bromopyridin-3-yl) (2-chlorophenyl) methanone (50.0 g, 0.17 mol, 1.0 eq) in tetrahydrofuran (50 mL) was added dropwise over about 0.5 h. Then, the reaction mixture was heated to −45° C. under stirring for 1 h, and then cooled to −65° C. again. A solution of I$_2$ (129.3 g, 0.51 mol, 3.0 eq) in tetrahydrofuran (400 mL) was added dropwise over about 1 h. The reaction system was stirred for 20 min, and the reaction endpoint was monitored by TLC. Then, Added a saturated aqueous solution of ammonium chloride (500 mL) and a saturated aqueous solution of NaHSO$_3$ (500 mL) to the reaction system, and stirred for 15 minutes, then filtered. The insoluble matters were washed with ethyl acetate (500 mL×2). The filtrates were combined. The aqueous phase separated out was extracted with EtOAc (1.0 L×2). All organic phases were combined, washed with water (800 mL) followed by saturated brine (800 mL), dried over anhydrous Na$_2$SO$_4$, and concentrated to obtain an yellow solid. The yellow solid was pulped with methyl tert-butyl ether (500 mL)/petroleum ether (500 mL) and dried to give a yellow solid (30 g, yield: 41.8%).

1H NMR (400 MHz, CDCl$_3$) δ (ppm): 7.38-7.50 (m, 2H), 7.51-7.65 (m, 2H), 8.17 (s, 1H), 8.24 (s, 1H).

Preparation Example 3: Synthesis of an Intermediate (6-bromo-4-((1-(4-methoxybenzyl)-5-methyl-4-nitro-1H-pyrazol-3-yl)amino)pyridin-3-yl)(2-chlorophenyl)methanone

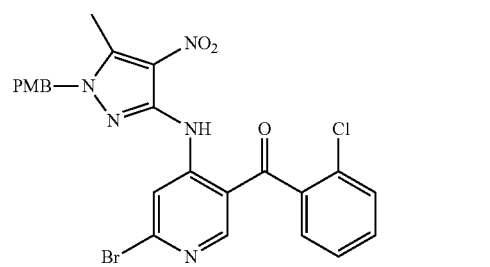

Step 1: Synthesis of (6-bromo-4-((1-(4-methoxybenzyl)-5-methyl-4-nitro-1H-pyrazol-3-yl)amino) pyridin-3-yl) (2-chlorophenyl)methanone

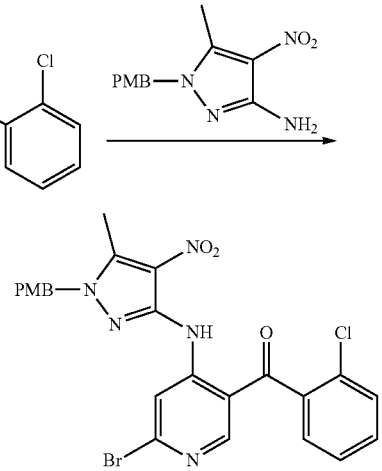

1-(4-methoxybenzyl)-5-methyl-4-nitro-1H-pyrazol-3-amine (14.92 g, 56.9 mmol) was added into anhydrous tetrahydrofuran (100 mL), dissolved with stirring under nitrogen. NaH (40% by mass, 4.82 g, 0.11 mol) was added in batches under ice bath, and stirred for 1 hour after the addition, then added dropwise with a solution of (6-bromo-4-iodo-pyridin-3-yl) (2-chlorophenyl)methanone (20 g, 47.4 mmol) in tetrahydrofuran (100 mL). The reaction was performed for 16 h at room temperature. The reaction endpoint was monitored by TLC. Methanol (30 mL) was added to quench the reaction, followed by saturated ammonium chloride solution (50 mL). The mixture obtained was filtrated to obtain a yellow product (25 g, yield 80%).

$^1$H-NMR (400 MHz, DMSO-d$_6$): 12.36 (s, 1H), 8.77 (s, 1H), 8.11 (s, 1H), 7.66-7.53 (m, 4H), 7.33 (d, J=8.8 Hz, 1H), 7.33 (d, J=8.8 Hz, 1H), 6.96 (d, J=8.8 Hz, 1H), 5.39 (s, 2H), 3.75 (s, 3H), 2.73 (s, 3H).

Example 1: Synthesis of Compound 1

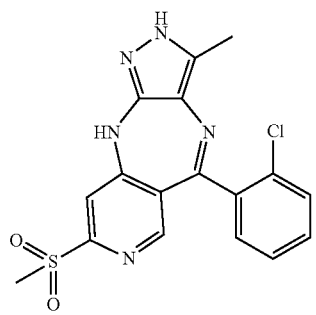

Compound 1

Synthetic Route:
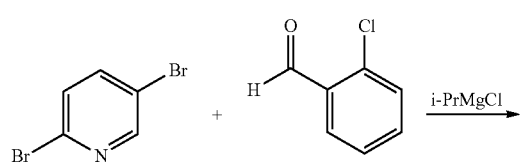
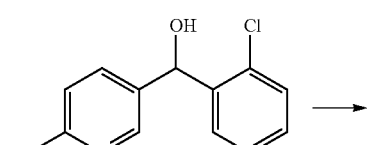
1-1
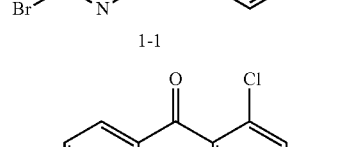
1-2
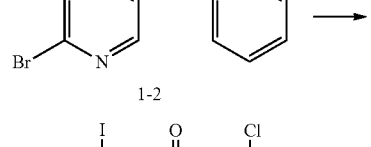
1-3
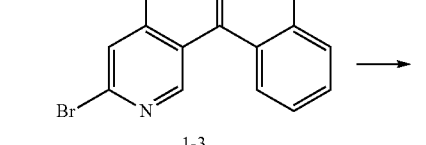
1-4
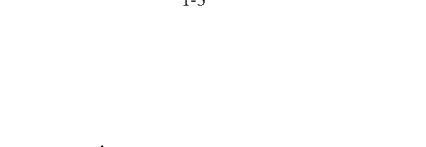
1-5
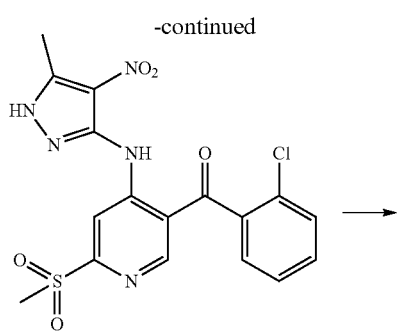
1-6
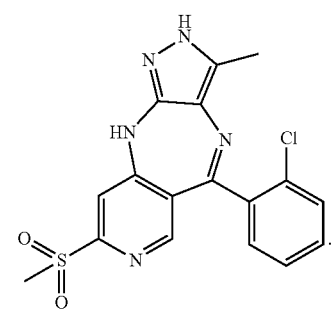
Compound 1
Step 1: Intermediate 1-3 was Prepared According to the Method in Preparation Example 2
Step 2: Intermediate 1-4 was Prepared According to the Method in Preparation Example 3
Step 3: Synthesis of Intermediate 1-5
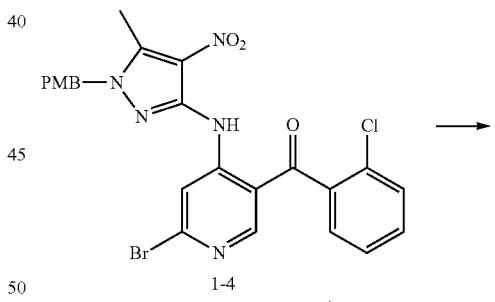
1-4
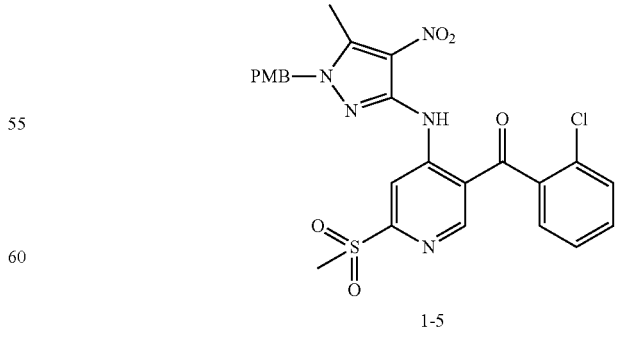
1-5
Intermediate 1-4 (5 g, 9 mmol) was added in cuprous iodide (5.13 g, 27 mmol) and sodium methanesulfinate (2.76 g, 27 mmol). Then DMSO (100 mL) was injected after the reactor was replaced with nitrogen three times. The reaction system was heated to 130° C., and reacted for 5 h. The reaction endpoint was monitored by TLC. The crude product was purified by silica gel column chromatography (eluted with dichloromethane) to give 1.1 g yellow solid, with a yield of 23%.

Step 4: Synthesis of Intermediate 1-6

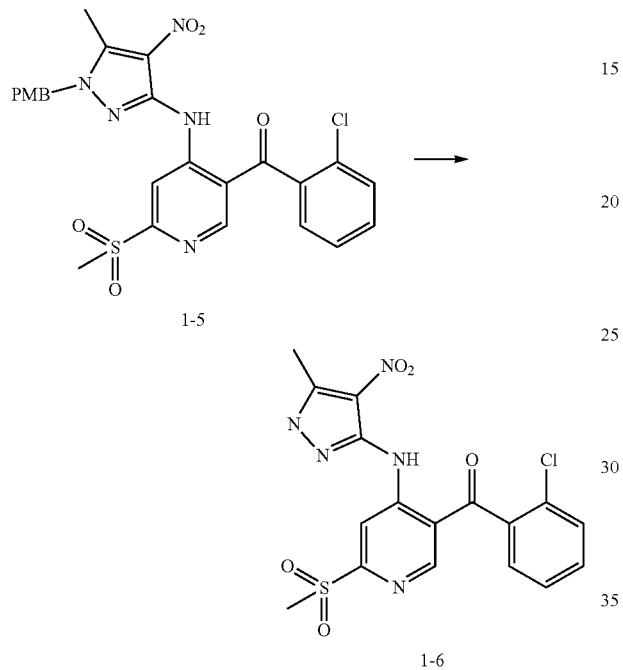

Intermediate 1-5 (1.1 g, 2.0 mmol) was added in dichloromethane (3 mL) and dissolved.

Trifluoroacetic acid (10 mL) was slowly added dropwise. The mixture was heated to 70° C., and reacted for 8 h. LC-MS showed the reaction endpoint. Solvent and trifluoroacetic acid were rotary evaporated to give 1.5 g brown solid, which was directly used for the next step.

Step 5: Synthesis of Compound 1

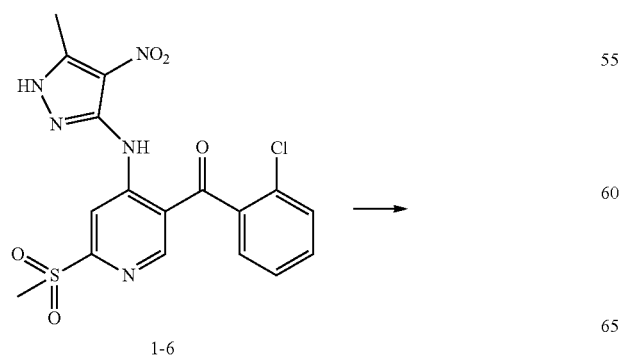

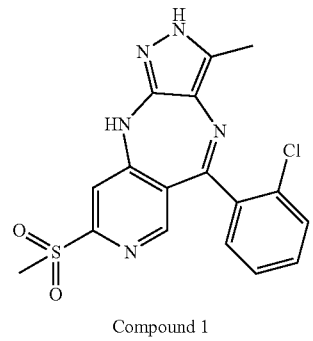

Compound 1

Intermediate 1-6 (1.5 g, 3.4 mmol) was added in 2-methyltetrahydrofuran (15 mL) and dissolved. Tin dichloride dihydrate (5.4 g, 24.1 mmol) was added under nitrogen atmosphere. The mixture was heated to 100° C., and reacted for 16 h. LC-MS showed the reaction endpoint. The mixture was adjusted to pH=10 by adding sodium hydroxide aqueous solution, and was filtered with celite. The filtrate was extracted with 2-methyltetrahydrofuran, and concentrated. The crude product was purified by silica gel column chromatography (EA:DCM=1:3) to obtain compound 1 as a yellow solid (60 mg, yield 10%).

$^1$H NMR (400 MHz, CDCl$_3$) δ: 11.84 (s, 1H), 9.12 (s, 1H), 7.43-7.51 (m, 4H), 7.17 (s, 1H), 7.11 (s, 1H), 3.11 (s, 3H), 1.96 (s, 3H).

Example 2: Synthesis of Compound 2

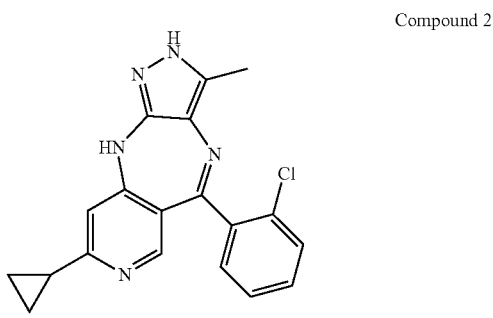 [SMILES: Cc1[nH]nc2c1N=C(c1ccccc1Cl)c1cnc(C3CC3)cc1N2]

Compound 2

Step 1: Synthesis of Intermediate 2-1

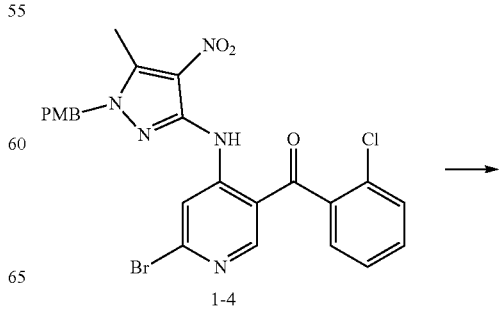

43

-continued

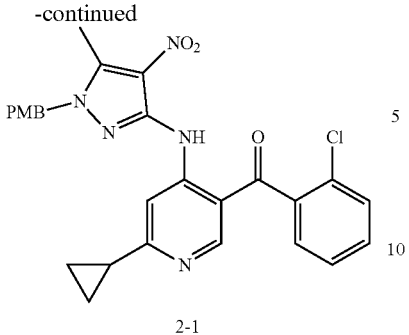

2-1

Intermediate 1-4 (3 g, 5.4 mmol) was added in toluene (90 mL), cyclopropyl boronic acid (0.70 g, 8.1 mmol), palladium acetate (0.121 g, 0.54 mmol), tricyclohexylphosphine (0.310 g, 1.1 mmol) and potassium phosphate (4.0 g, 18.8 mmol). The reactor was replaced with nitrogen 3 times. The reaction system was heated to 120° C. and reacted for 16 h. The reaction endpoint was monitored by TLC. The mixture was extracted with EA (100 mL) after cooling, and the aqueous phase separated out was extracted with EA (20 mL). The organic phases were combined, washed with saturated aqueous sodium chloride, dried over anhydrous sodium sulfate, filtered, concentrated and pulped with ethyl acetate:methyl tert-butyl ether (1:3, 10 mL). The mixture was dried to give orange solid (3.0 g, yield 86%).

Step 2: Synthesis of Intermediate 2-2

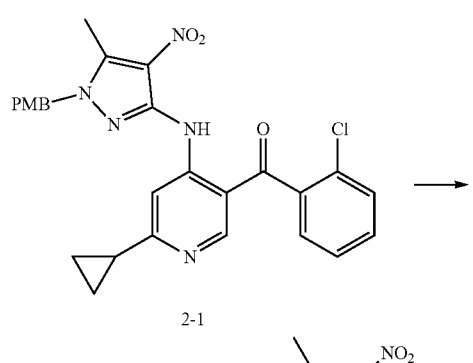

2-1

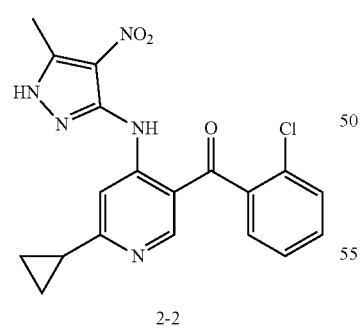

2-2

Intermediate 2-1 (2.9 g, 5.6 mmol) was added in toluene (60 mL) and dissolved.

Trifluoroacetic acid (30 mL) was added dropwise slowly. The mixture was heated to 100° C. after the addition, and reacted for 8 h. LC-MS showed the reaction endpoint. Solvent and trifluoroacetic acid were rotary evaporated to give 1.9 g brown solid, which was directly used for the next step.

44

Step 3: Synthesis of Compound 2

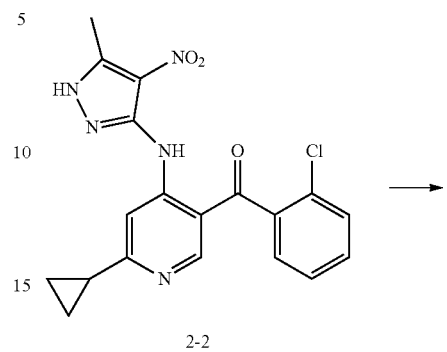

2-2

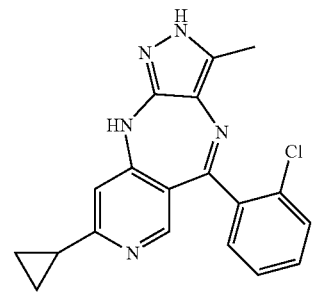

Compound 2

Intermediate 2-2 (1.9 g, 3.7 mmol) was added in 2-methyltetrahydrofuran (35 mL) and dissolved. Tin dichloride dihydrate (5.4 g, 24.8 mmol) was slowly added under nitrogen atmosphere. The mixture was heated to 100° C., and reacted for 16 h. LC-MS showed the reaction endpoint. The mixture was adjusted to pH=10 by adding sodium hydroxide aqueous solution, and filtered with celite. The filtrate was extracted with 2-methyltetrahydrofuran, and concentrated. The crude product was purified by silica gel column chromatography (eluted with EA:DCM=1:3) to obtain yellow solid (0.35 g, yield 27%).

$^1$H NMR (400 MHz, CDCl$_3$) δ: 11.65 (s, 1H), 8.42 (s, 1H), 7.33-7.47 (m, 4H), 7.01 (s, 1H), 6.40 (s, 1H), 1.96 (s, 3H), 1.71-1.75 (m, 1H), 0.72-0.84 (m, 4H).

Example 3: Synthesis of Compound 3

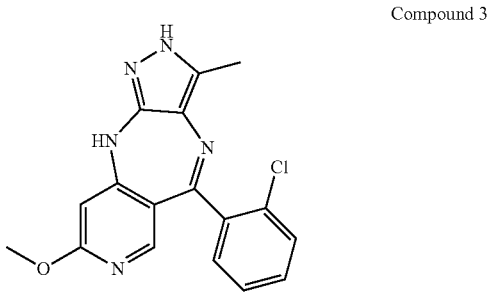 [SMILES: COc1cc2c(cn1)C(c1ccccc1Cl)=Nc1c(n[nH]c1C)N2]

Compound 3

Step 1: Synthesis of Intermediate 3-1

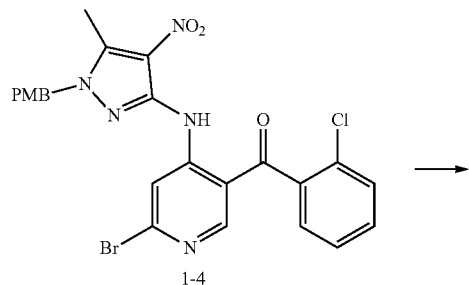

1-4

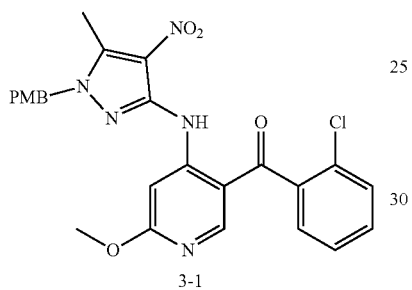

3-1

Intermediate 1-4 (3 g, 5.4 mmol) was added in THF (300 mL). Under nitrogen atmosphere, sodium methoxide-methanol solution (prepared by the reaction of sodium hydride (1.4 g, 35 mmol) and methanol (6 ml)) was added dropwise. The mixture was heated to 50° C., and reacted for 16 hours. The reaction endpoint was monitored by TLC. After cooling, the reaction system was added in saturated aqueous solution of ammonium chloride (20 mL), and then extracted with 2-methyltetrahydrofuran (50 mL). The organic phases were combined, washed with saturated brine, dried over anhydrous sodium sulfate, filtered, and concentrated. The crude product was pulped with methanol/methyl tert-butyl ether (1:3) to give yellow solid (2.1 g, yield 77%).

Step 2: Synthesis of Intermediate 3-2

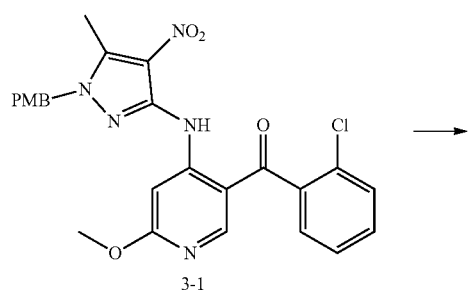

3-1

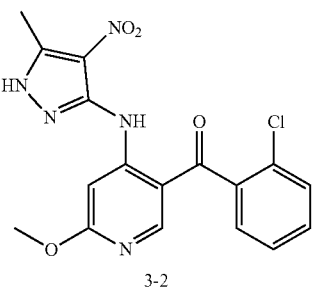

3-2

Intermediate 3-1 (1.8 g, 3.5 mmol) was added in toluene (30 mL) and dissolved. Trifluoroacetic acid (20 mL, 0.268 mol) was added dropwise slowly. The mixture was heated to 110° C., and reacted for 16 h. LC-MS showed the reaction endpoint. Solvent and trifluoroacetic acid were rotary evaporated. The residue was pulped with methyl tert-butyl ether (20 mL) and filtered to give a red solid (0.92 g, yield 52%).

Step 3: Synthesis of Compound 3

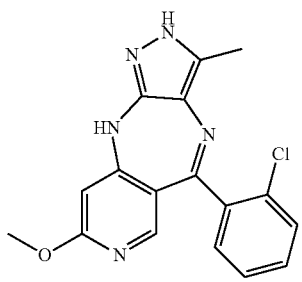

3-2

Compound 3

Intermediate 3-2 (0.92 g, 1.8 mmol) was added in 2-methyltetrahydrofuran (15 mL) and dissolved. Tin dichloride dihydrate (2.9 g, 12.8 mmol) was added under nitrogen atmosphere. The mixture was heated to 100° C., and reacted for 16 h. LC-MS showed the reaction endpoint. The mixture was adjusted to pH=10 by adding sodium hydroxide aqueous solution, and filtered with celite. The filtrate was extracted with 2-methyltetrahydrofuran, and concentrated. The crude product was purified by silica gel column chromatography (elution with EA:DCM=1:3) to obtain compound 3 as yellow solid (0.32 g, yield 52%).

$^1$H NMR (400 MHz, CDCl$_3$) δ:11.69 (s, 1H), 8.60 (s, 1H), 7.36-7.49 (m, 4H), 6.90 (s, 1H) 5.96 (s, 1H), 3.68 (s, 3H), 1.99 (s, 3H).

Example 4: Synthesis of Compound 4

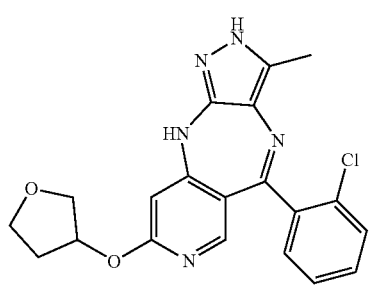

Compound 4

Step 1: Synthesis of Intermediate 4-1

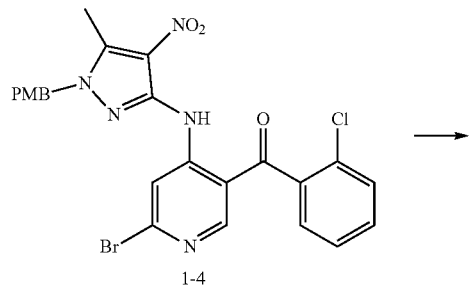

Intermediate 1-4 (3 g, 5.4 mmol) was added in cesium carbonate (6.8 g, 26.5 mmol), 3,4,7,8-tetramethyl-1,10-phenanthroline (0.127 g, 0.54 mmol), cuprous iodide (0.080 g, 0.54 mmol) and 3-hydroxytetrahydrofuran (1.0 g, 10.8 mmol). The reactor was replaced with nitrogen three times, and added toluene (20 mL). The reaction system was heated to 100° C. and reacted for 16 hours. The reaction endpoint was monitored by TLC. After cooling, the reaction system was added in saturated aqueous solution of ammonium chloride (20 mL). The aqueous phase separated out was extracted with ethyl acetate (50 mL). The organic phases were combined, washed with saturated brine, dried over anhydrous sodium sulfate, filtered, and concentrated. The crude product was pulped with methanol/methyl tert-butyl ether (1:3) to give yellow solid (0.7 g, yield 23%).

Step 2: Synthesis of Intermediate 4-2

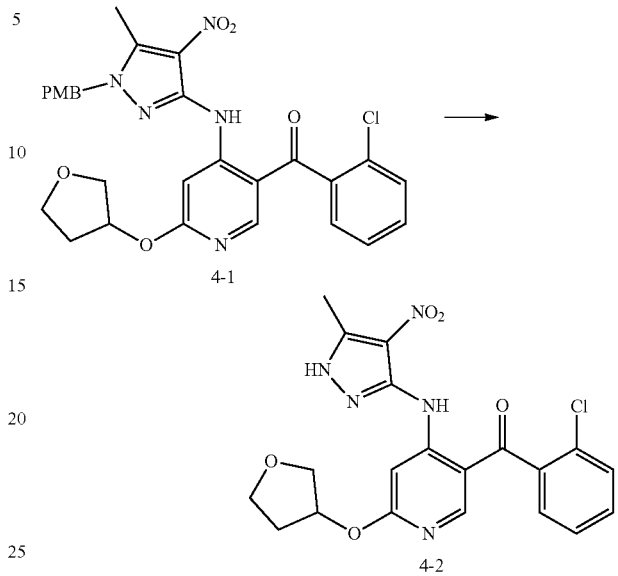

Intermediate 4-1 (0.7 g, 1.3 mmol) was added in dichloromethane (3 mL) and dissolved. Trifluoroacetic acid (10 mL) was added dropwise slowly. After the addition, the mixture was heated to 70° C., and reacted for 16 h. LC-MS showed the reaction endpoint. Solvent and trifluoroacetic acid were rotary evaporated to give red solid (0.94 g), which was used directly for the next step.

Step 3: Synthesis of Compound 4

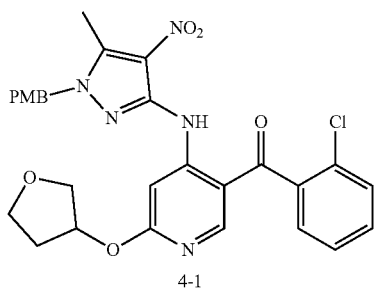

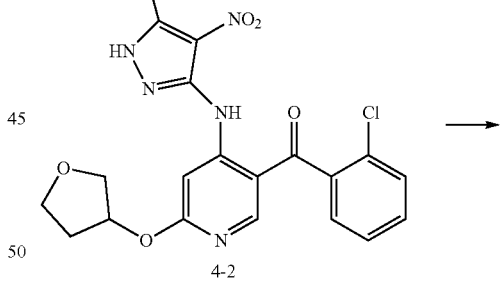

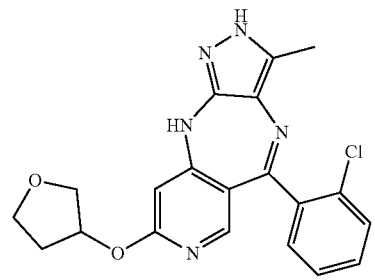

Compound 4

Intermediate 4-2 (0.94 g, 2.1 mmol) was added into 2-methyltetrahydrofuran (15 mL) and dissolved. Tin dichloride dihydrate (3.34 g, 14.8 mmol) was added under nitrogen atmosphere. The mixture was heated to 100° C., and reacting for 16 h. LC-MS showed the reaction endpoint. The mixture was adjusted to pH=10 by adding in sodium hydroxide aqueous solution, and filtered with celite. The filtrate was extracted with 2-methyltetrahydrofuran, and concentrated. The crude product was purified by silica gel column chromatography (elution with EA:DCM=1:3) to obtain compound 4 as yellow solid (0.066 g, yield 10%).

$^1$H NMR (400 MHz, CDCl$_3$) δ:11.69 (s, 1H), 8.65 (s, 1H), 7.37-7.49 (m, 4H), 6.88 (s, 1H), 5.92 (s, 1H), 5.29-5.30 (m, 1H), 3.61-3.78 (m, 4H), 2.07-2.12 (m, 1H), 2.00 (s, 3H), 1.86-1.90 (m, 1H).

Example 5: Synthesis of 5-(2-chlorophenyl)-3-methyl-8-(4-methylpiperazin-1-yl)-2,10-dihydropyrazolo[4,3-b]pyrido[4,3-e][1,4]diazepine (Compound 22)

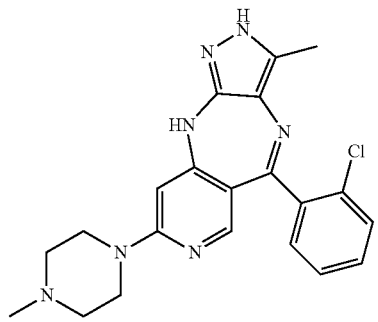 [SMILES: Cc1[nH]nc2c1N=C(c1ccccc1Cl)c1cnc(N3CCN(C)CC3)cc1N2]

Step 1: Synthesis of (2-chlorophenyl)(4-((1-(4-methoxybenzyl)-5-methyl-4-nitro-1H-pyrazol-3-yl)amino)-6-(4-methylpiperazin-1-yl)pyridin-3-yl) methanone

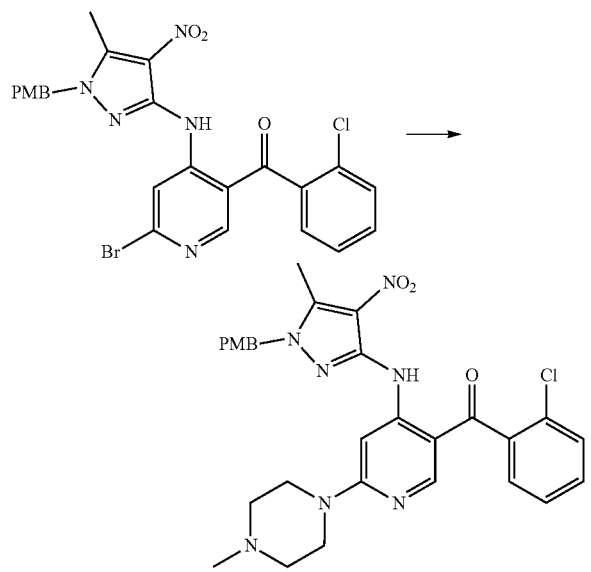

(6-bromo-4-((1-(4-methoxybenzyl)-5-methyl-4-nitro-1H-pyrazol-3-yl)amino)pyridin-3-yl)(2-chlorophenyl)methanone (intermediate 1-4) (0.80 g, 1.4 mmol) was dissolved in DMSO (10 mL), added in methylpiperazine (0.431 g, 4.3 mmol). The mixture was heated to 110° C., reacted for 4 h. TLC showed the reaction endpoint. After cooling, the reaction liquid was poured into water (100 mL), and a large amount of solid was precipitated. The mixture was filtered. The filter cake was dissolved in dichloromethane, dried and concentrated under vacuum to give a yellow solid (1.0 g crude product).

Step 2: Synthesis of (2-chlorophenyl)(4-((5-methyl-4-nitro-1H-pyrazol-3-yl)amino)-6-(4-methylpiperazin-1-yl)pyridin-3-yl) Methanone

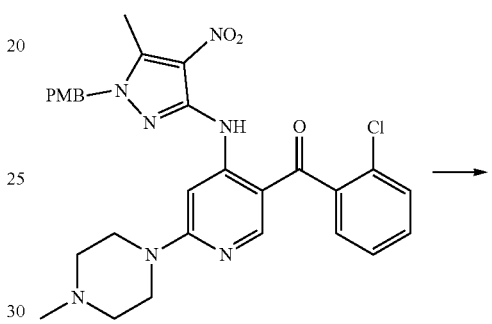

(2-chlorophenyl-4-((1-(4-methoxybenzyl)-5-methyl-4-nitro-1H-pyrazol-3-yl)amino)-6-(4-methylpiperazin-1-yl)pyridin-3-yl)methanone (1.0 g, crude product) was dissolved in dichloromethane (3 mL), then added in trifluoroacetic acid (10 mL) dropwise and slowly. Then the mixture was heated to 70° C., and reacted for 16 h. LC-MS showed the reaction endpoint. The system was concentrated under vacuum to give red solid (1.2 g, crude product), which was used directly for the next step without purification.

Step 3: Synthesis of 5-(2-chlorophenyl)-3-methyl-8-(4-methylpiperazin-1-yl)-2,10-dihydropyrazolo[4,3-b]pyrido[4,3-e][1,4]diazepine

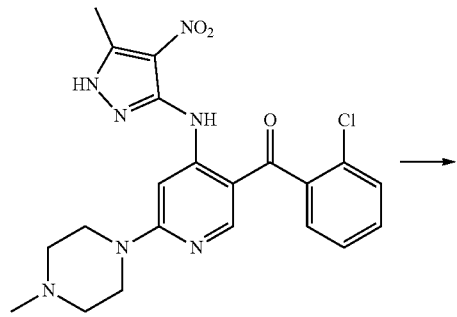

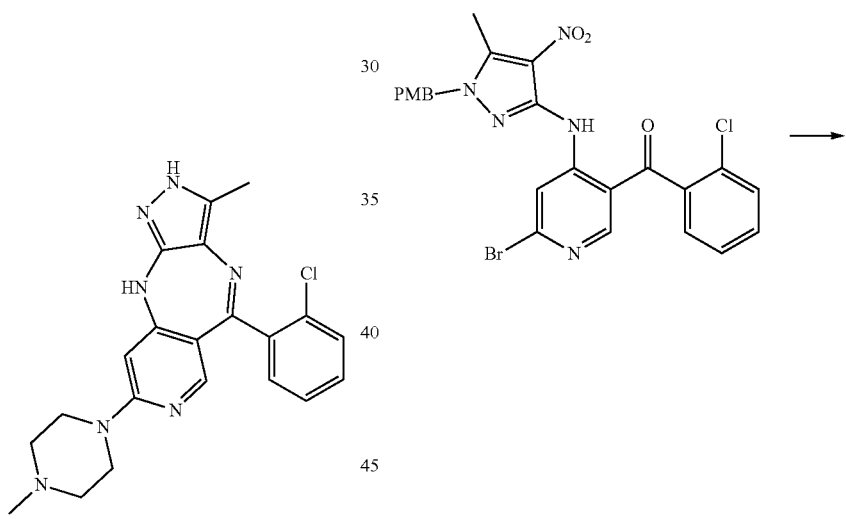

(2-chlorophenyl)(4-((5-methyl-4-nitro-1H-pyrazol-3-yl)amino)-6-(4-methylpiperazin-1-yl) pyridin-3-yl) methanone (1.2 g, crude product) was dissolved in 2-methyltetrahydrofuran (20 mL), added in tin dichloride dihydrate ((4.2 g, 18.6 mmol) under nitrogen atmosphere. The mixture was heated to 90° C., and reacted for 16 h. LC-MS showed the end of the reaction. The mixture was adjusted to pH=10 by adding sodium hydroxide aqueous solution, and filtered with celite. The filtrate was extracted with 2-methyltetrahydrofuran, and concentrated. The crude product was purified by silica gel column chromatography (dichloromethane:methanol=10:1) to obtain compound 22 as yellow solid (0.033 g, yield: 5.8% for three steps).

$^1$H NMR (400 MHz, DMSO-$d_6$): 11.56 (s, 1H), 8.23 (s, 1H), 7.33-7.45 (m, 4H), 6.88 (s, 1H), 5.96 (s, 1H), 3.37 (m, 4H), 2.33 (m, 4H), 2.19 (s, 3H), 1.97 (s, 3H).

Molecular formula: $C_{21}H_{22}ClN_7$, Molecular weight: 407.91, LC-MS (Pos, m/z)=408 [M+H$^+$].

Example 6: Synthesis of 4-(5-(2-chlorophenyl)-3-methyl-2, 10-dihydropyrazolo[4,3-b]pyrido[4,3-e][1,4]diazepin-8-yl)morpholine (Compound 29)

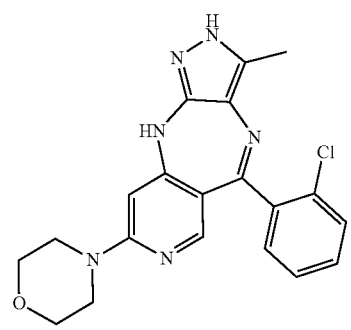 [SMILES: Cc1[nH]nc2c1N=C(c1ccccc1Cl)c1cnc(N3CCOCC3)cc1N2]

Step 1: Synthesis of (6-bromo-4-((5-methyl-4-nitro-1H-pyrazol-3-yl)amino)pyridin-3-yl)(2-chlorophenyl) Methanone

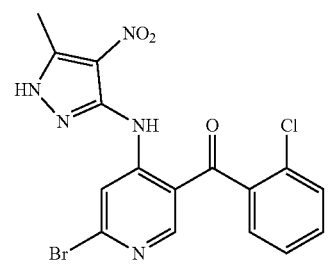

(6-bromo-4-((1-(4-methoxybenzyl)-5-methyl-4-nitro-1H-pyrazol-3-yl)amino)pyridin-3-yl)(2-chlorophenyl)methanone (intermediate 1-4) (0.80 g, 1.4 mmol) was dissolved in DCM (2 mL), then added trifluoroacetic acid (10 mL). The mixture was heated to 70° C. and reacted for 4 h. LC-MS showed the reaction endpoint. The reaction mixture was cooled and concentrated under vacuum to get a yellow solid (1.0 g, crude product).

Step 2: Synthesis of 8-bromo-5-(2-chlorophenyl)-3-methyl-2,10-dihydropyrazolo[4,3-b]pyrido[4,3-e][1,4]diazepine

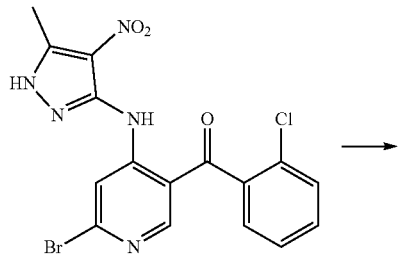

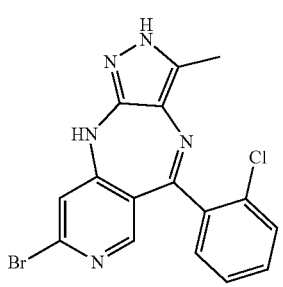

(6-bromo-4-((5-methyl-4-nitro-1H-pyrazol-3-yl)amino)pyridin-3-yl)(2-chlorophenyl) methanone (1.0 g, crude product) was dissolved in 2-methyltetrahydrofuran (15 mL), then added in tin dichloride dihydrate (3.2 g, 14.2 mmol). The mixture was heated to 100° C. and reacted for 16 h. LC-MS showed the reaction endpoint. The mixture was adjusted to pH=10 by adding sodium hydroxide aqueous solution, and filtered with celite. The filtrate was extracted with 2-methyltetrahydrofuran, and concentrated. The crude product was purified by silica gel column chromatography (dichloromethane:methanol=30:1) to obtain product (60 mg, yield 10.7% for two steps).

Step 3: Synthesis of 4-(5-(2-chlorophenyl)-3-methyl-2,10-dihydropyrazolo[4,3-b]pyrido[4,3-e][1,4]diazepin-8-yl) morpholine

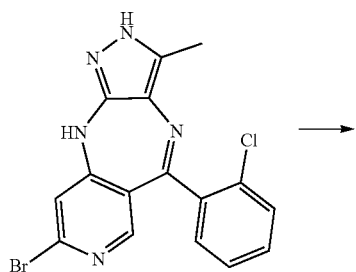

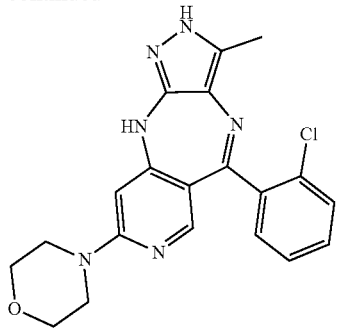

8-bromo-5-(2-chlorophenyl)-3-methyl-2,10-dihydropyrazolo[4,3-b]pyrido[4,3-e][1,4]diazepine (60 mg, 0.16 mmol) was dissolved in DMSO (2 mL), then added in morpholine (14 mg, 0.20 mmol) under nitrogen. The mixture was heated to 110° C. and reacted for 6 hours. LC-MS showed the reaction endpoint. The reaction liquid was poured into water (10 mL), extracted with dichloromethane (20 mL*2), and concentrated. The crude product was purified by silica gel column chromatography (dichloromethane:methanol=20:1) to obtain product (16 mg, yield 25%).

$^1$H-NMR (400 MHz, DMSO-d$_6$): 11.56 (s, 1H), 8.29 (s, 1H), 7.33-7.47 (m, 4H), 6.88 (s, 1H), 5.96 (s, 1H), 3.62 (m, 4H), 3.33 (m, 4H), 1.97 (s, 3H).

Molecular formula: $C_{20}H_{19}ClN_6O$, Molecular weight: 394.86, LC-MS (Pos, m/z)=394.96 [M+H$^+$].

Example 7: Synthesis of Compound 33

Step 1: Synthesis of Intermediate 33-1

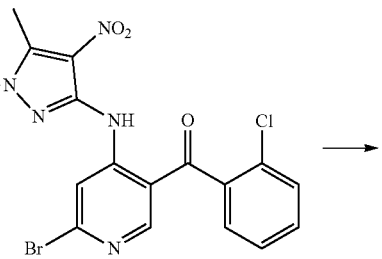

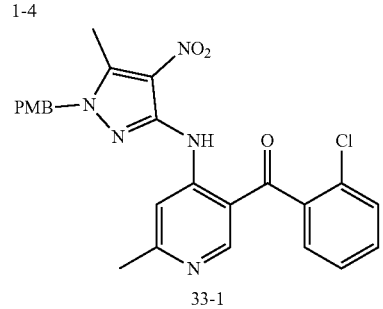

Intermediate 1-4 3.5 g (6.3 mmol) was added with 3.8 g (19.1 mmol) of potassium carbonate and 1.06 g (0.63 mmol) of tetrakistriphenylphosphine palladium. The reactor was replaced with nitrogen three times, then 2 ml trimethylboroxine (6.8 mmol) was added thereto dropwise, then 40 ml dioxane was added. The reaction mixture was heated to 110° C. and reacted for 16 hours. The reaction endpoint was monitored by TLC. After cooling, the reaction liquid was poured into 100 ml of water, and a large amount of solid was precipitated. After filtration, the mixture was added in silica gel, and subjected to column chromatography, eluted with dichloromethane:methanol=100:1, and rotary evaporated to dryness, giving 1.8 g of intermediate 33-1 as yellow solid, with a yield of 58.8%.

Step 2: Synthesis of Intermediate 33-2

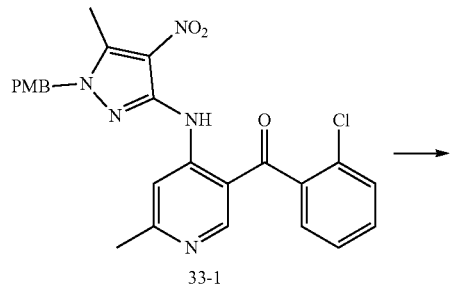

33-1

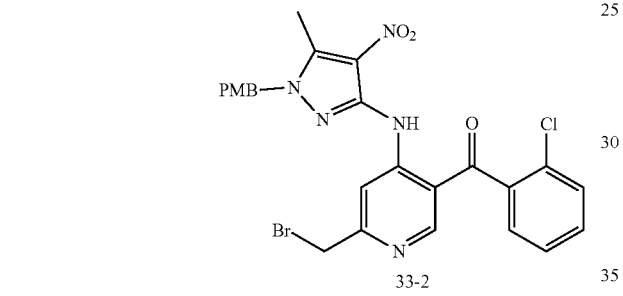

33-2

1.8 g (3.6 mmol) of intermediate 33-1 was added in 0.65 g of NBS (3.6 mmol) and 100 ml of carbon tetrachloride, stirred to dissolve for 30 minutes, and then added 89 mg of benzoyl peroxide (0.36 mmol). The reaction mixture was heated to 100° C. and reacted for 16 h. LC-MS showed the reaction endpoint. After the solvent was evaporated, the mixture was dissolved in 20 ml methylene chloride, filtered over silica gel, and evaporated to dryness, giving 2.0 g intermediate 33-2 as yellow solid, which was directly used for the next step.

Step 3: Synthesis of Intermediate 33-3

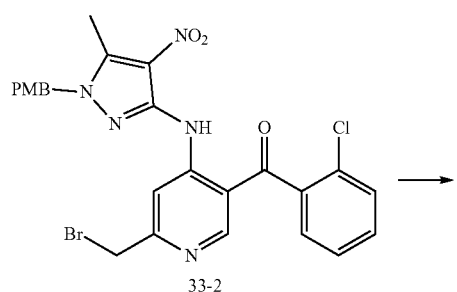

33-2

-continued

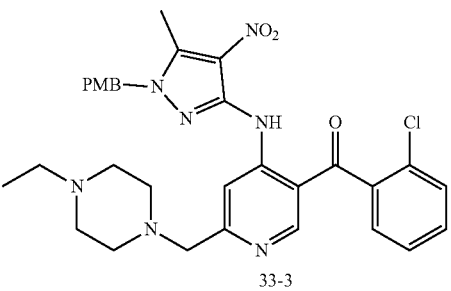

33-3

Intermediate 33-2 (2.0 g, 3.5 mmol) was added in 0.55 g of ethyl piperazine (4.8 mmol), 0.73 g of potassium carbonate (5.2 mmol) and 20 ml of acetonitrile. The mixture was heated to 80° C. and reacted for 8 h. LC-MS showed the reaction endpoint. The solvent was evaporated, and 100 ml of DCM and 50 ml of aqueous solution of ammonium chloride were added. After liquid separation, drying and concentration, 1.9 g of intermediate 33-3 was obtained as red solid, which was directly used for the next step.

Step 4: Synthesis of Intermediate 33-4

33-3

33-4

1.9 g of intermediate 33-3 (3.2 mmol) was added into dichloromethane (3 mL) to dissolve. Then, trifluoroacetic acid (10 mL) was slowly added dropwise. After the addition, the mixture was heated to 70° C. and reacted for 16 h. LC-MS showed the reaction endpoint. Solvent and trifluoroacetic acid were evaporated to give 2.4 g intermediate 33-4 as red solid, which was directly used for the next step.

Step 4: Synthesis of Compound 33

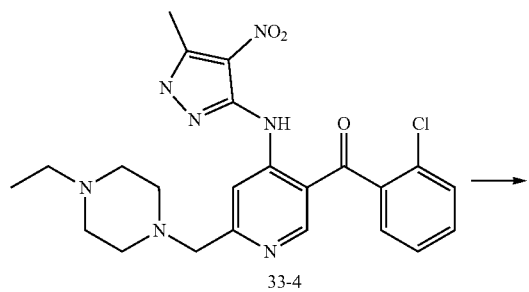

33-4

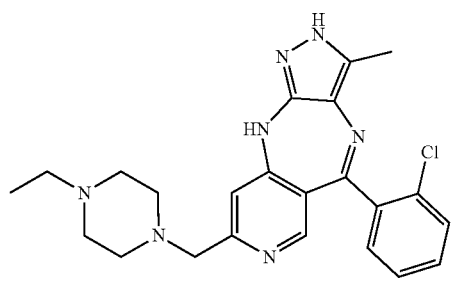

Compound 33

Intermediate 33-4 (2.4 g, 4.9 mmol) was added into 2-methyltetrahydrofuran (25 mL) to dissolve. Then, tin dichloride dihydrate (7.8 g, 34.8 mmol) was added under nitrogen atmosphere, and the mixture was heated to 90° C. After 16 h of reaction, LC-MS showed the reaction endpoint. The mixture was adjusted to pH=10 by adding sodium hydroxide aqueous solution, and filtered with celite. The filtrate was extracted with 2-methyltetrahydrofuran, and concentrated. The crude product was purified by silica gel column chromatography (dichloromethane:methanol=10:1) to obtain compound 33 (0.047 g, yield 10%).

$^1$H NMR (400 MHz, DMSO): 11.50 (S, 1H), 8.72 (S, 1H), 7.43-7.47 (m, 4H), 7.27 (s, 1H), 6.67 (s, 1H), 3.47 (s, 2H), 3.06 (m, 4H), 2.97 (m, 2H), 2.71 (s, 4H), 2.12 (s, 3H), 1.26-1.29 (t, 3H).

Example 8: Synthesis of Compound 34

Step 1: Synthesis of Intermediate 34-1

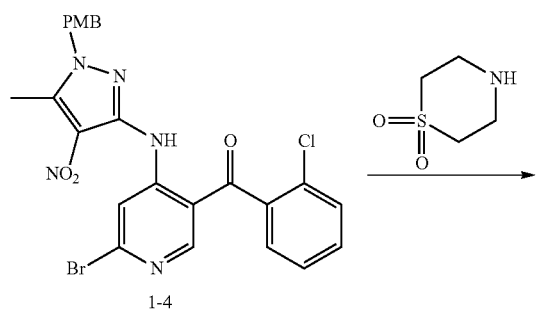

1-4

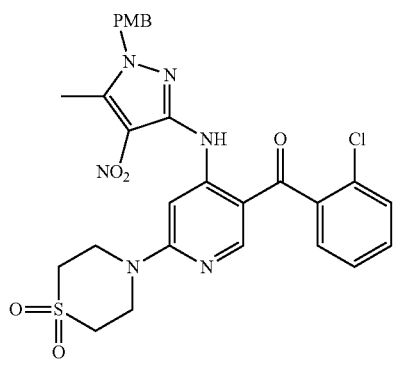

34-1

Intermediate 1-4 (120 mg, 0.216 mmol, 1 eq) was added into DMSO (2 mL), then added thiomorpholine 1,1-dioxide (58.1 mg, 0.43 mmol, 2 eq) and DIEA (83.6 mg, 0.65 mmol, 3 eq). The mixture was heated to 80° C. and reacted for 3 h. The end of the reaction was monitored by TLC. Water (10 ml) was added dropwise to the reaction liquid, and solid intermediate 34-1 (70 mg, crude) was precipitated, which was used directly for the next step.

Step 2: Synthesis of Intermediate 34-2

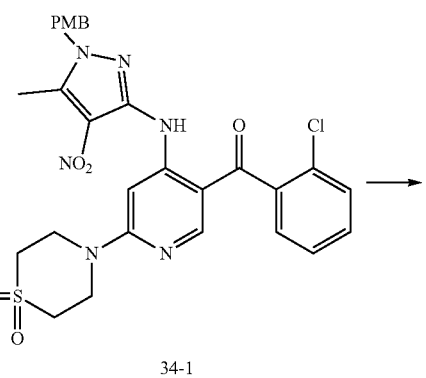

34-1

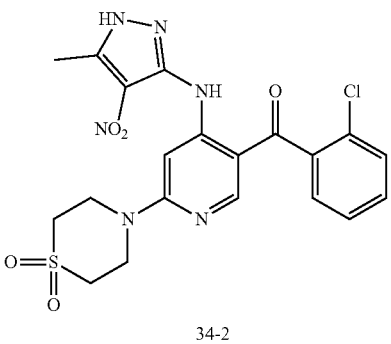

34-2

The intermediate 34-1 (70 mg, 0.11 mmol, 1 eq) was added in 2 ml of trifluoroacetic acid. The mixture was heated to 80° C. and reacted for 5 h. The end of the reaction was monitored by TLC. The reaction liquid was evaporated to dryness, and pulped with MTBE (10 mL) to get intermediate 34-2 as yellow solid (30 mg, crude product).

Step 3: Synthesis of Compound 34

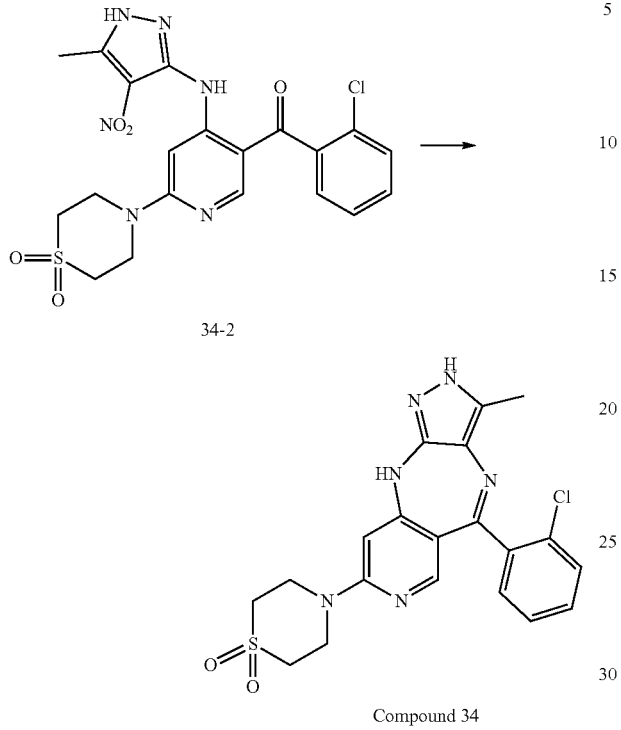

34-2

Compound 34

Intermediate 34-2 (300 mg, 0.62 mmol, 1 eq) was added in a 25 ml single-necked flask, then added 2-methyltetrahydrofuran (20 ml) and stannous chloride (966 g, 4.28 mmol, 7 eq). The mixture was heated to 90° C. and stirred for 5 hours. The end of the reaction was monitored by TLC. The reaction solution was cooled and adjusted to about pH 8 with sodium hydrogen carbonate. The mixture was extracted with DCM (50 ml), and the organic phase was separated out, dried, combined and evaporated to dryness, giving compound 34 (21 mg, yield: 2.1% for three steps) by preparing silica gel plate (DCM:MeOH=30:1).

$^1$H NMR (400 MHz, DMSO-$d_6$): 11.60 (s, 1H), 8.30 (s, 1H), 7.33-7.49 (m, 4H), 6.92 (s, 1H), 6.11 (s, 1H), 3.88 (m, 4H), 3.08-3.10 (m, 4H), 1.98 (s, 3H).

Example 9: Synthesis of Compound 37

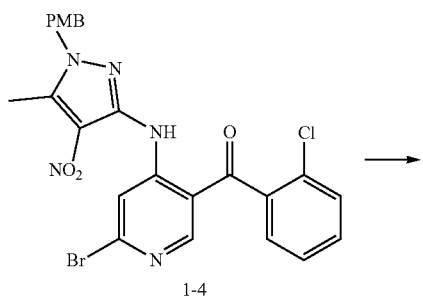

1-4

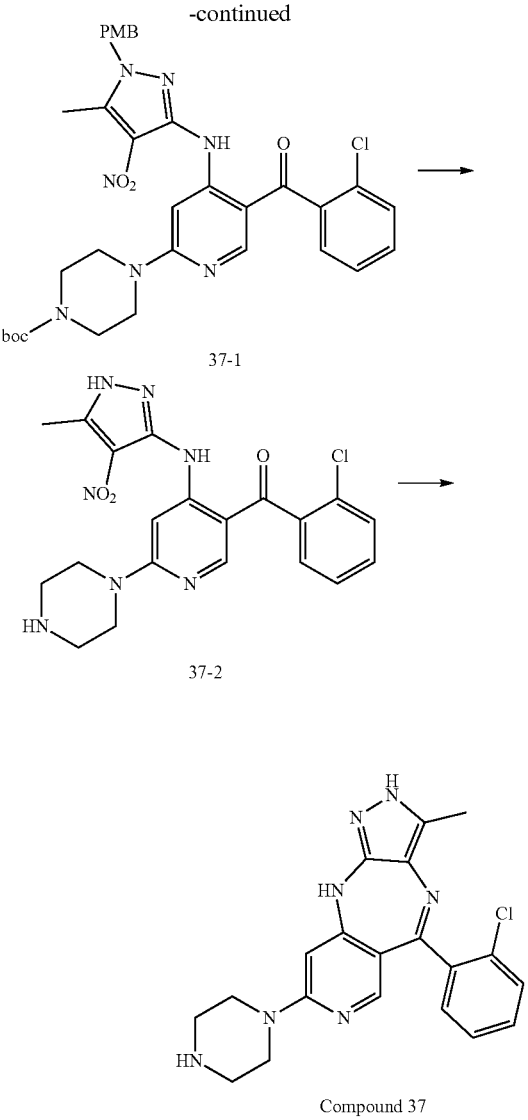

37-1

37-2

Compound 37

Step 1: 500 mg of intermediate 1-4 was weighed and added into 15 ml of acetonitrile to dissolve, then added with 200 mg of triethylamine and 200 mg of BOC piperazine. The mixture was heated to reflux for 3 h. The end of the reaction was monitored by TLC, and the reaction solution was evaporated to dryness to obtain intermediate 37-1 as yellow solid, 400 mg, yield 80%.

Step 2: The intermediate 37-1 was dissolved in 15 ml TFA, and the mixture was heated to reflux for 6 h. The end of the reaction was monitored by LC-MS. The mixture was evaporated to dryness. After filtration, the crude product was pulped with methyl tert-butyl ether to obtain compound 37-2 as yellow solid (300 mg, yield >100%).

Step 3: The intermediate 37-2 was dissolved in 15 ml methyltetrahydrofuran, then added with 500 ml of tin dichloride dihydrate. The mixture was heated to 90° C. and refluxed for 5 hours, and the reaction was completed to obtain compound 37 (16 mg, yield 5%).

$^1$H NMR (400 MHz, DMSO-$d_6$): 11.60 (s, 1H), 8.30 (s, 1H), 7.33-7.49 (m, 4H), 6.92 (s, 1H), 6.11 (s, 1H), 3.88 (m, 4H), 2.08-2.10 (m, 4H), 1.98 (s, 3H).

Example 10: Synthesis of Compound 38

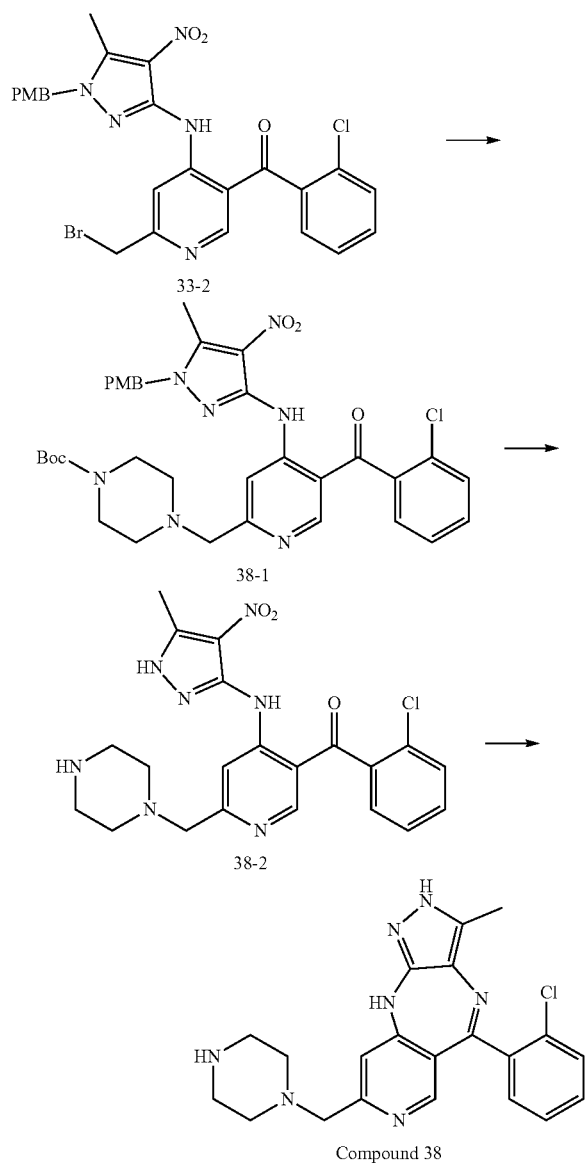

Step 1: Boc piperazine 300 mg, 450 mg intermediate 33-2 and potassium carbonate 300 mg were weighed and added with 20 ml of acetonitrile to dissolve. The mixture was heated to 60° C. and reacted for 6 h. The end of the reaction was monitored by LC-MS. 300 ml water and 50 ml dichloromethane were added. The oil phase separated out was dried and evaporated to dryness, giving an intermediate 38-1, 300 mg.

Step 2: 15 ml trifluoroacetic acid was poured into 300 mg compound 38-1. The mixture was heated to 90° C. and refluxed for 4 h. The end of the reaction was monitored by LC-MS, and reaction mixture was evaporated to dryness, giving 200 mg compound 38-2.

Step 3: 1.10 g tin dichloride dihydrate was weighed and added with the intermediate 38-2, 15 ml methyltetrahydrofuran and 0.2 ml of water. The mixture was heated to 90° C. and reacted for 16 h. After the reaction was finished, the reaction mixture was adjusted to pH 10, filtered, evaporated to dryness and dried, obtaining 36 mg compound 38 in a yield of 21%.

$^1$H NMR (400 MHz, DMSO): 11.69 (s, 1H), 8.49 (s, 1H), 7.38-7.49 (m, 4H), 7.10-7.25 (m, 1H), 2.57-2.58 (m, 4H), 2.26 (s, 2H), 2.35 (s, 4H), 1.98 (s, 3H).

Example 11: Synthesis of Compounds 40, 41, 42, 43, 44, 45, 46, 48

The synthetic route was as follows:

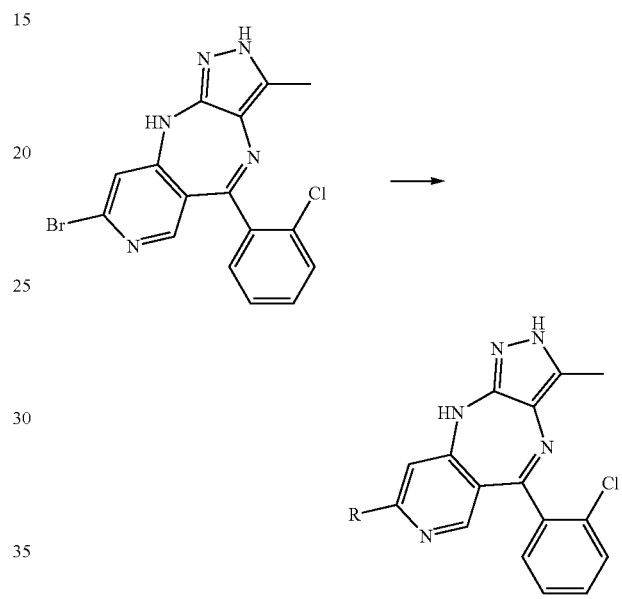

General synthetic method: 8-bromo-5-(2-chlorophenyl)-3-methyl-2,10-dihydropyrazolo[4,3-b]pyrido[4,3-e][1,4]diazepine (1 eq) prepared in the step 2 of Example 6 was dissolved in DMSO (5 ml), and added with amine (5 eq) of different structures under nitrogen. The mixture was heated to 100° C. and reacted for 16 hours. TLC showed that the reaction was completed. The reaction liquid was poured into ice water (50 ml), and a crude product was precipitated as yellow solid.

11.1 Synthesis of compound 41: the structure of the amine was

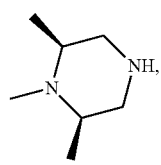

the solid crude product was purified with prepared silica gel plate (DCM:MeOH=30:1) to obtain compound 41 (15 mg, yield: 13.8%).

$^1$H NMR (400 MHz, CDCl3): 8.85 (s, 1H), 7.28-7.42 (m, 4H), 5.91 (s, 1H), 5.62 (s, 1H), 3.98-4.02 (d, 2H), 2.66-2.72 (t, 2H), 2.29 (s, 3H), 2.22 (s, 4H), 1.14-1.16 (m, 6H).

Compound 41

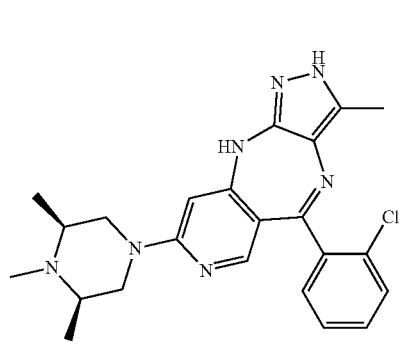

11.2 Synthesis of compound 42: the structure of amine was

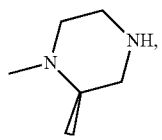

the solid crude product was dissolved in dichloromethane (20 ml), dried over magnesium sulfate and evaporated to dryness to obtain compound 42 (22 mg, yield: 20.4%).

$^1$H NMR (400 MHz, CDCl$_3$): 8.85 (s, 1H), 7.28-7.42 (m, 4H), 5.91 (s, 1H), 5.62 (s, 1H), 3.98-4.02 (d, 2H), 2.66-2.72 (t, 2H), 2.29 (s, 3H), 2.22 (m, 4H), 1.14-1.16 (m, 6H).

Compound 42

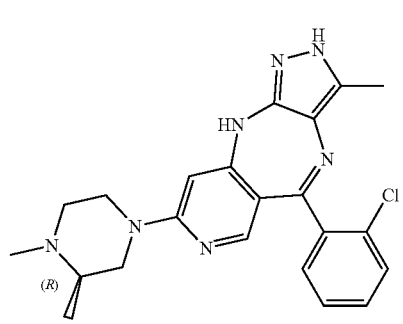

11.3 Synthesis of compound 44: the structure of amine was

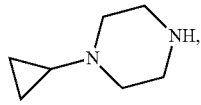

the crude product was dried to obtain compound 44 (90 mg, yield: 40.35%).

$^1$H NMR (400 MHz, DMSO): 11.59 (s, 1H), 8.26 (s, 1H), 7.32-7.48 (m, 4H), 6.89 (s, 1H), 5.77 (s, 1H), 1.98 (s, 3H), 1.62 (m, 1H), 0.33-0.43 (m, 4H).

Compound 44

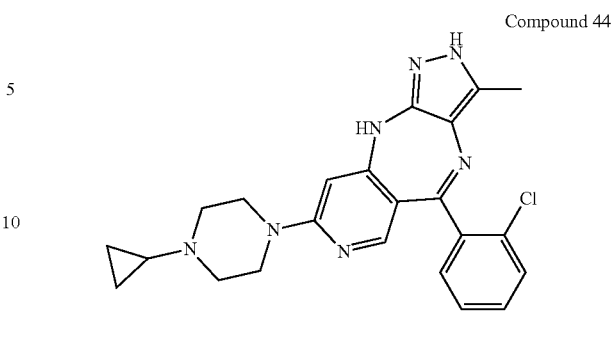

11.4 Synthesis of compound 45: the structure of amine was

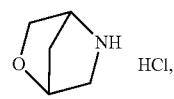

the crude product was dissolved in dichloromethane (10 ml), dried over magnesium sulfate and evaporated to dryness to obtain yellow solid, which was washed with dichloromethane: petroleum ether=1:1 to give compound 45 (42 mg, yield: 20.1%).

$^1$H NMR (400 MHz, DMSO): 11.59 (s, 1H), 8.28 (s, 1H), 7.32-7.48 (m, 4H), 6.86 (s, 1H), 4.62-4.67 (m, 3H), 3.54-3.71 (dd, 2H), 3.07-3.13 (m, 2H), 1.98 (s, 3H), 1.77-1.84 (m, 2H), 0.82-0.87 (m, 2H).

Compound 45

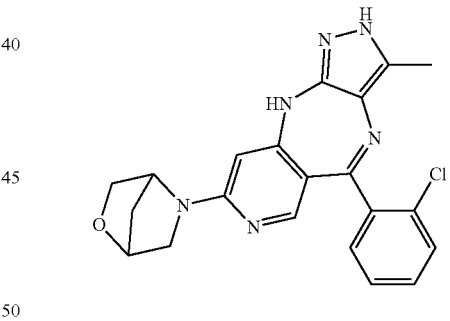

11.5 Synthesis of compound 46: the structure of amine was

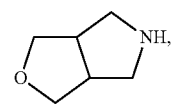

the crude product was dried to obtain compound 46 (130 mg, yield: 59.9%).

$^1$H NMR (400 MHz, DMSO): 11.55 (s, 1H), 8.28 (s, 1H), 7.32-7.48 (m, 4H), 6.87 (s, 1H), 5.69 (s, 1H), 3.76-3.80 (m, 2H), 3.46-3.53 (m, 4H), 3.17-3.20 (d, 2H), 2.95 (s, 2H), 1.97 (s, 3H).

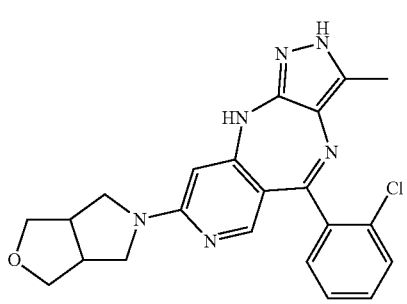

Compound 46

11.6 Synthesis of compound 43: the structure of amine was

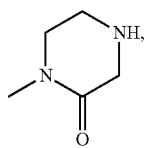

the crude product was dried to obtain compound 43 (55 mg, yield: 57.9%).

$^{1}$H NMR (400 MHz, DMSO): 11.59 (s, 1H), 8.30 (s, 1H), 7.33-7.46 (m, 4H), 6.90 (s, 1H), 5.92 (s, 1H), 3.89 (s, 2H), 3.65-3.67 (m, 2H), 3.31-3.36 (m, 2H), 3.15-3.17 (d, 1H), 2.86 (s, 3H), 1.97 (s, 3H).

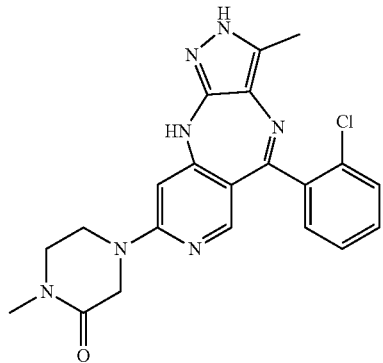

Compound 43

11.7 Synthesis of Compound 40: The structure of the amine was

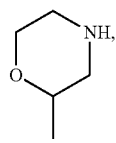

the crude product was dried to obtain compound 40 (30 mg, yield: 39.9%).

$^{1}$H NMR (400 MHz, DMSO): 11.57 (s, 1H), 8.24 (s, 1H), 7.33-7.46 (m, 4H), 6.89 (s, 1H), 5.96 (s, 1H), 3.79-3.93 (m, 4H), 3.45-3.46 (m, 2H), 2.75-2.81 (t, 1H), 3.15-3.17 (d, 1H), 1.97 (s, 3H), 1.08-1.09 (d, 3H).

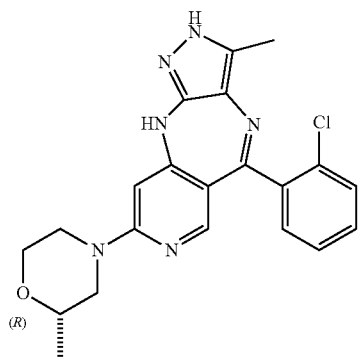

Compound 40

11.8 Synthesis of compound 48: the structure of amine was

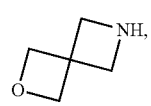

the crude product was dried to obtain compound 48 (127 mg, yield: 60%).

$^{1}$H NMR (400 MHz, DMSO): 11.56 (s, 1H), 8.33 (s, 1H), 7.32-7.43 (m, 4H), 6.84 (s, 1H), 5.53 (s, 1H), 4.67 (s, 3H), 4.01 (s, 4H), 1.97 (s, 3H).

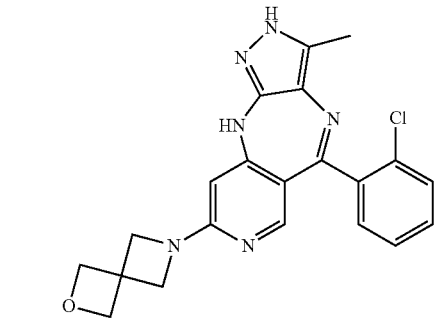

Compound 48

Example 12: Synthesis of Compound 47

Step 1: Synthesis of Intermediate 47-1

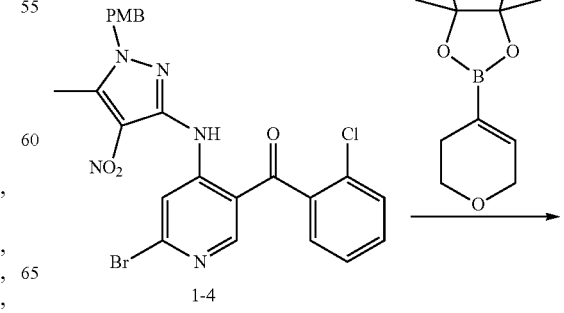

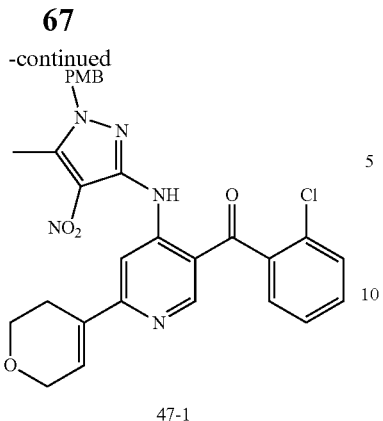

(47-1)

Intermediate 1-4 (500 mg, 0.9 mmol, 1 eq) was added to DMF (20 mL), then added with potassium phosphate (573 mg, 2.7 mmol, 3 eq), 2-(3,6-dihydro-2H-pyran-4-yl)-4,4,5,5-tetrahydro-1,3,2-dioxaborolane (246 mg, 1.17 mmol, 1.2 eq), palladium acetate (10 mg, 0.045 mmol, 0.05 eq). The reactor was replaced with nitrogen for three times. The mixture was heated to 100° C. and reacted for 16 h. The end of the reaction was monitored by TLC. The reaction liquid was poured into ice-water (50 ml) and extracted with ethyl acetate (50 ml*3). The organic phase was separated, dried, evaporated to dryness, giving intermediate 47-1 as yellow solid (500 mg, the crude product was used directly for the next step).

Step 2: Preparation of Intermediate 47-2

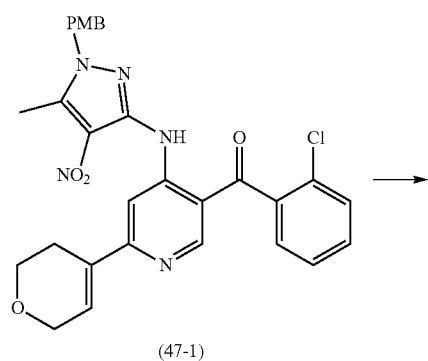

(47-1)

Under nitrogen atmosphere, intermediate 47-1 (1.50 g, 2.67 mmol, 1 eq) was added into a 100 ml single-necked flask, then THF (5 ml), methanol (5 ml), palladium on carbon (0.15 g) were added. Triethylsilane (3.1 g, 26.7 mmol, 10 eq) was added dropwise under nitrogen atmosphere, and the mixture was stirred at 15° C. for 5 min. The completely conversion of the starting materials was monitored by TLC. After reaction, the reaction mixture was filtered, and the filtrate was evaporated to dryness. The crude product was added to MTBE (10 ml) and filtered to obtain 47-2 (0.67 g, yield 44.67%).

Step 3: Synthesis of Intermediate 47-3

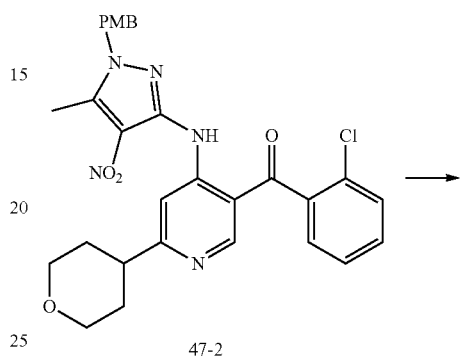

47-2

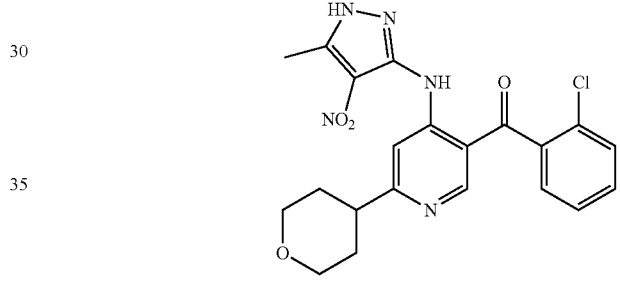

(47-3)

The intermediate 47-2 (0.67 g, 1.2 mmol, 1 eq) was added into a 25 ml single-necked flask, then added with trifluoroacetic acid (5 ml). The mixture was heated to 80° C. and reacted for 16 h. The end of the reaction was monitored by TLC. The reaction liquid was evaporated to dryness, giving intermediate 47-3 as yellow oil (1.0 g, the crude product was used directly for the next step).

Step 4: Synthesis of Compound 47

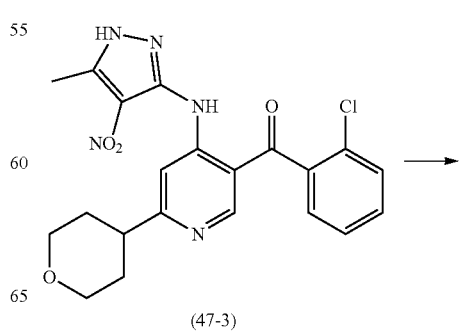

(47-3)

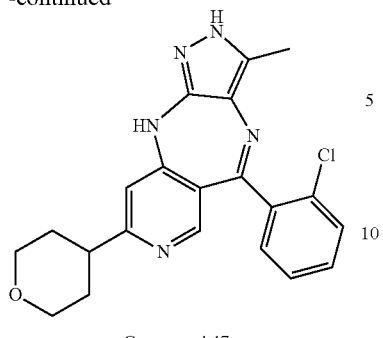

Compound 47

Intermediate 47-3 (1.0 g, 1.2 mmol, 1 eq) was added to a 25 ml single-necked flask, then added with 2-methyltetrahydrofuran (5 ml) and stannous chloride (1.89 g, 8.6 mmol). The mixture was heated to 90° C. and stirred for 5 hours. The end of the reaction was monitored by TLC. The reaction liquid was cooled and adjusted to pH 8 with sodium hydrogen carbonate. The mixture was extracted with DCM (50 ml), and the organic phase was separated, dried, combined and evaporated to dryness, giving compound 47 (36 mg, yield: 6.2% for two-steps) by preparing silica gel plate (DCM:MeOH=30:1).

$^1$H NMR (400 MHz, DMSO-$d_6$): 11.68 (s, 1H), 8.45 (s, 1H), 7.36-7.49 (m, 4H), 7.11 (s, 1H), 6.41 (s, 1H), 3.86-3.88 (d, 2H), 3.35-3.38 (m, 2H), 2.55-2.59 (m, 3H), 1.97 (s, 3H), 1.48-1.63 (m, 3H).

Example 13: Preparation of Crystal Form I of the Invention

Compound 29 (500.0 mg) of formula (III) was added to a 100 mL single-necked flask, then added with 80.0 mL of a mixture of ethanol: 2-methyltetrahydrofuran=5:1 (v:v). The reaction liquid was heated to 100° C. to make it clarify, slowly added with compound 29 in portions, for a total of 100.00 mg, until the reaction liquid was clarified. Then the solution was naturally cooled to room temperature, stirred overnight, filtered and dried to give 320.00 mg of crystal form I.

Using Cu-Kα radiation, X-ray powder diffraction of crystal form I expressed in 2θ angle (°) showed strong characteristic peaks at 7.4±0.2°, 17.9±0.2°, 18.9±0.2°, 19.4±0.2°, 21.5±0.2° and 23.7±0.2°; as well as characteristic peaks at 14.0±0.2°, 15.0±0.2°, 20.7±0.2°, and 25.4±0.2°; and also characteristic peaks at 11.7±0.2°, 22.8±0.2°, and 27.8±0.2°. The XRPD analysis is shown in FIG. 1.

Figure 2:
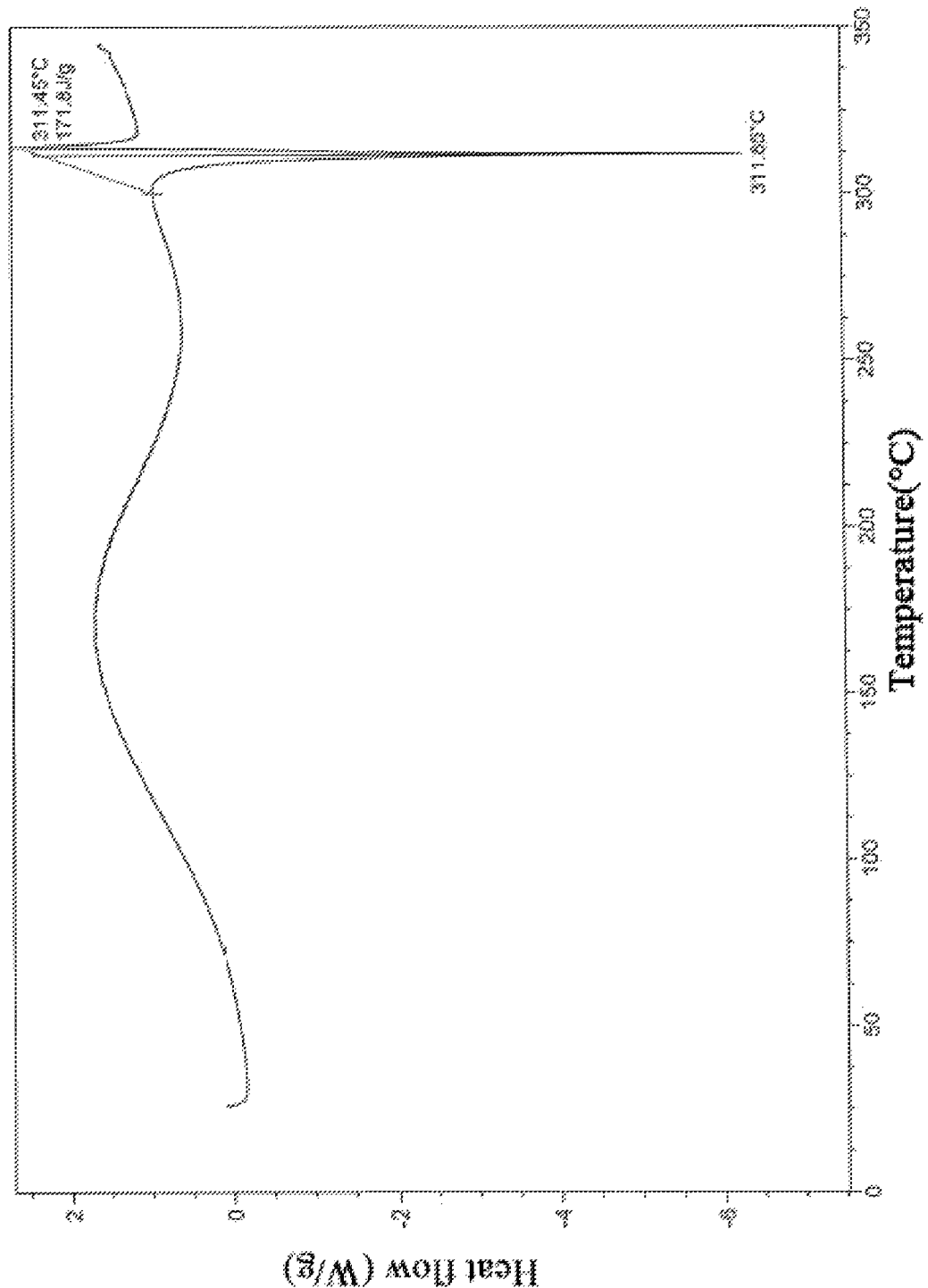
FIG. 2 is a differential scanning thermal analysis (DSC) pattern of the crystal form I of the compound of formula (III).

The endotherm of crystal form I staring from about 311° C. and the endotherm peak at about 312° C. were measured by differential scanning calorimetry. The DSC spectrum is shown in FIG. 2.

Example 14: Preparation of Crystal Form I of the Invention

Compound 29 (500.0 mg) of formula (III) was added to a 100 mL single-necked flask, then added with 6.0 mL of a mixture of dimethyl sulfoxide:water=2:1 (v:v). The reaction mixture was heated to 100° C., and slowly added dropwise with 57 mL of mixture of dimethyl sulfoxide:water=2:1, until the solution was clarified. The reaction mixture was naturally cooled to the room temperature, stirred overnight, filtered and dried to give 320.00 mg of crystal Form I.

Example 15: Preparation of Crystal Form I of the Invention

Compound 29 (500.0 mg) of formula (III) was added to a 100 mL single-necked flask, added with MeOH:DCM=5:1 (60 mL), and heated to completely dissolve. The mixture was concentrated under reduced pressure at 35-40° C. on a rotary evaporator to afford crystal form I (320.00 mg).

Example 16: Preparation of Crystal Form I of the Invention

Compound 29 (500.0 mg) of formula (III) was added to a 25 mL single-necked flask, then added with MeOH (1.5 mL). The reaction mixture was stirred at the room temperature for 7 days, filtered under reduced pressure, dried to afford crystal form I (320.00 mg).

Example 17: Preparation of Crystal Form I of the Invention

Step 1: Synthesis of (2-chlorophenyl)(4-((1-(4-methoxybenzyl)-5-methyl-4-nitro-1H-pyrazol-3-yl)amino)-6-morpholinopyridin-3-yl)methanone (Intermediate III-E)

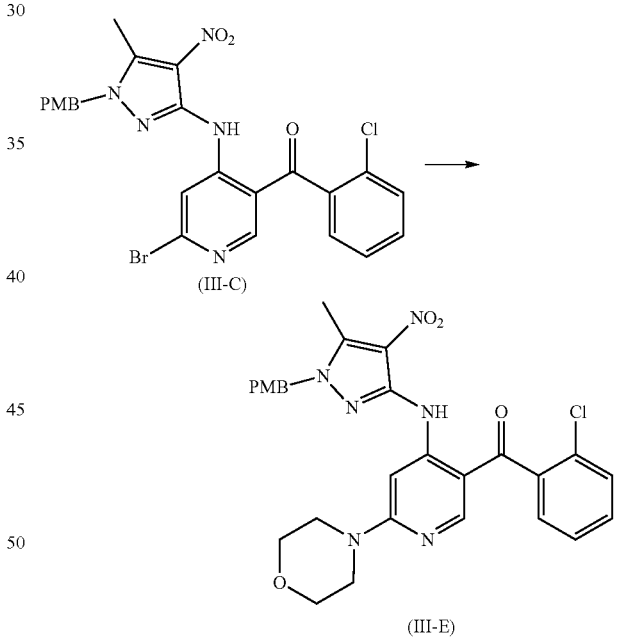

(6-bromo-4-((1-(4-methoxybenzyl)-5-methyl-4-nitro-1H-pyrazol-3-yl)amino)pyridin-3-yl)(2-chlorophenyl)methanone (intermediate III-C) (150.0 g, 269 mmol) was dissolved in DMSO (300 mL). The mixture was heated to 50° C. to dissolve the solid, then added dropwise with morpholine (III-D) (70.4 g, 808 mmol). Then, the mixture was heated to 90° C. and reacted for 3 h. TLC showed the end of the reaction. The reaction liquid was poured into water (3 L), a large amount of solid were precipitated and filtered. The filter cake was washed with water (500 mL), dried to give intermediate III-E as yellow solid (160.0 g crude product).

Step 2: Synthesis of (2-chlorophenyl)(4-((-5-methyl-4-nitro-1H-pyrazol-3-yl)amino)-6-morpholinopyridin-3-yl) Methanone (Intermediate III-F)

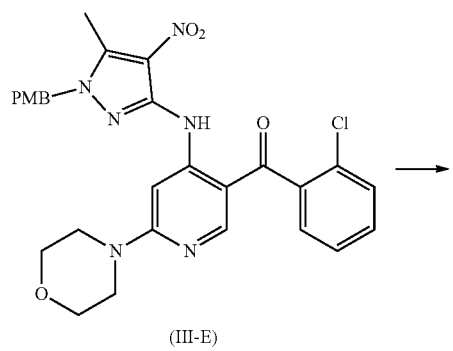

(III-E)

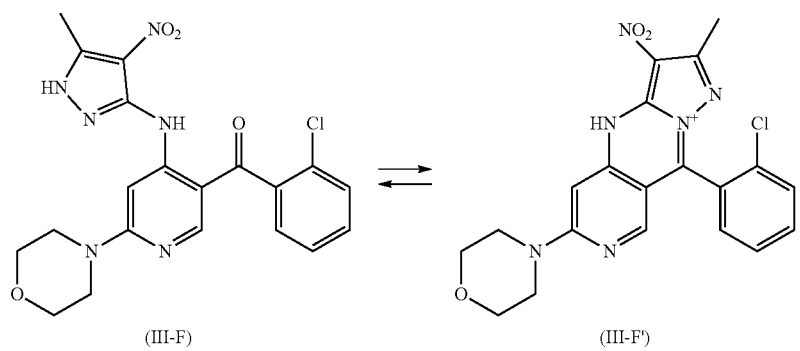

(III-F)     (III-F')

(2-chlorophenyl)(4-((1-(4-methoxybenzyl)-5-methyl-4-nitro-1H-pyrazol-3-yl)amino)-6-morpholinopyridin-3-yl) methanone (Intermediate III-E) (160.0 g, crude product) was added with trifluoroacetic acid (500 mL). The mixture was heated to 80° C. and reacted for 8 h. LC-MS showed the end of the reaction. Then, the reaction mixture was concentrated, the crude product was pulped with methyl tert-butyl ether (800 mL), filtered to get intermediate III-F as brick red solid (160 g, crude product).

1H NMR (400 MHz, DMSO-d6) δ ppm: 13.63 (brs., 1H), 12.39 (s, 1H), 7.95-7.93 (d, J=10.6 Hz, 2H), 7.62-7.48 (m, 4H), 3.74-3.70 (m, 4H), 3.64-3.63 (m, 4H), 2.58 (s, 3H).

In the preparation process, it is also possible to obtain a transition state of formula (III-F') from formula (III-E), and the crude product obtained was subjected to an acidic process (for example, treated with hydrochloric acid) to finally obtain the target intermediate formula (III-F).

Step 3: Synthesis of 4-(5-(2-chlorophenyl)-3-methyl-2,10-dihydropyrazolo[4,3-b]pyrido[4,3-e][1,4]diazepin-8-yl) Morpholine

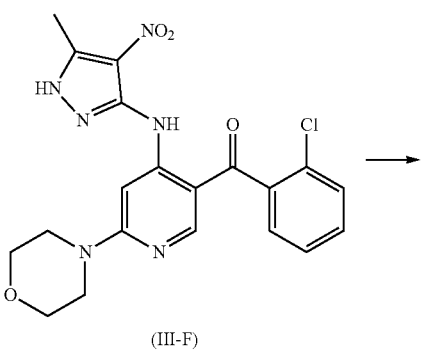

(III-F)

-continued

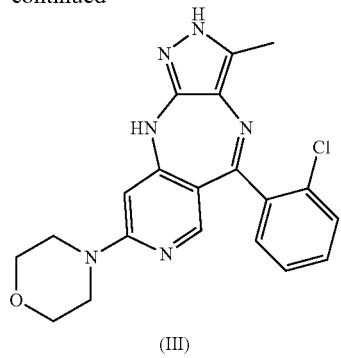

(III)

(2-chlorophenyl)(4-((5-methyl-4-nitro-1H-pyrazol-3-yl)amino)-6-morpholinopyridin-3-yl) methanone (Intermediate III-F) (160 g, crude product) was dissolved in 2-methyltetrahydrofuran (1.6 L), then added with tin dichloride dihydrate (320 g, 1420 mmol). The mixture was heated to 90° C. and reacted for 4 h. LC-MS showed the end of the reaction. After cooling to the room temperature (10° C.), the reaction liquid was poured into saturated sodium hydrogen carbonate solution (4 L), added with 2-methyltetrahydrofuran (1 L), filtered. The filtrate was separated out. The aqueous phase was extracted with 2-methyltetrahydrofuran (1 L). The organic phases were combined, washed with water (2 L) followed by brine (2 L), dried over anhydrous sodium sulfate, concentrated under reduced pressure to obtain the crude product. The crude product was pulped with methyl tert-butyl ether (400 mL) and filtered to give yellow solid (65.0 g, purity 95%), purified by silica gel chromatography (dichloromethane:methanol=20:1) to give pale yellow solid (55 g). The solid was dissolved in DMSO (about 200 mL) and heated to 40-50° C., until the solid was dissolved. The above solution was slowly added dropwise into distilled water (2 L), then a large amount of solid was precipitated, stirred at room temperature overnight, suction filtered. The filter cake was dried in vacuum at 35° C. to give pale yellow powdery solid (53 g, yield 49.9% for three steps).

$^1$H-NMR (400 MHz, DMSO-$d_6$): 11.58 (s, 1H), 8.29 (s, 1H), 7.33-7.47 (m, 4H), 6.90 (s, 1H), 5.96 (s, 1H), 3.61 (m, 4H), 3.31 (m, 4H), 1.98 (s, 3H).

The crystal form of this sample was determined by X-ray powder diffraction, and the crystal form was the same as the crystal form obtained in the preparation methods of Examples 13, 14, 15, and 16, that is, crystal form I.

The present invention can be better understood from the following biological experimental examples. However, those skilled in the art will understand that the description of the experimental examples is only intended to illustrate the invention, and should and will not limit the invention thereto.

Biological Experimental Example 1: Enzymatic Activity Test of the Compound of the Present Invention Test samples: compounds 1 to 4 in the present invention (the sequence numbers and structures thereof are shown in Table 1), dilution concentration: 0.03 μM-3 μM, a total of 10 concentration gradients.

Test method: enzymatic activity tests of Aurora kinase (including Aurora A and Aurora B) and VEGFR2 (KDR) were performed using a multi-function microplate reader.

Experimental Method:

(1) Test for Aurora A Kinase Activity:

Aurora A kinase protein and the compounds were sequentially added to the following reaction system: 8 mM MOPS pH 7.0, 0.2 mM EDTA, 200 μM LRRASLG (Kemptide), 10 mM magnesium acetate and [γ-$^{33}$P]-ATP (radioactive activity was approximately 500 cpm/pmol). Then the above reaction system was added with ATP to start the reaction, and incubated at room temperature for 40 minutes. Then the reaction was terminated by adding a 3% phosphoric acid solution. 10 μL was taken out from the reaction system, and then added dropwise to a P30 filtermat filter membrane, washed three times in 75 mM phosphoric acid solution for 5 minutes, and then washed once with methanol. After the filter membrane was dried, count was performed by a liquid crystal scintillation counter.

(2) Test for Aurora B Kinase Activity:

Aurora B kinase protein and the compounds were sequentially added to the following reaction system: 8 mM MOPS pH 7.0, 0.2 mM EDTA, 30 μM AKRRRLSSLRA, 10 mM magnesium acetate and [γ-$^{33}$P]-ATP (radioactive activity was approximately 500 cpm/pmol). Then the above reaction system was added with ATP to start the reaction, and incubated at room temperature for 40 minutes. Then the reaction was terminated by adding a 3% phosphoric acid solution. 10 μL was taken out from the reaction system, and then added dropwise to a P30 filtermat filter membrane, washed three times in 75 mM phosphoric acid solution for 5 minutes, and then washed once with methanol. After the filter was dried, count was performed by a liquid crystal scintillation counter.

(3) Test for KDR Kinase Activity:

KDR kinase protein and the compounds were sequentially added to the following reaction system: 8 mM MOPS pH 7.0, 0.2 mM EDTA, 0.33 mg/mL myelin basic protein, 10 mM magnesium acetate and [γ-$^{33}$P]-ATP (radioactive activity was approximately 500 cpm/pmol). Then the above reaction system was added with ATP to start the reaction, and incubated at room temperature for 40 minutes. Then the reaction was terminated by adding a 3% phosphoric acid solution. 10 μL was taken out from the reaction system, and then added dropwise to a P30 filtermat filter membrane, washed three times in a 75 mM phosphoric acid solution for 5 minutes, and then washed once with methanol. After the filter was dried, count was performed by a liquid crystal scintillation counter. The test results are shown in Table 2.

TABLE 2

Inhibition activity of Aurora kinase and KDR kinase by compounds 1 to 4 of the present invention (IC$_{50}$)

| | Kinase-inhibiting activity IC$_{50}$ (nM) | | |
|---|---|---|---|
| Test samples | Aurora A | Aurora B | KDR (VEGFR2) |
| Compound 1 | 12 | 30 | 1661 |
| Compound 2 | <3 | 4 | 593 |
| Compound 3 | 4 | 8 | 876 |
| Compound 4 | 4 | 3 | 1517 |

As can be seen from the experimental results in Table 2, the compounds of the present invention have good inhibitory activity against multi-kinases, indicating that the compounds of the present invention have a good clinical application potential in the treatment of diseases mediated by abnormal expression of Aurora kinase (including Aurora A and Aurora B) and VEGFR2 (KDR).

Biological Experimental Example 2: Enzymatic Activity Test of the Compounds of the Present Invention Test samples: Compounds in the present invention (the sequence numbers and structures thereof are shown in Table 1), dilution concentration: 0.03 μM-3 μM, a total of 10 concentration gradients.

Control drug: Compound 1-2 disclosed in WO2013123840A1

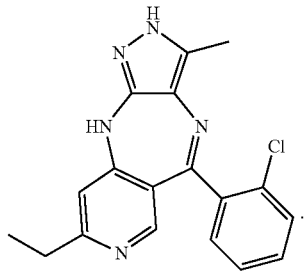 [SMILES: CCc1cc2c(cn1)C(c1ccccc1Cl)=Nc1c(n[nH]c1C)N2]

Test method: enzymatic activity tests of Aurora kinase (including Aurora A and Aurora B) and VEGFR2 (KDR) were performed using a multi-function microplate reader.

Experimental Method:
(1) Preparation for Compound Plate
a) 96-well plates, 10 dose groups, 3-fold serial dilutions, each well was added with DMSO, maximal concentration of 500 μM (50-fold compound).
b) 384-well plates, diluted with 1× kinase buffer (50 mM HEPES, pH 7.5; 0.0015% Brij-35; 2 mM DTT), each well containing 5× compound dissolved in 5 μL of 10% DMSO. Each well of the negative control contains 5 μL of 1× kinase buffer containing 10% DMSO.
(2) Test Procedure
Aurora A, Aurora B and KDR were dissolved in 1× kinase buffer and prepared as a 2.5× enzyme solution. After the compound in various concentrations was reacted with 2.5× enzyme solution at room temperature for 10 min, the FAM-labeled peptide substrate and ATP were added to initiate reaction. After incubation for 40 minutes, 25 μL of terminal solution (100 mM HEPES, pH 7.5; 0.015% Brij-35; 0.2% Coating Reagent #3; 50 mM EDTA) was added to stop the reaction, and the final data were read by Caliper. The test results are shown in Table 3.

TABLE 3

Inhibition activity of Aurora kinase and KDR kinase by compounds of the present invention (IC$_{50}$)

| | Kinase-inhibiting activity IC$_{50}$ (nM) | | |
|---|---|---|---|
| Test samples | Aurora A | Aurora B | KDR (VEGFR2) |
| Control drug 1-2 | 1.6 | 4 | 3.2 |
| Compound 22 | 1.2 | 7.1 | 0.91 |
| Compound 29 | 0.49 | 5.0 | 1.2 |
| Compound 33 | 4.8 | 5.8 | 1.6 |
| Compound 34 | 1.3 | 7.5 | 2.3 |
| Compound 35 | 4.8 | 15 | 8.6 |
| Compound 37 | 5.4 | 8.8 | 1.7 |
| Compound 38 | 18 | 16 | 4.2 |
| Compound 40 | 2.7 | 11 | 2.9 |
| Compound 41 | 15 | 24 | 7.9 |
| Compound 42 | 3.0 | 1.7 | 9.7 |

TABLE 3-continued

Inhibition activity of Aurora kinase and KDR kinase by compounds of the present invention (IC$_{50}$)

| | Kinase-inhibiting activity IC$_{50}$ (nM) | | |
|---|---|---|---|
| Test samples | Aurora A | Aurora B | KDR (VEGFR2) |
| Compound 43 | 2.1 | 5.8 | 1.8 |
| Compound 44 | 0.82 | 6.8 | 1.5 |
| Compound 45 | 1.0 | 4.7 | 0.3 |
| Compound 46 | 0.41 | 3.1 | 0.53 |
| Compound 48 | 1.4 | 5.2 | 1.8 |

As can be seen from the experimental results in Table 3, the compounds of the present invention have good inhibitory activity against multi-kinases, indicating that the compounds of the present invention have a good clinical application potential in the treatment of diseases mediated by abnormal expression of Aurora kinase (including Aurora A and Aurora B) and VEGFR2 (KDR).

Biological Experimental Example 3: Cytological Activity Test of the Compound of the Present Invention Test sample: the compounds of the present invention (the sequence numbers and structures thereof are shown in Table 1).

Control drug: compound 1-2 disclosed in WO2013123840A1

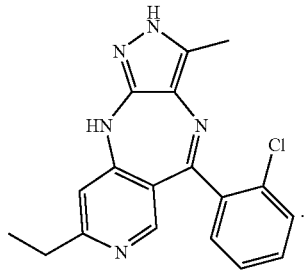 [SMILES: CCc1cc2c(cn1)C(c1ccccc1Cl)=Nc1c(n[nH]c1C)N2]

| Cell strains | Names | Sources | Cell strains | Names | Sources |
|---|---|---|---|---|---|
| OVCAR-8 | ovarian cancer cells | ATCC | Hep3B | liver cancer cells | ATCC |
| OVCAR-3 | ovarian cancer cells | ATCC | KG-1 | Leukemic cells | ATCC |
| Caov-3 | ovarian cancer cells | ATCC | Kasumi-1 | Leukemic cells | ATCC |
| A2780 | ovarian cancer cells | CEACC | BT-549 | breast cancer cells | ATCC |
| TOV-112D | ovarian cancer cells | ATCC | MDA-MB-468 | breast cancer cells | ATCC |
| D4475 | breast cancer cells | ATCC | A549 | Lung cancer cells | ATCC |
| HCC1954 | breast cancer cells | ATCC | HCC38 | breast cancer cells | ATCC |

-continued

| Cell strains | Names | Sources | Cell strains | Names | Sources |
|---|---|---|---|---|---|
| HCC70 | breast cancer cells | ATCC | | | |

Test method: The effect of compounds on cell proliferation of different cell lines was examined by Cell Titer-Glo method.

Experimental Method:

Each cell line was inoculated into a 96-well plate one day in advance, and after overnight incubation, drugs in different concentrations were added to a final concentration of 0-10000 nM, 3-5 folds dilution, for a total of 10 concentration points. After incubation for 72 hours, the mixture was added with Cell titer-Glo reagent equilibrated at room temperature, and shaken to incubation for 10 min, and then allowed to stand at room temperature for 2 min to stabilize the light signal. The multi-function microplate reader was used to read data from each well and analyze it. The test results are shown in Table 4-5:

TABLE 4

Cellular inhibitory activity IC$_{50}$ (nM) of the compounds of the invention

| Test samples | OVCAR-8 | OVCAR-3 | Capv-3 | A2780 | TOV-112D | Hep3B | KG-1 | Kasumi-1 |
|---|---|---|---|---|---|---|---|---|
| Control drug 1-2 | 613 | 814 | 365 | 650 | 2507 | 244 | 452 | 126 |
| Compound 22 | 433 | 752 | 146 | 34 | 650 | 67 | 5 | 19 |
| Compound 29 | 305 | 307 | 184 | 35 | 955 | 50 | 5 | 48 |
| Compound 34 | — | — | — | — | — | — | 45 | 81 |
| Compound 35 | 620 | 266 | 266 | — | — | — | — | 80 |

TABLE 5

Cellular inhibitory activity IC$_{50}$ (nM) of the compounds of the invention

| Test samples | BT-549 | MDA-MB-468 | A549 | D4475 | HCC1954 | HCC38 | HCC70 |
|---|---|---|---|---|---|---|---|
| Control drug1-2 | 654 | 1376 | 1377 | 443 | 894 | 1100 | 1515 |
| Compound 29 | 170 | — | 322 | 113 | 396 | — | — |
| Compound 33 | 421 | — | — | — | 538 | 700 | 866 |
| Compound 35 | 509 | 1034 | 578 | — | 732 | — | — |
| Compound 44 | 249 | 984 | 358 | 101 | — | — | — |
| Compound 45 | 186 | 491 | 507 | 171 | — | — | — |
| Compound 46 | 83 | 319 | 211 | 48 | — | — | — |

"—" means untested.

As can be seen from the results of the experiments in Tables 4-5, the compounds of the present invention have good inhibitory activity against various cancer cells and can be used for the treatment of corresponding cancer diseases.

Biological Experimental Example 4: Determination of Enzymatic Activity of Crystal Form I of Compound of Formula (III) (Compound 29)

Test sample: crystal form I prepared in Example 13, dilution concentration: 0.03 μM-3 μM, a total of 10 concentration gradients.

Test method: The enzymatic activity test of the kinases shown in Table 1 was carried out using a multi-function microplate reader.

Experimental Method:

(1) Preparation for Compound Plate a) 96-well plates, 10 dose groups, 3-fold serial dilutions, DMSO is added to each well, up to a concentration of 500 μM (50× compound).

b) 384-well plates, diluted with 1× kinase buffer (50 mM HEPES, pH 7.5; 0.0015% Brij-35; 2 mM DTT), each well containing 5× compound dissolved in 5 μL of 10% DMSO. Each well of the negative control contain 5 μL of 1× kinase buffer containing 10% DMSO.

(2) Test Procedure

The kinases shown in Table 6 were dissolved in 1× kinase buffer and prepared as 2.5× enzyme solution, respectively.

After crystal form I and the 2.5× enzyme solution was reacted at room temperature for 10 min, the FAM-labeled peptide substrate and ATP were added to initiate reaction. After incubation for 40 minutes, 25 μL of terminal solution (100 mM HEPES, pH 7.5; 0.015% Brij-35; 0.2% Coating Reagent #3; 50 mM EDTA) was added to stop the reaction. The final data was read by Caliper. The test results are shown in Table 6.

TABLE 6

Determination of the kinase inhibitory activity of the crystal form I of the compound of formula (III) (IC$_{50}$)

| | Kinase-inhibiting activity IC$_{50}$ (nM) | | | | | | |
|---|---|---|---|---|---|---|---|
| Test sample | Aurora A | Aurora B | KDR (VEGFR2) | FLT1 | JAK2 | FGFR1 | FGFR3 |
| Crystal form I | 1.2 | 3.3 | 2.5 | 2.4 | 0.75 | 2.3 | 3.5 |

From the experimental results in Table 6, the crystal form I of the compound of formula (III) of the present invention has good inhibitory activity against a variety of kinases, indicating the compounds of the present invention have a good clinical application potential in the treatment of diseases mediated by abnormal expression of various kinases, such as Aurora, VEGFR2 (KDR), FGFR, FLT, and JAK.

Biological Experimental Example 5: In Vivo Pharmacodynamic Study of the Compound of the Present Invention on a Subcutaneous Xenograft Tumor Model of Human Acute Granulocytic Leukemia Kasumi-1 Cells Test sample: crystal form I prepared in Example 17 (crystal form I of compound 29)

Animals, Cells, Reagents & Instruments: Kasumi-1 cells, derived from ATCC.

CB17 SCID mice, 6-8 weeks, female, available from Shanghai Lingchang Biotechnology Co., Ltd.

Experimental Method:

1. Construction and Grouping of Tumor-Bearing Mice

Kasumi-1 cells were cultured in vitro in a single layer, and culture conditions were as follows: RPMI1640 medium supplemented with 10% heat-inactivated fetal bovine serum and 1% penicillin-streptomycin double antibody, 37° C., and 5% $CO_2$. Passage was achieved two to three times a week. When the cells were in the exponential growth phase, the cells were harvested, counted, and inoculated.

0.2 mL of cell suspension containing about $1 \times 10^7$ Kasumi-1 cells (cell suspended in 1:1 base RPMI 1640 medium and nutrient gel) was subcutaneously inoculated into the right back of female CB17 SCID mice. Grouping administration was started when the average tumor volume reached 100-150 $mm^3$. Grouping method: Animals were weighed prior to administration and tumor volume was measured. Grouping was performed according to the tumor volume, with 8 mice per group.

2. Dosage Regimen

TABLE 7

Dosage regimen

| Compound | Dose (mg/kg) | Dose Volume (µL/g) | Number of animals | Administration route | Schedule for administration |
|---|---|---|---|---|---|
| Solvent | — | — | 8 | po | QD × 18 |
| Crystal form I of compound 29 | 5 | 10 | 8 | po | QD × 18 |
| Crystal form I of compound 29 | 15 | 10 | 8 | po | QD × 18 |

3. Experimental Observation Indicators

Health and death of the animals were monitored daily. Body weight was measured twice a week, and samples were collected after the last dose and the tumor weight was weighed. The efficacy regarding tumor weight was evaluated by TGI %, tumor growth inhibition (TGI) %=(TWc–TW$_T$)/TWc×100%, TWc: tumor weight of control group, TWT: tumor weight of treatment group. According to the NIH guidelines, the drug is considered effective if TGI ≥58%.

TABLE 8

Effect on tumor weight of Kasumi-1 tumor-bearing mice

| Groups | Therapeutic drug | Doses (mg/kg) | Tumor Weight (g) | Tumor Growth Inhibition rate (TGI)$^a$ |
|---|---|---|---|---|
| Solvent po, QD × 18 | 0.5% CMC-Na | — | 1.430 ± 0.218 | — |
| Crystal form I of compound 29 po, QD × 18 | Compound 29 | 5 | 0.435 ± 0.091 | 69.58 |
| Crystal form I of compound 29 po, QD × 18 | Compound 29 | 15 | 0.100 ± 0.014 | 92.98 |

Note:
$^a$tumor growth inhibition (TGI)% = (TWc – TWT)/TWc × 100%, TWc: tumor weight of control group, TW$_T$: tumor weight of treatment group. The compound is effective if TGI ≥ 58%.
QD: Once a day.
Po: Oral administration.

From the experimental results in Table 8, it can be seen that compound 29 (crystal form I) has a significant inhibitory effect on the Kasumi-1 cell xenograft model, indicating that the compound of the present invention has a good clinical application potential for acute leukemia.

Example 6: PK Evaluation of Beagle Dogs of the Present Invention

Test sample: crystal form I prepared in Example 17 (crystal form I of compound 29)

Experimental Method:

1. The Administration and Blood Sample Collection (1) Administration to animals: All animals were fasted for more than 12 h before administration, and fed at 4 h after the administration. Water was not limited before and after the administration during the experiment. Beagle dogs were given intravenously 1 mg/kg of crystal form I of compound 29 (prescription: 10% DMA+20% (30% Solutol)+70% saline) in a single dose, and blood was collected at 0 h before administration and 0.083, 0.25, 0.50, 1.0, 2.0, 4.0, 6.0, 8.0, 12 and 24 h after administration. Beagle dogs were given orally 2 mg/kg of crystal form I of compound 29 (Prescription: 10% DMA+20% (30% Solutol)+70% saline) in a single dose, and blood was collected at 0 h before administration and at 0.25, 0.50, 1.0, 2.0, 4.0, 6.0, 8.0, 12, and 24 h after administration, and 200 µL blood was taken through a small saphenous vein, and placed in a dried EDTA-K2 test tube.

(2) Preparation of plasma: The whole blood sample was separated by low-speed centrifugation (1800 g, 5 min, 4° C.) (the whole blood was collected and placed in an ice bath, and plasma separation should be completed within 30 min) to give plasma, and the separated plasma was stored in a refrigerator at −20° C. for analysis.

2. Sample Analysis Method

The sample to be tested (−80° C.) was taken from the refrigerator, thawed naturally at room temperature and vortexed for 5 min; 20 µL of plasma sample was accurately aspirated into a 1.5 mL centrifuge tube; added with 200 µL of internal standard working solution at a concentration of 50 ng/mL, and mixed well; after vortexed for 5 min, the mixture was centrifuged for 5 min (12000 rpm); 50 µL of supernatant was accurately aspirated into 96-well plates pre-filled with 150 µL/well of water; vortexed for 5 min, LC-MS/MS determination was performed in an injection volume of 15 µL.

3. Data Processing Method

The concentration of test sample was output using Analyst 1.6.1 from AB SCIEX. Microsoft Excel is used to calculate the mean, standard deviation, coefficient of variation and other parameters (data directly output by Analyst 1.6.1 is not calculated), PK parameters were calculated using Pharsight Phoenix 6.1 software NCA.

Experimental Results:

TABLE 9

PK parameters in beagle dogs

| Compound | $t_{1/2}$ iv/ $t_{1/2}$po (h) | $V_{z\_obs}$ iv (L/kg) | $Cl_{obs}$ iv (L/h/kg) | $T_{max}$ po (h) | $AUC_{inf}$iv/ $AUC_{inf}$po (h * ng/mL) | F % |
|---|---|---|---|---|---|---|
| Crystal form I of Compound 29 | 7.64/ 6.87 | 2.35 | 0.22 | 2.0 | 4654/8598 | 92.4 |

It can be seen from the experimental results in Table 9 that compound 29 (crystal form I) has good pharmacokinetic properties in Beagle dogs, shows very good druggability, and has a very large clinical application potential.

The above is only the preferred embodiments of the present invention, and is not intended to limit the present invention. Any modifications, equivalent replacements and improvements, etc., made within the spirit and scope of the invention are intended to be included within the scope of the invention.

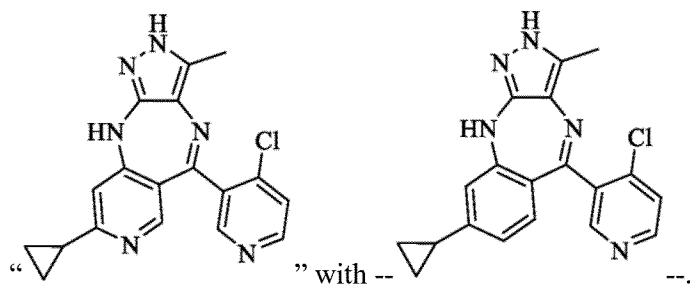

The invention claimed is:

1. A compound represented by formula (I), pharmaceutically acceptable salts or stereoisomers thereof,

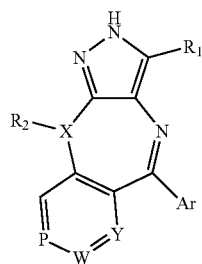

(I)

wherein,

X is selected from CH or N;

$R_1$ is selected from the group consisting of hydrogen, $C_{1-6}$ alkyl, $C_{3-6}$ cycloalkyl, $C_{1-6}$ alkoxy, halogenated $C_{1-6}$ alkyl and halogenated $C_{1-6}$ alkoxy;

$R_2$ is selected from the group consisting of hydrogen, $C_{1-6}$ alkyl and $C_{3-6}$ cycloalkyl;

Y is selected from $CR_3$ or N;

P is selected from $CR_4$ or N;

W is selected from $CR_5$ or N;

$R_3$, $R_4$ and $R_5$ are independently selected from the group consisting of hydrogen, hydroxy, carboxy, cyano, nitro, halogen, $C_{1-6}$ alkyl, $C_{1-6}$ alkoxy, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, —$NR_{11}$—$(CH_2)_n$—$N(R_7)(R_8)$, $C_{1-6}$ alkylthio-$(CH_2)_n$—, —$(CH_2)_n$-(3-14) membered cycloalkyl, —$(CH_2)_n$-(6-14) membered aryl, —$(CH_2)_n$-(5-14) membered heterocyclyl, and —$(CH_2)_n$-(5-14) membered heteroaryl; wherein, n=0-6; the ring-forming S atom in cycloalkyl, aryl, heterocyclyl or heteroaryl can be optionally oxidized to S(O) or $S(O)_2$, the ring-forming C atom in cycloalkyl, aryl, heterocyclyl or heteroaryl can be optionally oxidized to C(O); and the cycloalkyl, aryl, heteroaryl or heterocyclyl can be optionally substituted with one or more independent $C_{1-3}$ alkyl or $C_{3-6}$ cycloalkyl;

$R_7$ and $R_8$ are independently selected from the group consisting of hydrogen, $C_{1-6}$ alkyl, $C_{3-6}$ cycloalkyl, $C_{1-6}$ alkoxy, halogenated $C_{1-6}$ alkyl, and halogenated $C_{1-6}$ alkoxy; and P, W, and Y are not N simultaneously, when Y is $CR_3$, P is $CR_4$, and W is N, $R_4$ cannot be $C_{1-6}$ alkyl, and when $R_4$ is hydrogen, $R_3$ cannot be $C_{1-6}$ alkyl;

when Y is $CR_3$, P is $CR_4$, and W is $CR_5$, one of $R_4$ and $R_5$ must be H, and when $R_4$ is H, $R_5$ is selected from the group consisting of hydroxy, carboxy, $C_{1-6}$ alkyl, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{3-8}$ cycloalkylsulfonyl, $C_{1-6}$ alkylcarbonyl, $C_{3-6}$ cycloalkylcarbonyl, —$NR_{11}$—$(CH_2)_n$—$N(R_7)(R_8)$, $C_{1-6}$ alkylthio-$(CH_2)_n$—, —$(CH_2)_n$-(3-14) membered cycloalkyl, —$(CH_2)_n$-(6-14) membered aryl, —$(CH_2)_n$-(5-14) membered heterocyclyl, and —$(CH_2)_n$-(5-14) membered heteroaryl; wherein, n=0-6; the ring-forming S atom in cycloalkyl, aryl, heterocyclyl or heteroaryl can be optionally oxidized to S(O) or $S(O)_2$, the ring-forming C atom in cycloalkyl, aryl, heterocyclyl or heteroaryl can be optionally oxidized to C(O); and the cycloalkyl, aryl, heteroaryl or heterocyclyl can be optionally substituted with one or more independent $C_{1-3}$ alkyl or $C_{3-6}$ cycloalkyl;

when $R_5$ is H, $R_4$ is selected from the group consisting of hydroxy, carboxy, cyano, nitro, halogen, $C_{1-6}$ alkyl, $C_{1-6}$ alkoxy, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, —$NR_{11}$—$(CH_2)_n$—$N(R_7)(R_8)$, $C_{1-6}$ alkylthio-$(CH_2)_n$—$(CH_2)_n$-(3-14) membered cycloalkyl, —$(CH_2)_n$-(6-14) membered aryl, —$(CH_2)_n$-(5-14) membered heterocyclyl, and —$(CH_2)_n$-(5-14) membered heteroaryl; wherein, n=0-6; the ring-forming S atom in cycloalkyl, aryl, heterocyclyl or heteroaryl can be optionally oxidized to S(O) or $S(O)_2$, the ring-forming C atom in cycloalkyl, aryl, heterocyclyl or heteroaryl can be optionally oxidized to C(O); and the cycloalkyl, aryl, heteroaryl or heterocyclyl can be optionally substituted with one or more independent $C_{1-3}$ alkyl or $C_{3-6}$ cycloalkyl;

Ar is selected from the group consisting of 3-14 membered cycloalkyl, 6-14 membered aryl, 5-14 membered heterocyclyl and 5-14 membered heteroaryl, the ring-forming S atom in cycloalkyl, aryl, heterocyclyl or heteroaryl can be optionally oxidized to S(O) or $S(O)_2$, the ring-forming C atom in cycloalkyl, aryl, heterocyclyl or heteroaryl can be optionally oxidized to C(O), and Ar can be optionally substituted with 1 to 3 $R_6$;

$R_6$ is each independently selected from the group consisting of hydrogen, hydroxy, amino, carboxy, cyano, nitro, halogen, $C_{1-6}$ alkyl, $C_{3-6}$ cycloalkyl, $C_{1-6}$ alkoxy, $C_{3-6}$ cycloalkyloxy, halogenated $C_{1-6}$ alkoxy, halogenated $C_{1-6}$ alkyl, $C_{3-6}$ cycloalkyl, $C_{2-8}$ alkenyl, $C_{2-8}$ alkynyl, —$NR_{11}$—$(CH_2)_n$—$N(R_9)(R_{10})$, amino $C_{1-6}$ alkyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, $C_{1-6}$ alkylthio, —$(CH_2)_n$-(6-14) membered cycloalkyl, —$(CH_2)_n$-(6-14) membered aryl, —$(CH_2)_n$-(5-14) membered heterocyclyl and —$(CH_2)_n$-(5-14) membered heteroaryl; wherein, n=0-6, and cycloalkyl, aryl, heteroaryl, heterocyclyl can be optionally substituted with one or more independent $C_{1-3}$ alkyl;

$R_9$ and $R_{10}$ are independently selected from the group consisting of hydrogen, $C_{1-6}$ alkyl, $C_{3-6}$ cycloalkyl, $C_{1-6}$ alkoxy, halogenated $C_{1-6}$ alkyl, and halogenated $C_{1-6}$ alkoxy; and $R_{11}$ is selected from the group consisting of hydrogen, $C_{1-6}$ alkyl and $C_{3-6}$ cycloalkyl.

2. The compound, pharmaceutically acceptable salts or stereoisomers thereof according to claim 1, wherein, X is N;

$R_1$ is $C_{1-3}$ alkyl;

$R_2$ is selected from the group consisting of hydrogen, methyl and ethyl;

Y is selected from $CR_3$ or N;

P is selected from $CR_4$ or N;

W is selected from $CR_5$ or N;

$R_3$, $R_4$ and $R_5$ are independently selected from the group consisting of hydrogen, hydroxy, carboxy, cyano, nitro, halogen, $C_{1-6}$ alkyl, $C_{1-6}$ alkoxy, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, —$NR_{11}$—$(CH_2)_n$—$N(R_7)(R_8)$, $C_{1-6}$ alkylthio-$(CH_2)_n$—, —$(CH_2)_n$-(3-14) membered cycloalkyl, —$(CH_2)_n$-(6-14) membered aryl, —$(CH_2)_n$-(5-14) membered heterocyclyl, and —$(CH_2)_n$-(5-14) membered heteroaryl; wherein, n=0-6; the ring-forming S atom in cycloalkyl, aryl, heterocyclyl or heteroaryl can be optionally oxidized to S(O) or $S(O)_2$, and the ring-forming C atom in cycloalkyl, aryl, heterocyclyl or heteroaryl can be optionally oxidized to C(O); the cycloalkyl, aryl, heteroaryl or heterocyclyl can be optionally substituted with one or more independent $C_{1-3}$ alkyl or $C_{3-6}$ cycloalkyl;

$R_7$ and $R_8$ are independently selected from the group consisting of hydrogen, $C_{1-6}$ alkyl, $C_{3-6}$ cycloalkyl, $C_{1-6}$ alkoxy, halogenated $C_{1-6}$ alkyl and halogenated $C_{1-6}$ alkoxy; and P, W, and Y are not N simultaneously, when Y is $CR_3$, P is $CR_4$, and W is N, $R_4$ cannot be $C_{1-6}$ alkyl, and when $R_4$ is hydrogen, $R_3$ cannot be $C_{1-6}$ alkyl;

when Y is $CR_3$, P is $CR_4$, and W is $CR_5$, one of $R_4$ and $R_5$ must be H, and when $R_4$ is H, $R_5$ is selected from the group consisting of hydroxy, carboxy, $C_{1-6}$ alkyl, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{3-8}$ cycloalkylsulfonyl, $C_{1-6}$ alkylcarbonyl, $C_{3-6}$ cycloalkylcarbonyl, —$NR_{11}$—$(CH_2)_n$—$N(R_7)(R_8)$, $C_{1-6}$ alkylthio-$(CH_2)_n$—$(CH_2)_n$-(3-14) membered cycloalkyl, —$(CH_2)_n$-(6-14) membered aryl, —$(CH_2)_n$-(5-14) membered heterocyclyl, and —$(CH_2)_n$-(5-14) membered heteroaryl; wherein, n=0-6; the ring-forming S atom in cycloalkyl, aryl, heterocyclyl or heteroaryl can be optionally oxidized to S(O) or $S(O)_2$, the ring-forming C atom in cycloalkyl, aryl, heterocyclyl or heteroaryl can be optionally oxidized to C(O); and the cycloalkyl, aryl, heteroaryl or heterocyclyl can be optionally substituted with one or more independent $C_{1-3}$ alkyl or $C_{3-6}$ cycloalkyl;

when $R_5$ is H, $R_4$ is selected from the group consisting of hydroxy, carboxy, cyano, nitro, halogen, $C_{1-6}$ alkyl, $C_{1-6}$ alkoxy, $C_{3-6}$ cycloalkyloxy, oxa $C_{5-8}$ cycloalkyloxy, halogenated $C_{1-6}$ alkoxy, $C_{2-8}$ alkenyl, $C_{2-8}$ alkynyl, $C_{3-6}$ cycloalkylamino, $C_{1-6}$ alkylsulfonyl, $C_{3-8}$ cycloalkylsulfonyl, $C_{1-6}$ alkylcarbonyl, $C_{3-6}$ cycloalkylcarbonyl, —$NR_{11}$—$(CH_2)_n$—$N(R_7)(R_8)$, $C_{1-6}$ alkylthio-$(CH_2)_n$—$(CH_2)_n$-(3-14) membered cycloalkyl, —$(CH_2)_n$-(6-14) membered aryl, —$(CH_2)_n$-(5-14) membered heterocyclyl, and —$(CH_2)_n$-(5-14) membered heteroaryl; wherein, n=0-6; the ring-forming S atom in cycloalkyl, aryl, heterocyclyl or heteroaryl can be optionally oxidized to S(O) or $S(O)_2$, the ring-forming C atom in cycloalkyl, aryl, heterocyclyl or heteroaryl can be optionally oxidized to C(O); and the cycloalkyl, aryl, heteroaryl or heterocyclyl can be optionally substituted with one or more independent $C_{1-3}$ alkyl or $C_{3-6}$ cycloalkyl;

$R_{11}$ is selected from the group consisting of hydrogen, $C_{1-6}$ alkyl and $C_{3-6}$ cycloalkyl;

Ar is selected from the group consisting of 6-14 membered aryl or 5-10 membered heteroaryl; the ring-forming S atom in aryl and heteroaryl can be optionally oxidized to S(O) or $S(O)_2$, and the ring-forming C atom in aryl and heteroaryl can be optionally oxidized to C(O), wherein Ar can be optionally substituted with 1 to 3 $R_6$; and $R_6$ is each independently selected from the group consisting of hydrogen, amino, cyano, halogen, $C_{1-4}$ alkyl, trifluoromethyl, methylsulfonyl, —$(CH_2)_n$-(5-10) membered heterocyclyl, and —$(CH_2)_n$-(5-10) membered heteroaryl; wherein, n=0-6; and the heteroaryl and heterocyclyl can be optionally substituted with one or more independent $C_{1-3}$ alkyl.

3. The compound, pharmaceutically acceptable salts or stereoisomers thereof according to claim 2, wherein the compound is represented by formula (II):

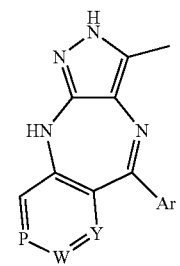

(II)

wherein,

Ar is selected from the group consisting of 6 membered aryl and 5-6 membered heteroaryl, the ring-forming S atom in aryl and heteroaryl can be optionally oxidized to S(O) or $S(O)_2$, the ring-forming C atom in aryl and heteroaryl can be optionally oxidized to C(O), wherein Ar can be optionally substituted with 1 to 3 $R_6$;

$R_6$ is each independently selected from the group consisting of hydrogen, amino, cyano, halogen, $C_{1-4}$ alkyl, trifluoromethyl, and methylsulfonyl;

Y is selected from $CR_3$ or N;

P is selected from $CR_4$ or N;

W is selected from $CR_5$ or N;

$R_3$, $R_4$ and $R_5$ are independently selected from the group consisting of hydrogen, hydroxy, carboxy, cyano, nitro, halogen, $C_{1-4}$ alkyl, $C_{1-4}$ alkoxy, $C_{3-6}$ cycloalkyloxy, oxa C$_{5-8}$ cycloalkyloxy, halogenated C$_{1-4}$ alkoxy, C$_{2-6}$ alkenyl, C$_{2-6}$ alkynyl, C$_{3-6}$ cycloalkylamino, C$_{1-4}$ alkylsulfonyl, C$_{3-8}$ cycloalkylsulfonyl, C$_{1-4}$ alkylcarbonyl, C$_{3-6}$ cycloalkylcarbonyl, —NR$_{11}$—(CH$_2$)$_n$—N(R$_7$)(R$_8$), —(CH$_2$)$_n$-(3-14) membered cycloalkyl, —(CH$_2$)$_n$-(5-11) membered heterocyclyl and —(CH$_2$)$_n$-(5-10) membered heteroaryl; wherein, n=0-6; the ring-forming S atom in cycloalkyl, heterocyclyl or heteroaryl can be optionally oxidized to S(O) or S(O)$_2$, and the ring-forming C atom in cycloalkyl, heterocyclyl or heteroaryl can be optionally oxidized to C(O); and the cycloalkyl, heteroaryl, and heterocyclyl can be optionally substituted with one or more independent C$_{1-3}$ alkyl or C$_{3-6}$ cycloalkyl;

R$_7$ and R$_8$ are independently selected from the group consisting of hydrogen, methyl, ethyl, isopropyl, and cyclopropyl; and P, W, and Y are not N simultaneously, and at least one of P, W, and Y is N;

when Y is CR$_3$, P is CR$_4$, and W is N, R$_4$ cannot be C$_{1-4}$ alkyl, and when R$_4$ is hydrogen, R$_3$ cannot be C$_{1-4}$ alkyl; and R$_{11}$ is selected from the group consisting of hydrogen, C$_{1-6}$ alkyl, and C$_{3-6}$ cycloalkyl.

4. The compound, pharmaceutically acceptable salts or stereoisomers thereof according to claim 1, wherein,
Ar can be selected from the group consisting of:

Y is selected from CR$_3$ or N;
P is selected from CR$_4$ or N;
W is selected from CR$_5$ or N;
R$_3$, R$_4$ and R$_5$ are independently selected from the group consisting of: hydrogen, methyl, ethyl, isopropyl,

87

-continued

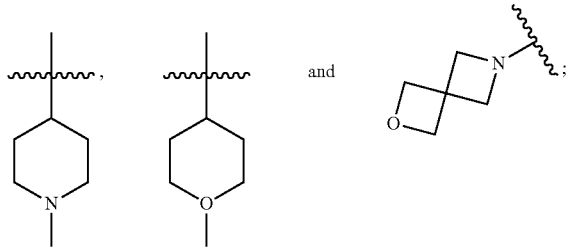

and

P, W, and Y are not N simultaneously, and at least one of P, W, and Y is N;

when Y is $CR_3$, P is $CR_4$, and W is N, $R_4$ cannot be methyl, ethyl or isopropyl, and when $R_4$ is hydrogen, $R_3$ cannot be methyl, ethyl or isopropyl.

5. The compound, pharmaceutically acceptable salts or stereoisomers thereof according to claim 3, wherein, Y is $CR_3$;

P is $CR_4$;

W is N;

$R_4$ cannot be $C_{1-4}$ alkyl, and when $R_4$ is hydrogen, $R_3$ cannot be $C_{1-4}$ alkyl.

6. The compound, pharmaceutically acceptable salts or stereoisomers thereof according to claim 3, wherein, Ar is selected from phenyl or 5-6 membered heteroaryl; Ar can be optionally substituted with 1 to 3 $R_6$, $R_6$ is each independently selected from the group consisting of hydrogen, amino, cyano, halogen, $C_{1-4}$ alkyl, trifluoromethyl, and methylsulfonyl;

Y is $CR_3$;

P is $CR_4$;

W is N;

$R_3$ is selected from hydrogen or $C_{1-4}$ alkyl;

$R_4$ is selected from the group consisting of hydrogen, hydroxy, carboxy, cyano, nitro, halogen, $C_{1-4}$ alkoxy, $C_{3-6}$ cycloalkyloxy, oxa $C_{5-8}$ cycloalkyloxy, halogenated $C_{1-4}$ alkoxy, $C_{3-6}$ cycloalkylamino, $C_{1-4}$ alkylsulfonyl, $C_{3-6}$ cycloalkylsulfonyl, $C_{1-4}$ alkylcarbonyl, $C_{3-6}$ cycloalkylcarbonyl, $-NR_{11}-(CH_2)_n-N(R_7)(R_8)$, $-(CH_2)_n-C_{3-10}$ cycloalkyl, $-(CH_2)_n$-(5-11) membered heterocyclyl, and $-(CH_2)_n$-(5-10) membered heteroaryl; wherein, n=0-6; the ring-forming S atom in cycloalkyl, heterocyclyl or heteroaryl can be optionally oxidized to S(O) or S(O)$_2$, and the ring-forming C atom in cycloalkyl, heterocyclyl or heteroaryl can be optionally oxidized to C(O); and the cycloalkyl, heteroaryl, heterocyclyl can be optionally substituted with one or more independent $C_{1-3}$ alkyl or $C_{3-6}$ cycloalkyl, and when $R_4$ is hydrogen, $R_3$ cannot be $C_{1-4}$ alkyl.

7. The compound, pharmaceutically acceptable salts or stereoisomers thereof according to claim 6, wherein Ar is selected from phenyl or pyridyl; Ar can be optionally substituted with 1 to 3 $R_6$, wherein $R_6$ is each independently selected from the group consisting of hydrogen, amino, cyano, halogen, $C_{1-4}$ alkyl, trifluoromethyl, and methylsulfonyl;

Y is $CR_3$;

P is $CR_4$;

W is N;

$R_3$ is selected from hydrogen or $C_{1-4}$ alkyl;

$R_4$ is selected from the group consisting of hydrogen, hydroxy, carboxy, cyano, nitro, halogen, $C_{1-4}$ alkoxy, $C_{3-6}$ cycloalkyloxy, halogenated $C_{1-4}$ alkoxy, $C_{3-6}$ cycloalkylamino, $C_{1-4}$ alkylsulfonyl, $C_{1-4}$ alkylcarbonyl, $C_{3-6}$ cycloalkylcarbonyl, $-NR_{11}-(CH_2)_n-N(R_7)(R_8)$, $-(CH_2)_n-C_{3-6}$ cycloalkyl, $-(CH_2)_n$-(5-6) membered monoheterocyclyl, $-(CH_2)_n$-(7-11) membered fused heterocyclyl, $-(CH_2)_n$-(5-6) monoheteroaryl, and $-(CH_2)_n$-(8-10) membered fused heteroaryl; wherein, n=0-6; the ring-forming S atom in cycloalkyl, heterocyclyl or heteroaryl can be optionally oxidized to S(O) or S(O)$_2$, and the ring-forming C atom in cycloalkyl, heterocyclyl or heteroaryl can be optionally oxidized to C(O); and the cycloalkyl, heteroaryl, and heterocyclyl can be optionally substituted with one or more independent $C_{1-3}$ alkyl or $C_{3-6}$ cycloalkyl, and when $R_4$ is hydrogen, $R_3$ cannot be $C_{1-4}$ alkyl.

8. The compound, pharmaceutically acceptable salts or stereoisomers thereof according to claim 1, wherein the compound is selected from:

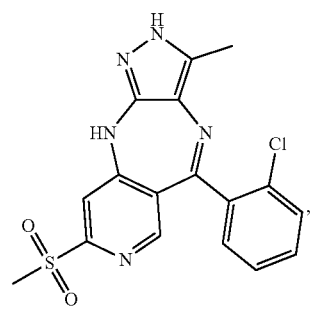

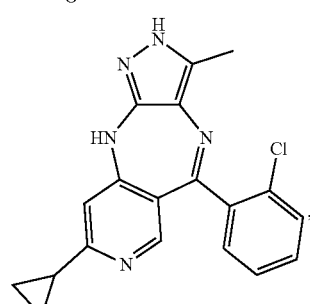

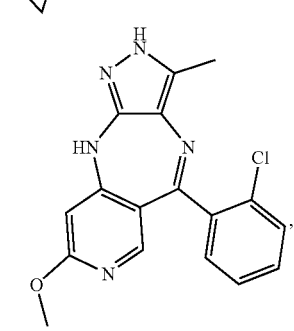

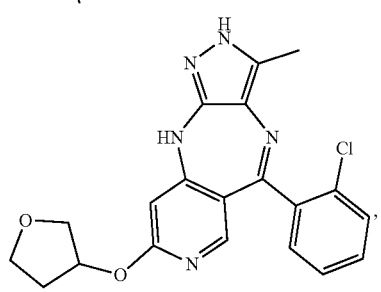

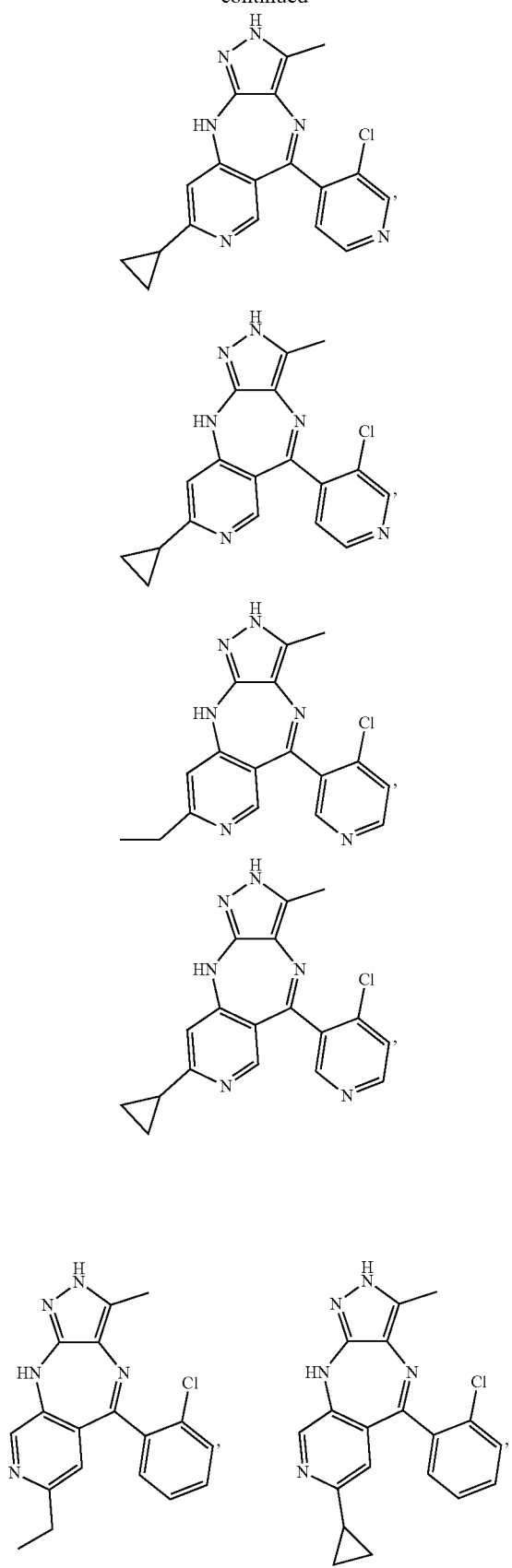
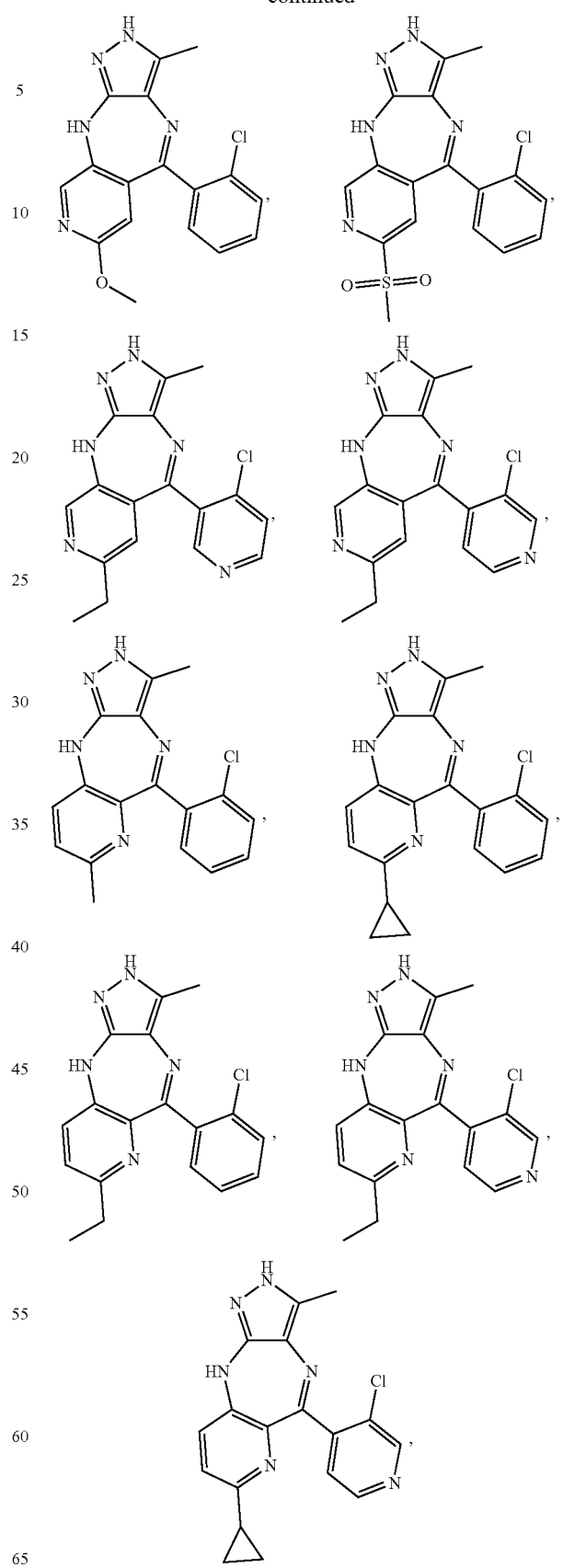

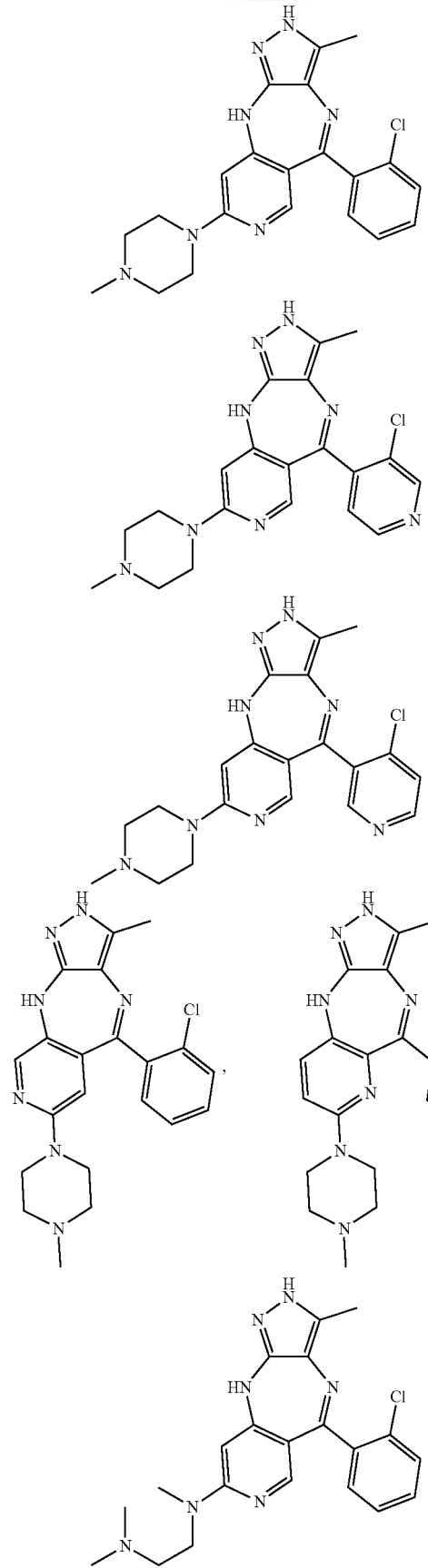
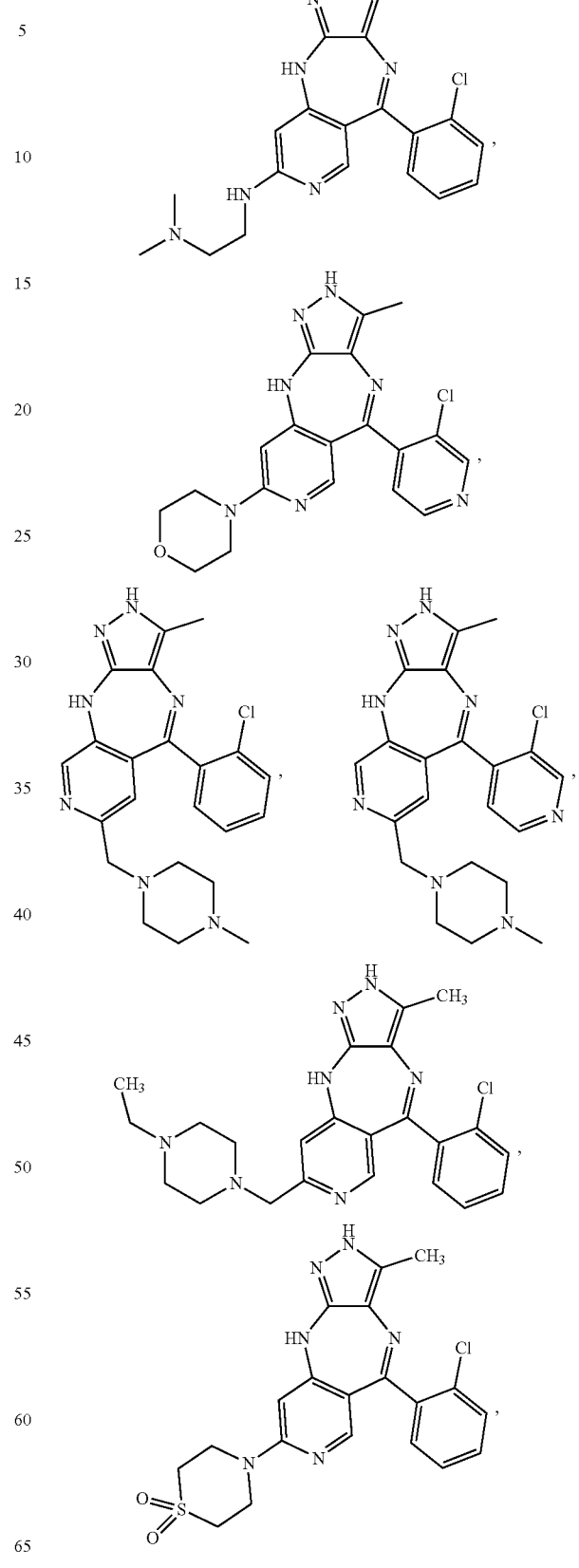

93
-continued
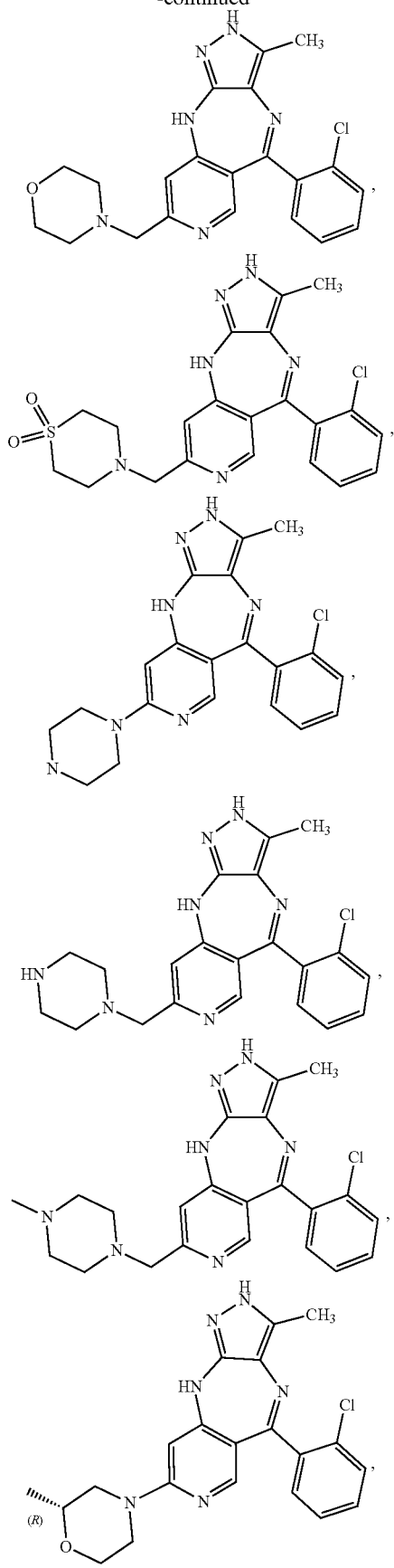
94
-continued
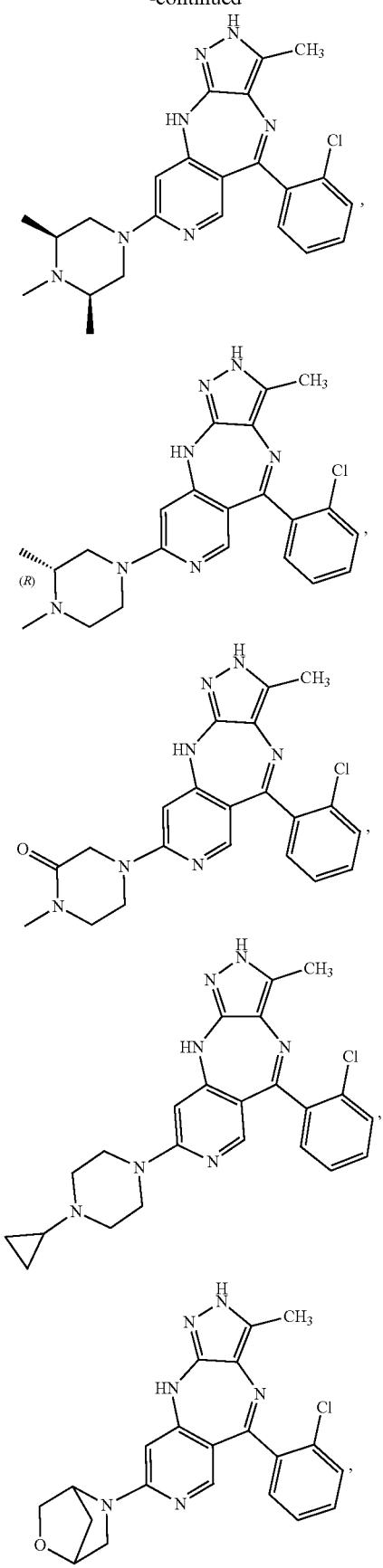

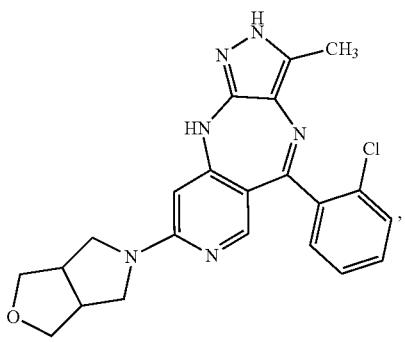,

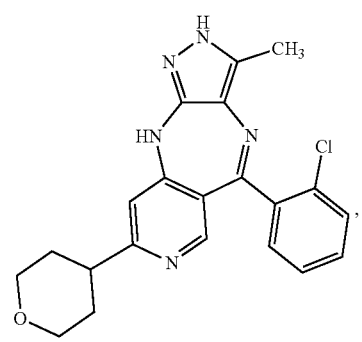,

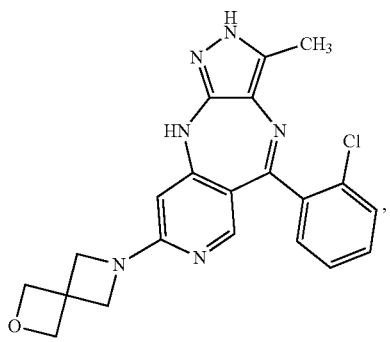,

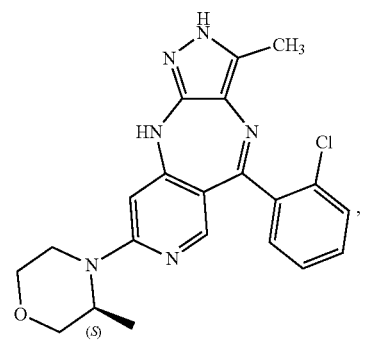,

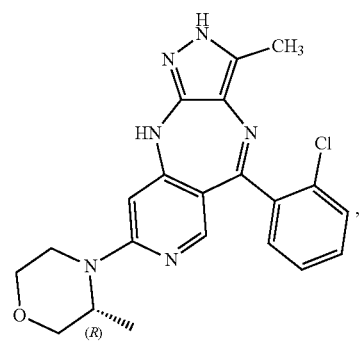,

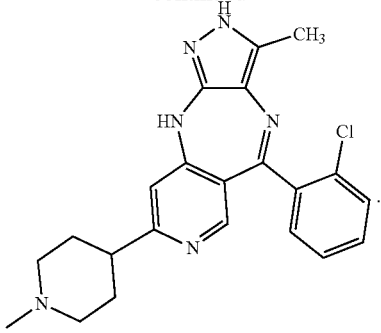.

9. A crystal form I of a compound of formula (III), 4-(5-(2-chlorophenyl)-3-methyl-2,10-dihydropyrazolo[4,3-b]pyrido[4,3-e][1,4]diazepin-8-yl)morpholine, wherein the crystal form I has characteristic peaks at 7.4±0.2°, 17.9±0.2°, 18.9±0.2°, 19.4±0.2°, 21.5±0.2° and 23.7±0.2° in X-ray powder diffraction pattern; and the characteristic peak is expressed by 2θ angle;

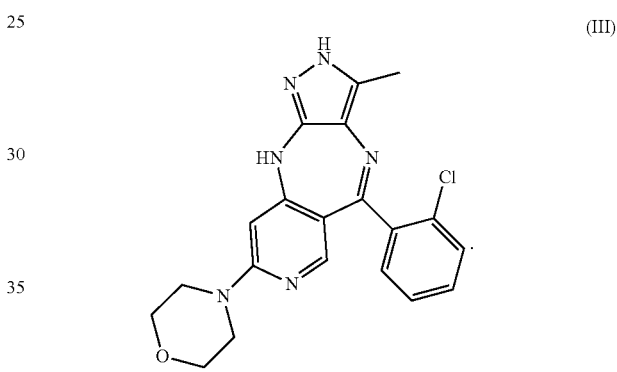

10. A method for preparing the crystal form I according to claim 9, wherein the method comprises:
    dissolving a compound of formula (III) in a single or mixed solvent with heating, and cooling to precipitate the crystal form I;
    or
    suspending a compound of formula (III) in a single or mixed solvent, stirring and filtering to obtain the crystal form I;
    or
    dissolving a compound of formula (III) in a single or mixed solvent, and concentrating under vacuum to obtain the crystal form I;
    or
    washing the compound shown in formula (III) with an appropriate amount of a single or mixed solvent, stirring, filtering and drying to obtain the crystal form I.

11. The method for preparing the crystal form I according to claim 10, wherein the single or mixed solvent is one or more selected from the group consisting of: methanol, ethanol, tetrahydrofuran, 2-methyltetrahydrofuran, dichloromethane, dichloroethane, ethyl acetate, acetonitrile, dimethyl sulfoxide, dimethyl sulfoxide/water, methanol/tetrahydrofuran, methanol/2-methyltetrahydrofuran, methanol/dichloromethane, ethanol/2-methyltetrahydrofuran, and dichloromethane/water.

12. A method for preparing a compound of formula (III), comprising:

(1) reacting a compound of formula (III-A) with a compound of formula (III-B) to give a compound of formula (III-C);

(2) reacting the compound of formula (III-C) with a compound of formula (III-D) to give a compound of formula (III-E);

(3) deprotecting the compound of formula (III-E) to give a compound of formula (III-F) or formula (III-F'); and (4) obtaining the compound of formula (III) from the compound of formula (III-F) or (III-F');

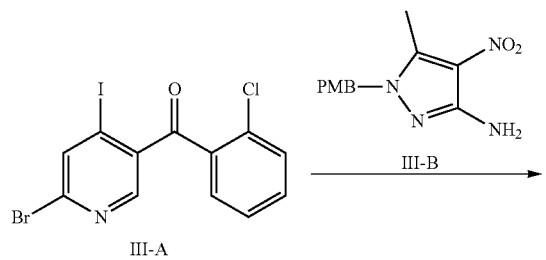
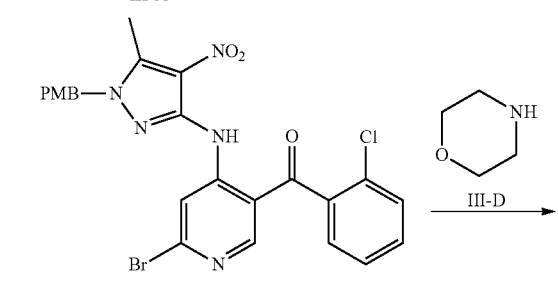
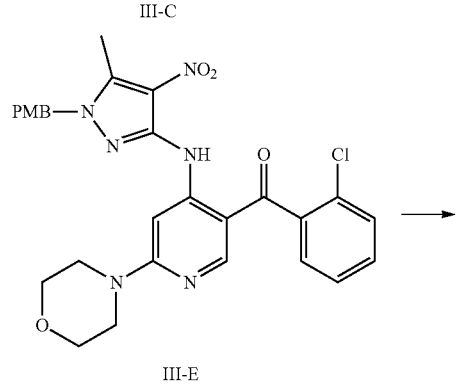
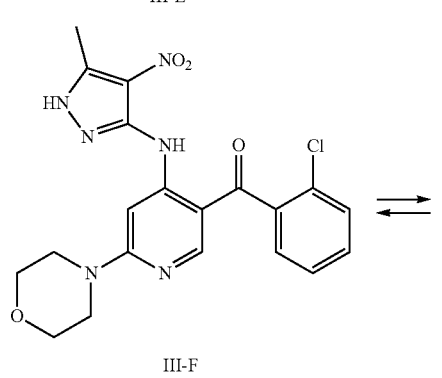

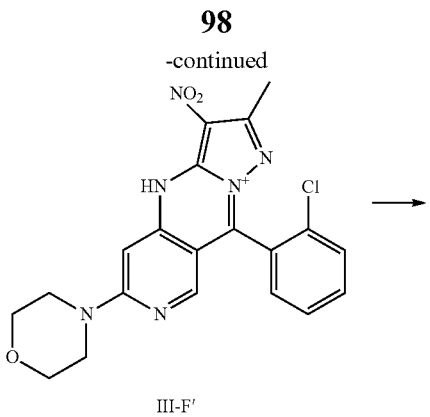

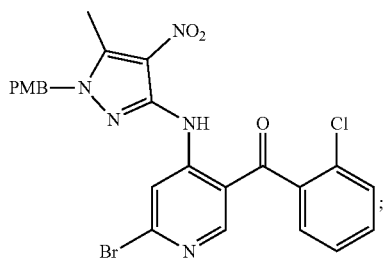

13. An intermediate for preparing a compound of formula (III), wherein the intermediate is represented by the following structural formula:

(III-C)

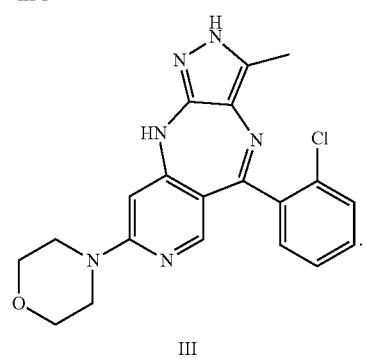

; or (III-E)

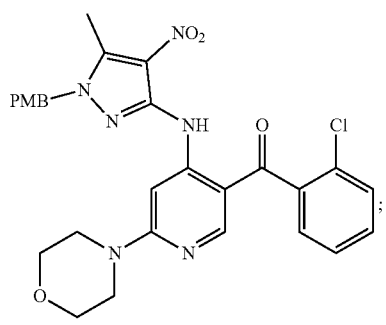

; or

-continued

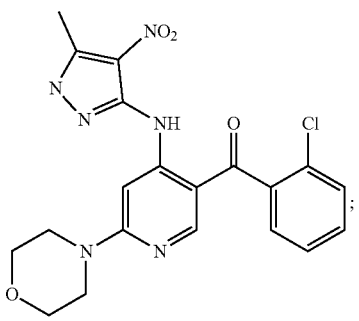
(III-F)

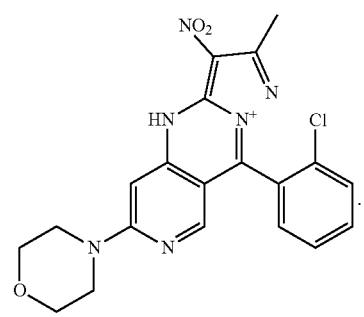
(III-F')

14. A pharmaceutical formulation, comprising the compound, pharmaceutically acceptable salts or stereoisomers thereof according to claim 1, and optionally one or more pharmaceutically acceptable carriers.

15. The pharmaceutical formulation of claim 14, further comprising one or more second therapeutically active agents, wherein the second therapeutically active agents are antimetabolites, growth factor inhibitors, mitosis inhibitors, antitumor hormones, alkylation agents, metals, topoisomerase inhibitors, hormones, immunomodulators, tumor suppressor genes, cancer vaccines, immune checkpoints or tumor immunotherapy-related antibodies, or small molecular drugs.

16. The compound, pharmaceutically acceptable salts or stereoisomers thereof according to claim 2, wherein, $R_1$ is methyl or ethyl.

17. The compound, pharmaceutically acceptable salts or stereoisomers thereof according to claim 3, wherein, the halogen is chlorine.

18. The crystal form I according to claim 9, wherein, the crystal form I also has characteristic peaks at 11.7±0.2°, 14.0±0.2°, 15.00.2°, 20.70.2°, 22.80.2°, 25.40.2°, and 27.8±0.2°.

19. The crystal form I according to claim 9, wherein, Cu-Kα radiation is used for the X-ray powder diffraction.

20. A pharmaceutical composition, comprising the compound, pharmaceutically acceptable salts or stereoisomers thereof according to claim 1, and one or more second therapeutically active agents, wherein the second therapeutically active agents are antimetabolites, growth factor inhibitors, mitosis inhibitors, antitumor hormones, alkylation agents, metals, topoisomerase inhibitors, hormones, immunomodulators, tumor suppressor genes, cancer vaccines, immune checkpoints or tumor immunotherapy-related antibodies, or small molecular drugs.

* * * * *

UNITED STATES PATENT AND TRADEMARK OFFICE
CERTIFICATE OF CORRECTION

PATENT NO. : 10,889,586 B2
APPLICATION NO. : 16/257342
DATED : January 12, 2021
INVENTOR(S) : Frank Wu Page 1 of 2

It is certified that error appears in the above-identified patent and that said Letters Patent is hereby corrected as shown below:

In the Claims

At Column 89, Claim number 8, Line numbers 14-25, please replace

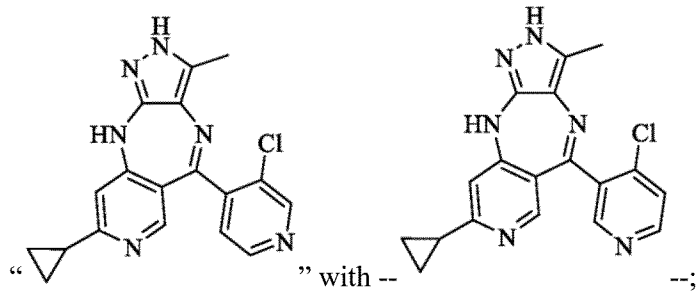

At Column 89, Claim number 8, Line numbers 25-36, please replace

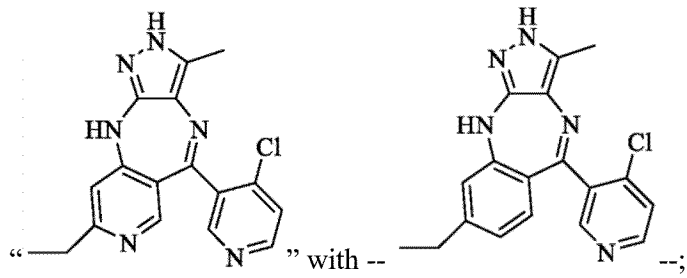

At Column 89, Claim number 8, Line numbers 36-48, please replace

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,889,586 B2